(12) United States Patent
Harrington et al.

(10) Patent No.: US 12,390,426 B1
(45) Date of Patent: Aug. 19, 2025

(54) USE OF ADAMANTANE COMPOSITIONS AND METHODS OF REDUCING FIBROTIC TISSUE

(71) Applicant: Ventoux Biosciences, Inc., Encinitas, CA (US)

(72) Inventors: Kurt Matthew Harrington, Encinitas, CA (US); Kenneth E. Lipson, Encinitas, CA (US)

(73) Assignee: Ventoux Biosciences, Inc., Encinitas, CA (US)

( * ) Notice: Subject to any disclaimer, the term of this patent is extended or adjusted under 35 U.S.C. 154(b) by 0 days.

(21) Appl. No.: 18/661,516

(22) Filed: May 10, 2024

(51) Int. Cl.
*A61K 31/13* (2006.01)
*A61P 19/04* (2006.01)

(52) U.S. Cl.
CPC .............. *A61K 31/13* (2013.01); *A61P 19/04* (2018.01)

(58) Field of Classification Search
CPC .................................. A61K 31/13; A61P 9/04
See application file for complete search history.

(56) References Cited

U.S. PATENT DOCUMENTS 9,649,266 B2 * 5/2017 Edelson ............... A61K 8/4926
2008/0033054 A1 * 2/2008 Merli ..................... A61P 25/16
514/662

OTHER PUBLICATIONS

Karatzas et. al. (PLOS One (2021) 16:1-29). (Year: 2021).*

* cited by examiner

*Primary Examiner* — Marcos L Sznaidman
(74) *Attorney, Agent, or Firm* — PROCOPIO, CORY, HARGREAVES & SAVITCH LLP

(57) ABSTRACT

Provided herein are compositions used to reduce fibrotic tissues associated with an integumentary system fibromatosis condition. Methods of using the compositions to reduce fibrotic tissues associated with an integumentary system fibromatosis condition are also disclosed.

12 Claims, 4 Drawing Sheets

USE OF ADAMANTANE COMPOSITIONS AND METHODS OF REDUCING FIBROTIC TISSUE

BACKGROUND OF THE DISCLOSURE

Fibromatosis conditions are diseases characterized by non-cancerous fibrous overgrowths of dermal and subcutaneous connective tissue causing soft tissue tumors called fibromas. These conditions occur in various locations, for example the palm of the hand (palmar fibromatosis or Dupuytren's disease), the foot (plantar fibromatosis or Ledderhose disease), the shoulder (adhesive capsulitis) or frozen shoulder, the penis (Peyronie's disease) or penile fibromatosis, the interphalangeal joints of the hand (pachydermodactyly), the knuckles (knuckle pad), the gingiva (gingival fibromatosis), various locations of the skin (dermatofibromatosis), along peripheral nerves (neurofibromatosis), subcutaneous tissue (nodular fasciitis), soft tissue (elastofibroma), the face (fibrous papule), and various locations in infants and small children (Congenital generalized fibromatosis/infantile myofibromatosis, aponeurotic fibromas, infantile digital fibromatosis, aggressive infantile fibromatosis, fibromatosis colli, dermatofibrosis lenticularis/Buschke-Ollendorf syndrome), scleroderma, localized scleroderma morphed, localized linear scleroderma, systemic scleroderma, graft-versus-host-disease, burn and post-burn skin fibrosis, cutaneous fibrosis, keloids, hypertrophic scarring, desmoid tumor, desmoid fibromatosis, nephrogenic fibrosing dermopathy, mixed connective tissue disease, scleromyxedema (papular mucinosis), scleredema, eosinophilic fasciitis, eosinophilia-myalgia syndrome, ionizing radiation-induced fibrosis, lipodermatosclerosis, collagenomas, diabetic hand (diabetic fibrosis), and nephrogenic systemic fibrosis. Relevant references include Macaulay et al. (2012), Lanting et al. (2014), Zah et al. (2020), Denkler (2010), Ng et al. (2020), Tripoli et al. (2016), Stewart and Nasciemento (2021), Satish et al. (2015), Wynn (2007).

Fibromatosis conditions can also occur in various locations throughout the body, including in the lung, for example pulmonary fibrosis, idiopathic pulmonary fibrosis, and interstitial lung disease (ILD). Fibromatosis conditions can occur in the heart and cardiac tissue, for example reactive interstitial fibrosis, replacement fibrosis, infiltrate interstitial fibrosis, endomyocardial fibrosis, cardiovascular disease (CVD), heart failure, arrhythmia, and valvular disease. Fibromatosis conditions can occur in the eye and ocular tissue, for example vitreous fibrosis, subepithelial fibrosis, macular degeneration, and strabismus. Fibromatosis conditions can occur in the kidney and renal tissue, for example chronic kidney disease (CKD), diabetic kidney disease (DKD), and progressive kidney disease. Fibromatosis conditions can occur in the liver and hepatic tissue, for example non-alcoholic steatohepatitis (NASH), non-alcoholic fatty liver disease (NAFLD), and liver cirrhosis. Fibromatosis conditions can occur in the abdomen, for example, peritoneal fibrosis. Fibromatosis conditions can occur in the muscle tissue, for example, Duchenne muscular dystrophy, and repetitive motion injury. Fibromatosis conditions can occur in the brain, for example, glial scar. Fibromatosis conditions can occur in the nervous system, for example spinal cord injury. Fibromatosis conditions can occur in the pancreas, for example, chronic pancreatitis, and pancreatic cancer. Fibromatosis conditions can occur in the intestine and intestinal tissue, for example Crohn's disease, Ulcerative Colitis, and irritable bowel disease. Fibromatosis conditions can occur in post-surgery settings, for example fibrotic scars, or adhesions can form between organs following a tissue disturbance, such as infection, trauma, radiation or surgery, resulting in inflammation. Fibromatosis conditions can occur in the bone marrow, for example myelofibrosis, chronic myelogenous leukemia, and myelodyspastic syndrome. Fibromatosis conditions can occur in chronic autoimmune diseases where fibrosis is a major pathological feature, for example Rheumatoid arthritis, systemic Lupus erythrematosus, scleroderma, Crohn's disease, Ulcerative colitis, and myelofibrosis. Fibromatosis conditions can occur in rare diseases, for example, nephrogenic systemic fibrosis, fibrosing hypersensitivity pneumonitis (fHP), and idiopathic retroperitoneal fibrosis.

Fibrosis, or excessive scarring, is a consequence of exaggerated healing response, particularly disproportionate fibroblast proliferation and extracellular matrix (ECM) production in the tissues. Clinically, fibrosis may manifest as thickened, tightened, and hardened areas of the tissues. Ultimately, integumentary system fibrosis may lead to dermal contractures that affect the ability to flex and extend the joints.

SUMMARY OF THE DISCLOSURE

The disclosure relates generally to the treatment of fibromatosis conditions, and more particularly, treatment of integumentary system fibromatosis conditions. In one embodiment a pharmaceutical composition for treating a fibromatosis condition, the composition comprising a therapeutically effective amount of an adamantane derivative, preferably memantine or a pharmaceutically acceptable salt thereof and a pharmaceutically acceptable carrier is disclosed.

One aspect of the present disclosure relates to an adamantane derivative, preferably memantine composition, wherein the fibromatosis condition is an integumentary system fibromatosis condition.

In some embodiments, the fibromatosis condition is palmar fibromatosis (Dupuytren's disease), plantar fibromatosis (Ledderhose disease), adhesive capsulitis (frozen shoulder), surgical adhesions, scleroderma, keloids, hypertrophic scarring, diabetic fibrosis (diabetic hand), nephrogenic systemic fibrosis or penile fibromatosis (Peyronie's disease).

In some embodiments, the fibromatosis condition is palmar fibromatosis (Dupuytren's disease), plantar fibromatosis (Ledderhose disease), scleroderma, or diabetic fibrosis (diabetic hand).

In some embodiments, the fibromatosis condition is palmar fibromatosis (Dupuytren's disease) or plantar fibromatosis (Ledderhose disease).

In some embodiments, the fibromatosis condition is palmar fibromatosis (Dupuytren's disease). In some embodiments, the fibromatosis condition is plantar fibromatosis (Ledderhose disease). In some embodiments, the fibromatosis condition is adhesive capsulitis (frozen shoulder). In some embodiments, the fibromatosis condition is surgical adhesions. In some embodiments, the fibromatosis condition is scleroderma. In some embodiments, the fibromatosis condition is keloids. In some embodiments, the fibromatosis condition is hypertrophic scarring. In some embodiments, the fibromatosis condition is diabetic fibrosis (diabetic hand). In some embodiments, the fibromatosis condition is nephrogenic systemic fibrosis. In some embodiments, the fibromatosis condition is penile fibromatosis (Peyronie's disease).

According to one aspect, the disclosed method or composition leads to a reduction of fibrotic tissue volume. In some embodiments, volume can be measured by histopathological analysis, magnetic resonance imaging (MRI), or computed topography (CT) scan. In some embodiments, the fibrotic tissue volume is reduced by about 1% to about 30%. In some embodiments, the fibrotic tissue volume is reduced by about 3% to about 30%. In some embodiments, the fibrotic tissue volume is reduced by about 5% to about 30%. In some embodiments, the fibrotic tissue volume is reduced by about 10% to about 30%. In some embodiments, the fibrotic tissue volume is reduced by about 15% to about 30%.

According to one aspect, the disclosed method or composition leads to a reduction of fibrotic tissue volume. In some embodiments, volume can be measured by histopathological analysis, MRI, or CT scan. In some embodiments, the fibrotic tissue volume is reduced by about 1% to about 60%. In some embodiments, the fibrotic tissue volume is reduced by about 3% to about 60%. In some embodiments, the fibrotic tissue volume is reduced by about 5% to about 60%. In some embodiments, the fibrotic tissue volume is reduced by about 10% to about 60%. In some embodiments, the fibrotic tissue volume is reduced by about 15% to about 60%. In some embodiments, the fibrotic tissue volume is reduced by about 20% to about 60%. In some embodiments, the fibrotic tissue volume is reduced by about 1% to about 40%. In some embodiments, the fibrotic tissue volume is reduced by about 3% to about 40%. In some embodiments, the fibrotic tissue volume is reduced by about 5% to about 40%. In some embodiments, the fibrotic tissue volume is reduced by about 10% to about 40%. In some embodiments, the fibrotic tissue volume is reduced by about 15% to about 40%. In some embodiments, the fibrotic tissue volume is reduced by about 20% to about 40%.

According to some embodiments, the disclosed method or composition leads to a reduction of fibrotic tissue dermal fibrosis area measured by histopathological analysis, MRI, or CT scan. In some embodiments, the fibrotic tissue dermal fibrosis area is reduced by about 1% to about 50%. In some embodiments, the fibrotic tissue dermal fibrosis area is reduced by about 3% to about 50%. In some embodiments, the fibrotic tissue dermal fibrosis area is reduced by about 5% to about 50%. In some embodiments, the fibrotic tissue dermal fibrosis area is reduced by about 10% to about 50%. In some embodiments, the fibrotic tissue dermal fibrosis area is reduced by about 15% to about 50%. In some embodiments, the fibrotic tissue dermal fibrosis area is reduced by about 1% to about 25%. In some embodiments, the fibrotic tissue dermal fibrosis area is reduced by about 3% to about 25%. In some embodiments, the fibrotic tissue dermal fibrosis area is reduced by about 5% to about 25%. In some embodiments, the fibrotic tissue dermal fibrosis area is reduced by about 10% to about 25%. In some embodiments, the fibrotic tissue dermal fibrosis area is reduced by about 15% to about 25%.

According to one aspect, the disclosed method or composition leads to a reduction of fibrotic tissue dermal fibrosis percent. In some embodiments, the fibrotic tissue dermal fibrosis percent is reduced by about 1% to about 70%. In some embodiments, the fibrotic tissue dermal fibrosis percent is reduced by about 3% to about 70%. In some embodiments, the fibrotic tissue dermal fibrosis percent is reduced by about 5% to about 70%. In some embodiments, the fibrotic tissue dermal fibrosis percent is reduced by about 10% to about 70%. In some embodiments, the fibrotic tissue dermal fibrosis percent is reduced by about 15% to about 70%. In some embodiments, the fibrotic tissue dermal fibrosis percent is reduced by about 20% to about 70%. In some embodiments, the fibrotic tissue dermal fibrosis percent is reduced by about 1% to about 35%. In some embodiments, the fibrotic tissue dermal fibrosis percent is reduced by about 3% to about 35%. In some embodiments, the fibrotic tissue dermal fibrosis percent is reduced by about 5% to about 35%. In some embodiments, the fibrotic tissue dermal fibrosis percent is reduced by about 10% to about 35%. In some embodiments, the fibrotic tissue dermal fibrosis percent is reduced by about 15% to about 35%. In some embodiments, the fibrotic tissue dermal fibrosis percent is reduced by about 20% to about 35%. In some embodiments, the fibrotic tissue dermal fibrosis percent is reduced by about 25% to about 35%.

According to some embodiments, the disclosed method or composition leads to a reduction of fibrotic tissue epidermal fibrosis area measured by histopathological analysis, MRI, or CT scan. In some embodiments, the fibrotic tissue epidermal fibrosis area is reduced by about 1% to about 75%. In some embodiments, the fibrotic tissue epidermal fibrosis area is reduced by about 3% to about 75%. In some embodiments, the fibrotic tissue epidermal fibrosis area is reduced by about 5% to about 75%. In some embodiments, the fibrotic tissue epidermal fibrosis area is reduced by about 10% to about 75%. In some embodiments, the fibrotic tissue epidermal fibrosis area is reduced by about 15% to about 75%. In some embodiments, the fibrotic tissue epidermal fibrosis area is reduced by about 20% to about 75%. In some embodiments, the fibrotic tissue epidermal fibrosis area is reduced by about 25% to about 75%. In some embodiments, the fibrotic tissue epidermal fibrosis area is reduced by about 1% to about 50%. In some embodiments, the fibrotic tissue epidermal fibrosis area is reduced by about 3% to about 50%. In some embodiments, the fibrotic tissue epidermal fibrosis area is reduced by about 5% to about 50%. In some embodiments, the fibrotic tissue epidermal fibrosis area is reduced by about 10% to about 50%. In some embodiments, the fibrotic tissue epidermal fibrosis area is reduced by about 15% to about 50%. In some embodiments, the fibrotic tissue epidermal fibrosis area is reduced by about 20% to about 50%. In some embodiments, the fibrotic tissue epidermal fibrosis area is reduced by about 25% to about 50%. In some embodiments, the fibrotic tissue epidermal fibrosis area is reduced by about 30% to about 50%.

According to one aspect, the disclosed method or composition leads to a reduction of fibrotic tissue epidermal fibrosis percent. In some embodiments, the fibrotic tissue epidermal fibrosis percent is reduced by about 1% to about 75%. In some embodiments, the fibrotic tissue epidermal fibrosis percent is reduced by about 3% to about 75%. In some embodiments, the fibrotic tissue epidermal fibrosis percent is reduced by about 5% to about 75%. In some embodiments, the fibrotic tissue epidermal fibrosis percent is reduced by about 10% to about 75%. In some embodiments, the fibrotic tissue epidermal fibrosis percent is reduced by about 15% to about 75%. In some embodiments, the fibrotic tissue epidermal fibrosis percent is reduced by about 20% to about 75%. In some embodiments, the fibrotic tissue epidermal fibrosis percent is reduced by about 25% to about 75%. In some embodiments, the fibrotic tissue epidermal fibrosis percent is reduced by about 1% to about 50%. In some embodiments, the fibrotic tissue epidermal fibrosis percent is reduced by about 3% to about 50%. In some embodiments, the fibrotic tissue epidermal fibrosis percent is reduced by about 5% to about 50%. In some embodiments, the fibrotic tissue epidermal fibrosis percent is reduced by about 10% to about 50%. In some embodiments, the fibrotic tissue epidermal fibrosis percent is reduced by about 15% to about 50%. In some embodiments, the fibrotic tissue epidermal fibrosis percent is reduced by about 20% to about 50%. In some embodiments, the fibrotic tissue epidermal fibrosis percent is reduced by about 25% to about 50%. In some embodiments, the fibrotic tissue epidermal fibrosis percent is reduced by about 30% to about 50%.

According to one aspect, the disclosed method or composition leads to a reduction of fibrotic tissue stiffness or rigidity. In some embodiments, the fibrotic tissue stiffness or rigidity is reduced by about 1% to about 75%. In some embodiments, the fibrotic tissue stiffness or rigidity is reduced by about 3% to about 75%. In some embodiments, the fibrotic tissue stiffness or rigidity is reduced by about 5% to about 75%. In some embodiments, the fibrotic tissue stiffness or rigidity is reduced by about 10% to about 75%. In some embodiments, the fibrotic tissue stiffness or rigidity is reduced by about 15% to about 75%. In some embodiments, the fibrotic tissue stiffness or rigidity is reduced by about 20% to about 75%. In some embodiments, the fibrotic tissue stiffness or rigidity is reduced by about 25% to about 75%. In some embodiments, the fibrotic tissue stiffness or rigidity is reduced by about 1% to about 45%. In some embodiments, the fibrotic tissue stiffness or rigidity is reduced by about 3% to about 45%. In some embodiments, the fibrotic tissue stiffness or rigidity is reduced by about 5% to about 45%. In some embodiments, the fibrotic tissue stiffness or rigidity is reduced by about 10% to about 45%. In some embodiments, the fibrotic tissue stiffness or rigidity is reduced by about 15% to about 45%. In some embodiments, the fibrotic tissue stiffness or rigidity is reduced by about 20% to about 45%. In some embodiments, the fibrotic tissue stiffness or rigidity is reduced by about 25% to about 45%. In some embodiments, the fibrotic tissue stiffness or rigidity is reduced by about 30% to about 45%.

In some embodiments, the composition comprises an injectable composition.

Another aspect of the present disclosure relates to a reducing fibromatosis in a subject in need thereof disclosed herein, the method comprising contacting the fibrotic tissue with a composition comprising a therapeutically effective amount of an adamantane derivative, preferably memantine or a pharmaceutically acceptable salt thereof and a pharmaceutically acceptable carrier.

In some embodiments, the subject is a mammal. In some embodiments, the mammal is a human.

In some embodiments, the fibromatosis condition is associated with a fibromatosis condition selected from the group consisting of palmar fibromatosis (Dupuytren's disease), plantar fibromatosis (Ledderhose disease), adhesive capsulitis (frozen shoulder), surgical adhesions, scleroderma, keloids, hypertrophic scarring, diabetic fibrosis (diabetic hand), nephrogenic systemic fibrosis or penile fibromatosis (Peyronie's disease).

In some embodiments, the fibromatosis condition is palmar fibromatosis (Dupuytren's disease). In some embodiments, the fibromatosis condition is plantar fibromatosis (Ledderhose disease). In some embodiments, the fibromatosis condition is adhesive capsulitis (frozen shoulder). In some embodiments, the fibromatosis condition is surgical adhesions. In some embodiments, the fibromatosis condition is scleroderma. In some embodiments, the fibromatosis condition is keloids. In some embodiments, the fibromatosis condition is hypertrophic scarring. In some embodiments, the fibromatosis condition is diabetic fibrosis (diabetic hand). In some embodiments, the fibromatosis condition is nephrogenic systemic fibrosis. In some embodiments, the fibromatosis condition is penile fibromatosis (Peyronie's disease).

According to some embodiments, the disclosed method or composition leads to a reduction of fibrotic tissue volume, measured by histopathological analysis, MRI, or CT scan. In some embodiments, the fibrotic tissue volume is reduced by about 1% to about 30%. In some embodiments, the fibrotic tissue volume is reduced by about 1% to about 25%. In some embodiments, the fibrotic tissue volume is reduced by about 1% to about 20%. In some embodiments, the fibrotic tissue volume is reduced by about 1% to about 15%. In some embodiments, the fibrotic tissue volume is reduced by about 1% to about 10%. In some embodiments, the fibrotic tissue volume is reduced by about 1% to about 5%.

According to some embodiments, the disclosed method or composition leads to a reduction of fibrotic tissue volume measured by histopathological analysis, MRI, or CT scan. In some embodiments, the fibrotic tissue volume is reduced by about 1% to about 60%. In some embodiments, the fibrotic tissue volume is reduced by about 1% to about 55%. In some embodiments, the fibrotic tissue volume is reduced by about 1% to about 50%. In some embodiments, the fibrotic tissue volume is reduced by about 1% to about 45%. In some embodiments, the fibrotic tissue volume is reduced by about 1% to about 40%. In some embodiments, the fibrotic tissue volume is reduced by about 1% to about 35%. In some embodiments, the fibrotic tissue volume is reduced by about 1% to about 30%. In some embodiments, the fibrotic tissue volume is reduced by about 1% to about 25%. In some embodiments, the fibrotic tissue volume is reduced by about 1% to about 20%. In some embodiments, the fibrotic tissue volume is reduced by about 1% to about 15%. In some embodiments, the fibrotic tissue volume is reduced by about 1% to about 10%. In some embodiments, the fibrotic tissue volume is reduced by about 1% to about 5%.

According to one aspect, the disclosed method or composition leads to a reduction of fibrotic tissue dermal fibrosis area. In some embodiments, the fibrotic tissue dermal fibrosis area is reduced by about 1% to about 50%. In some embodiments, the fibrotic tissue dermal fibrosis area is reduced by about 1% to about 45%. In some embodiments, the fibrotic tissue dermal fibrosis area is reduced by about 1% to about 40%. In some embodiments, the fibrotic tissue dermal fibrosis area is reduced by about 1% to about 35%. In some embodiments, the fibrotic tissue dermal fibrosis area is reduced by about 1% to about 30%. In some embodiments, the fibrotic tissue dermal fibrosis area is reduced by about 1% to about 25%. In some embodiments, the fibrotic tissue dermal fibrosis area is reduced by about 1% to about 20%. In some embodiments, the fibrotic tissue dermal fibrosis area is reduced by about 1% to about 15%. In some embodiments, the fibrotic tissue dermal fibrosis area is reduced by about 1% to about 10%. In some embodiments, the fibrotic tissue dermal fibrosis area is reduced by about 1% to about 5%.

According to one aspect, the disclosed method or composition leads to a reduction of fibrotic tissue dermal fibrosis percent. In some embodiments, the fibrotic tissue dermal fibrosis percent is reduced by about 1% to about 70%. In some embodiments, the fibrotic tissue dermal fibrosis percent is reduced by about 1% to about 65%. In some embodiments, the fibrotic tissue dermal fibrosis percent is reduced by about 1% to about 55%. In some embodiments, the fibrotic tissue dermal fibrosis percent is reduced by about 1% to about 50%. In some embodiments, the fibrotic tissue dermal fibrosis percent is reduced by about 1% to about 45%. In some embodiments, the fibrotic tissue dermal fibrosis percent is reduced by about 1% to about 40%. In some embodiments, the fibrotic tissue dermal fibrosis percent is reduced by about 1% to about 35%. In some embodiments, the fibrotic tissue dermal fibrosis percent is reduced by about 1% to about 30%. In some embodiments, the fibrotic tissue dermal fibrosis percent is reduced by about 1% to about 25%. In some embodiments, the fibrotic tissue dermal fibrosis percent is reduced by about 1% to about 20%. In some embodiments, the fibrotic tissue dermal fibrosis percent is reduced by about 1% to about 15%. In some embodiments, the fibrotic tissue dermal fibrosis percent is reduced by about 1% to about 10%. In some embodiments, the fibrotic tissue dermal fibrosis percent is reduced by about 1% to about 5%.

According to one aspect, the disclosed method or composition leads to a reduction of fibrotic tissue epidermal fibrosis area. In some embodiments, the fibrotic tissue epidermal fibrosis area is reduced by about 1% to about 75%. In some embodiments, the fibrotic tissue epidermal fibrosis area is reduced by about 1% to about 70%. In some embodiments, the fibrotic tissue epidermal fibrosis area is reduced by about 1% to about 65%. In some embodiments, the fibrotic tissue epidermal fibrosis area is reduced by about 1% to about 60%. In some embodiments, the fibrotic tissue epidermal fibrosis area is reduced by about 1% to about 55%. In some embodiments, the fibrotic tissue epidermal fibrosis area is reduced by about 1% to about 50%. In some embodiments, the fibrotic tissue epidermal fibrosis area is reduced by about 1% to about 45%. In some embodiments, the fibrotic tissue epidermal fibrosis area is reduced by about 1% to about 40%. In some embodiments, the fibrotic tissue epidermal fibrosis area is reduced by about 1% to about 35%. In some embodiments, the fibrotic tissue epidermal fibrosis area is reduced by about 1% to about 30%. In some embodiments, the fibrotic tissue epidermal fibrosis area is reduced by about 1% to about 25%. In some embodiments, the fibrotic tissue epidermal fibrosis area is reduced by about 1% to about 20%. In some embodiments, the fibrotic tissue epidermal fibrosis area is reduced by about 1% to about 15%. In some embodiments, the fibrotic tissue epidermal fibrosis area is reduced by about 1% to about 10%. In some embodiments, the fibrotic tissue epidermal fibrosis area is reduced by about 1% to about 5%.

According to one aspect, the disclosed method or composition leads to a reduction of fibrotic tissue epidermal fibrosis percent. In some embodiments, the fibrotic tissue epidermal fibrosis percent is reduced by about 1% to about 75%. In some embodiments, the fibrotic tissue epidermal fibrosis percent is reduced by about 1% to about 70%. In some embodiments, the fibrotic tissue epidermal fibrosis percent is reduced by about 1% to about 65%. In some embodiments, the fibrotic tissue epidermal fibrosis percent is reduced by about 1% to about 60%. In some embodiments, the fibrotic tissue epidermal fibrosis percent is reduced by about 1% to about 55%. In some embodiments, the fibrotic tissue epidermal fibrosis percent is reduced by about 1% to about 50%. In some embodiments, the fibrotic tissue epidermal fibrosis percent is reduced by about 1% to about 45%. In some embodiments, the fibrotic tissue epidermal fibrosis percent is reduced by about 1% to about 40%. In some embodiments, the fibrotic tissue epidermal fibrosis percent is reduced by about 1% to about 35%. In some embodiments, the fibrotic tissue epidermal fibrosis percent is reduced by about 1% to about 30%. In some embodiments, the fibrotic tissue epidermal fibrosis percent is reduced by about 1% to about 25%. In some embodiments, the fibrotic tissue epidermal fibrosis percent is reduced by about 1% to about 20%. In some embodiments, the fibrotic tissue epidermal fibrosis percent is reduced by about 1% to about 15%. In some embodiments, the fibrotic tissue epidermal fibrosis percent is reduced by about 1% to about 10%. In some embodiments, the fibrotic tissue epidermal fibrosis percent is reduced by about 1% to about 5%.

According to one aspect, the disclosed method or composition leads to a reduction of fibrotic tissue stiffness or rigidity. In some embodiments, the fibrotic tissue stiffness or rigidity is reduced by about 1% to about 75%. In some embodiments, the fibrotic tissue stiffness or rigidity is reduced by about 1% to about 70%. In some embodiments, the fibrotic tissue stiffness or rigidity is reduced by about 1% to about 65%. In some embodiments, the fibrotic tissue stiffness or rigidity is reduced by about 1% to about 60%. In some embodiments, the fibrotic tissue stiffness or rigidity is reduced by about 1% to about 55%. In some embodiments, the fibrotic tissue stiffness or rigidity is reduced by about 1% to about 50%. In some embodiments, the fibrotic tissue stiffness or rigidity is reduced by about 1% to about 45%. In some embodiments, the fibrotic tissue stiffness or rigidity is reduced by about 1% to about 40%. In some embodiments, the fibrotic tissue stiffness or rigidity is reduced by about 1% to about 35%. In some embodiments, the fibrotic tissue stiffness or rigidity is reduced by about 1% to about 30%. In some embodiments, the fibrotic tissue stiffness or rigidity is reduced by about 1% to about 25%. In some embodiments, the fibrotic tissue stiffness or rigidity is reduced by about 1% to about 20%. In some embodiments, the fibrotic tissue stiffness or rigidity is reduced by about 1% to about 15%. In some embodiments, the fibrotic tissue stiffness or rigidity is reduced by about 1% to about 10%. In some embodiments, the fibrotic tissue stiffness or rigidity is reduced by about 1% to about 5%.

Another aspect of the present disclosure relates to the method of reducing fibromatosis in a subject in need thereof, wherein the contacting the fibrotic tissue with the composition comprising the therapeutically effective amount of an adamantane derivative, preferably memantine or a pharmaceutically acceptable salt thereof and a pharmaceutically acceptable carrier is an injectable composition.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE DISCLOSURE

Figure 1:
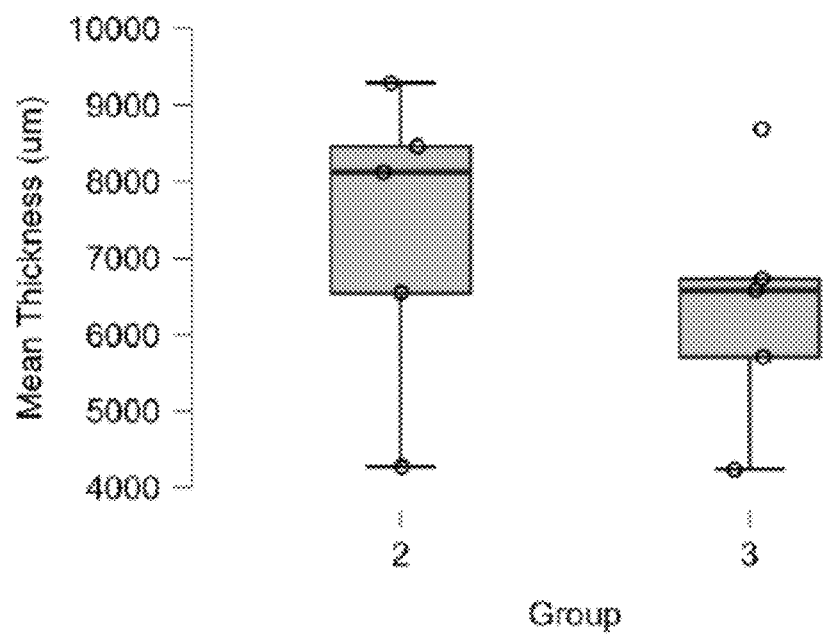
FIG. 1 illustrates the mean dermal thickness, measured in micrometers, between bleomycin-treated+memantine and bleomycin-treated study subjects.
Figure 2:
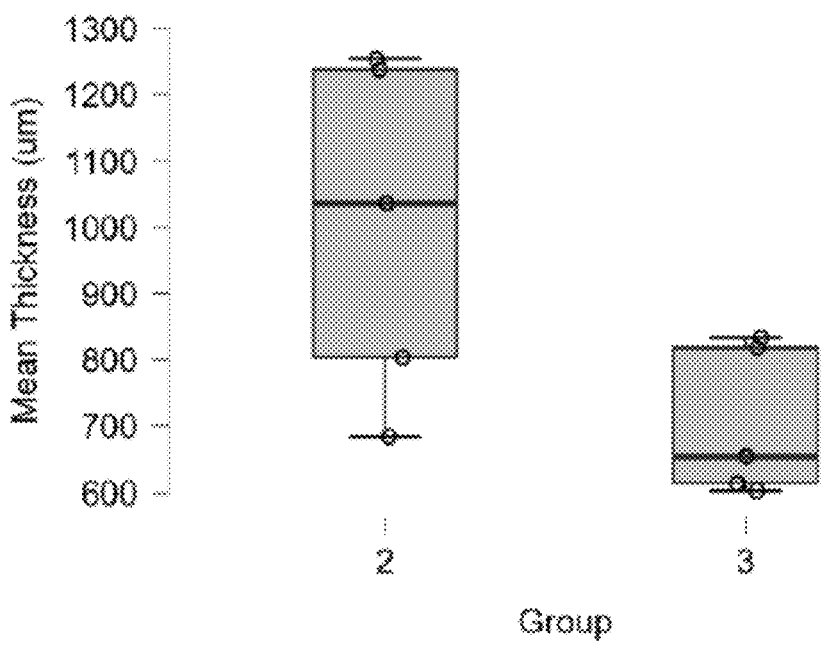
FIG. 2 illustrates the mean epidermal thickness, measured in micrometers, between bleomycin-treated+memantine and bleomycin-treated study subjects.
Figure 3:
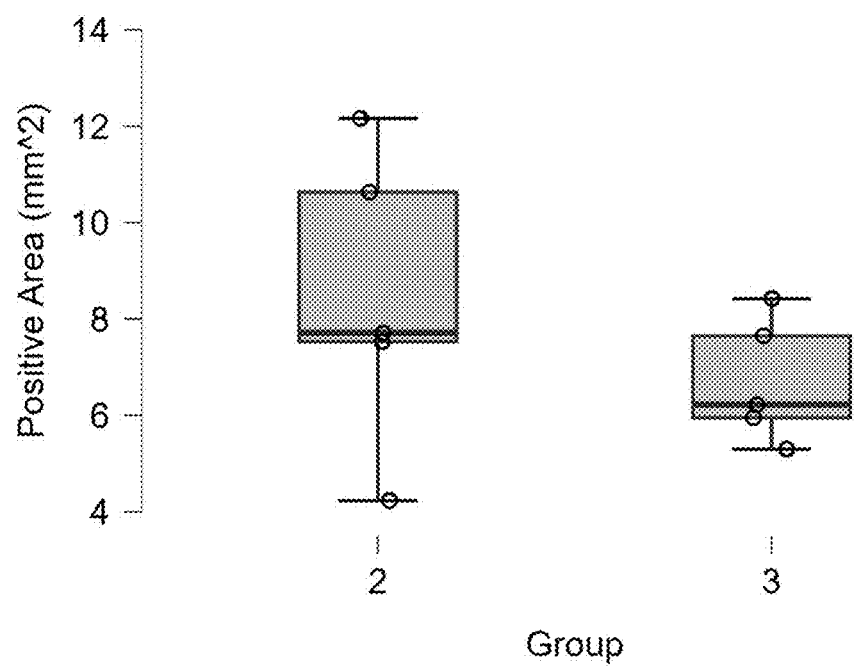
FIG. 3 illustrates dermis fibrosis area, measured in micrometers squared, between bleomycin-treated+memantine and bleomycin-treated study subjects.
Figure 4:
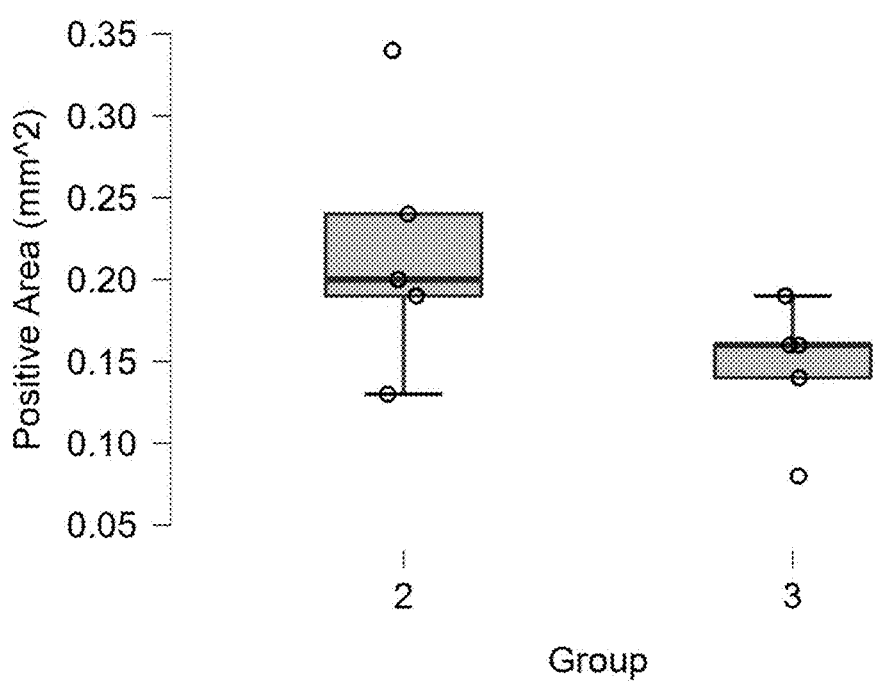
FIG. 4 illustrates epidermis fibrosis area, measured in micrometers squared, between bleomycin-treated+memantine and bleomycin-treated study subjects.
Figure 5:
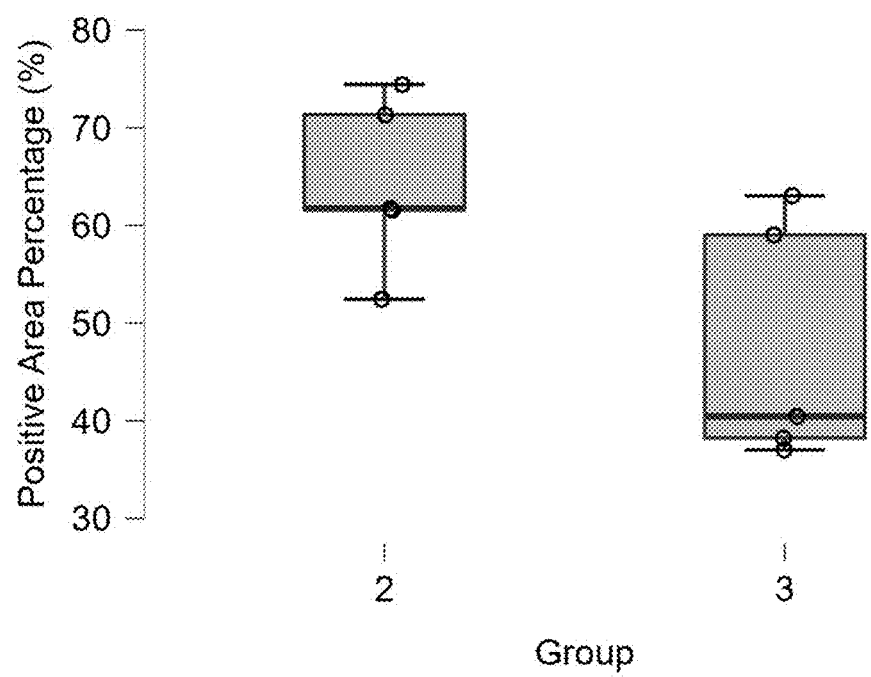
FIG. 5 illustrates dermis fibrosis percent, measured in micrometers squared, between bleomycin-treated+memantine and bleomycin-treated study subjects.
Figure 6:
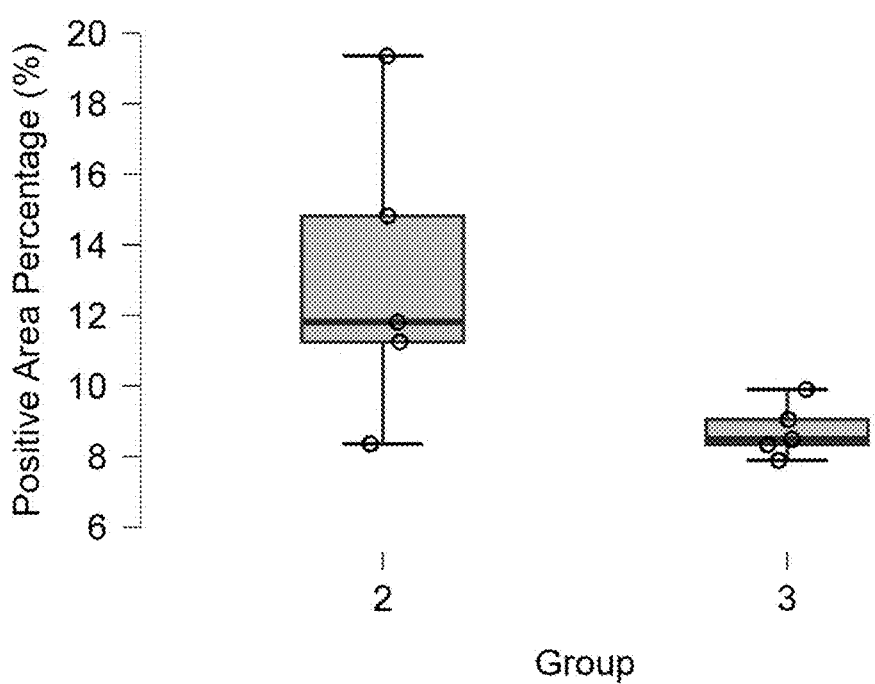
FIG. 6 illustrates epidermis fibrosis percent, measured in micrometers squared, between bleomycin-treated+memantine and bleomycin-treated study subjects.
Figure 7:
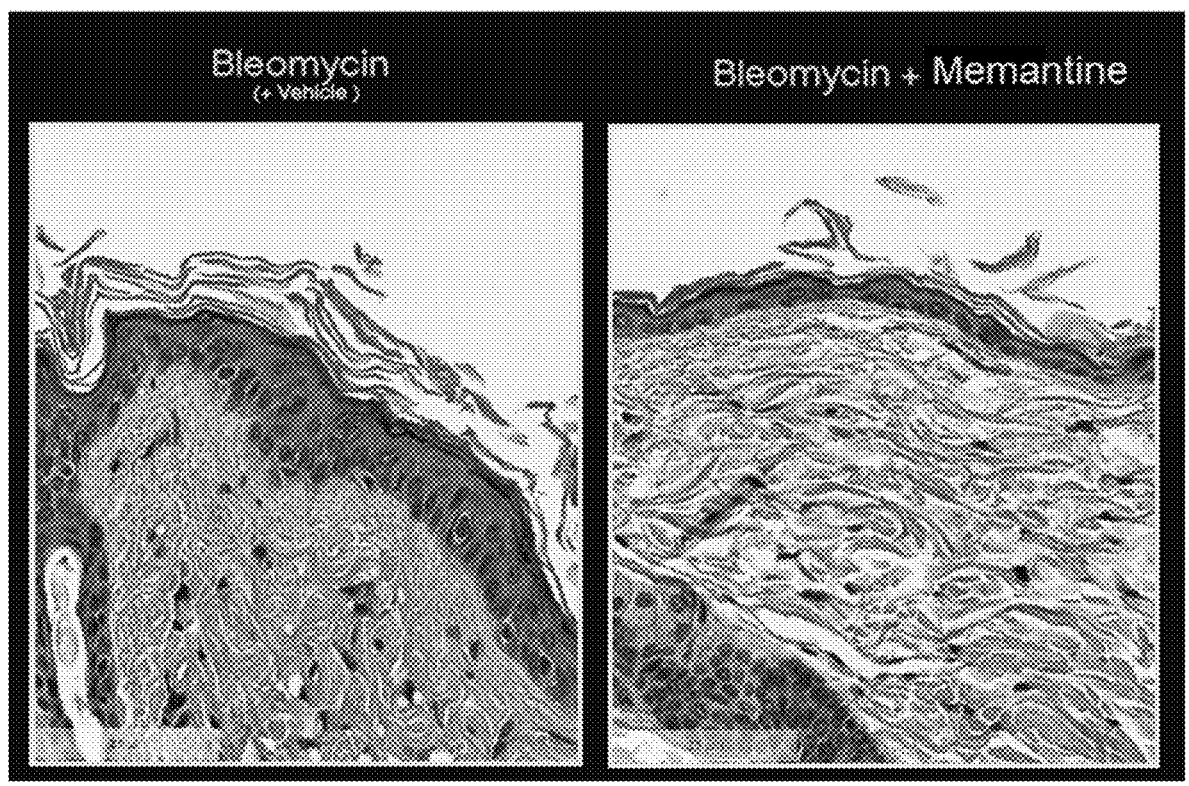
FIG. 7 illustrates skin tissue images from selected study subjects, representative of mean epidermal thickening, displayed at 40× magnification.

Provided herein, in some embodiments, are adamantane derivatives, preferably memantine compositions. Also provided herein, in some embodiments, are methods of using adamantane derivatives, preferably memantine compositions to reduce fibrotic tissue associated with integumentary system fibromatosis conditions.

Detailed descriptions of one or more embodiments are provided herein. It is to be understood, however, that the present disclosure is embodied in various forms. Therefore, specific details disclosed herein are not to be interpreted as limiting, but rather as a basis for the claims and as a representative basis for teaching one skilled in the art to employ the present disclosure in any appropriate manner.

Certain Definitions

As used herein in the specification and in the claims, the articles "a" and "an" are used to refer to one or to more than one (i.e., to at least one) of the grammatical object of the article unless the context clearly indicates otherwise. By way of example, "an element" means one element or more than one element.

As used herein in the specification and in the claims, the phrase "and/or," should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least 5 one, optionally including more than one, B, with no A present (and optionally including elements other than A); in yet another embodiment, to at least one, optionally including more than one, A, and at least one, optionally including more than one, B (and optionally including other elements); etc.

Wherever the phrase "for example," "such as," "including," and the like are used herein, the phrase "and without limitation" is understood to follow unless explicitly stated otherwise. Similarly, "an example," "exemplary," and the like are understood to be non-limiting.

The term "about" is used to indicate that a value includes the standard level of error for the device or method being employed to determine the value. In some embodiments, the level of error is 10%. In some embodiments, the level of error is 9%. In some embodiments, the level of error is 8%. In some embodiments, the level of error is 7%. In some embodiments, the level of error is 6%. In some embodiments, the level of error is 5%.

The terms "treat," "treating," and "treatment," in the context of treating a disease, disorder, or condition are meant to include alleviating or abrogating a disorder, disease, or condition, or one or more of the symptoms associated with the disorder, disease, or condition; or slowing the progression, spread or worsening of a disease, disorder or condition or of one or more symptoms thereof. Often, the beneficial effects that a subject derives from a therapeutic agent do not result in a complete cure of the disease, disorder or condition. In some embodiments, the terms "treat," "treating," and "treatment," include curing a disorder, disease, or condition; reducing, arresting, or reversing the progression of a disorder, disease, or condition; reducing or ameliorating symptom(s) of a disorder, disease or condition; reducing the length of stay in a hospital; reducing the length of stay in an infectious disease unit and/or intensive care unit; or slowing (including stopping) the progression/development of symptoms.

The term "fibromatosis", as used herein, refers to growth, including histologically benign growth, of fibroblastic and myofibroblastic cells, with a potential to recur and invade local organs.

The terms "prevent," "preventing," and "prevention," as used herein, shall refer to a decrease in the occurrence of a disease or decrease in the risk of acquiring a disease or its associated symptoms in a subject. The prevention may be complete, e.g., the total absence of disease or pathological cells in a subject. The prevention may also be partial, such that the occurrence of the disease or pathological cells in a subject is less than, occurs later than, or develops more slowly than that which would have occurred without the present invention.

The terms "administer," "administering," or "administration," as used herein, refer to implanting, ingesting, injecting, inhaling, or otherwise absorbing a compound or composition, regardless of form. For example, the methods disclosed herein include administration of an effective amount of a compound or composition to achieve the desired or stated effect.

The term "therapeutically effective amount" refers to the amount of a drug or other pharmaceutical agent (e.g., a compound disclosed herein), that will elicit the biological and/or medical response of a tissue, system, animal or human (e.g., subject or patient) that is being sought, for instance, by a researcher or clinician. Furthermore, the term "therapeutically effective amount" means any amount, as compared to a corresponding subject (e.g., patient) who has not received such amount, which is sufficient to decrease the rate of advancement of, prevent development of, or alleviate to some extent, one or more of the symptoms of the condition or disorder being treated. The therapeutically effective amount will vary depending on the compound, the disease and its severity and the age, weight, etc., of the mammal to be treated. In addition, the therapeutically effective amount can be administered in one or more administrations, applications or dosages and is not intended to be limited to a particular formulation or administration route.

As used herein, the term "subject or patient" used interchangeably herein refers to an animal, including, but not limited to, a primate (e.g., human), monkey, cow, pig, sheep, goat, horse, dog, cat, rabbit, rat, or mouse. In some embodiments, the subject is a human to be treated by the methods and compositions of the present disclosure. In some embodiments, the methods described herein further include the step of identifying a subject (e.g., a patient) in need of such treatment (e.g., by way of biopsy, endoscopy, or other conventional method known in the art).

As used herein, the term "area" refers to a measurement of the amount of space in a two-dimensional region. In some embodiments, the area can be calculated by multiplying the length by the width of the analyzed region of interest selected in the whole section. In some embodiments, the area may be expressed as percentage of fibrosis tissue area divided by the total area scanned.

As used herein, the term "percent" refers to the ratio of the area of fibrosis compared to the entire tissue sample area. The percentage can be assessed by calculating the ratio of fibrosis tissue area divided by the total section area.

As used herein, the term "volume" refers to the amount of tissue fibrosis space. In some embodiments, the volume can be assessed by taking the area multiplied by the thickness of the tissue within a specified sample. The thickness refers to the perpendicular dimension of area.

The term "stiffness" or "rigidity" refers to the tissue quality of being firm and difficult to move or the tissue quality of being rigid, stiff, fixed, or an inability to bend.

Stiffness, or rigidity, of a material may be defined as the extent to which a material resists deformation in response to an applied force. Stiffness can be used to indicate whether a material is compliant (soft) or rigid (hard). In biology, stiffness has been used to collectively represent mechanical properties of a biological substrate. The tissues, which are composed of a variety of different extracellular matrix (ECM) molecules, feature a wide range of elastic moduli, and each tissue type and organ has specific stiffness for fulfilling physiological needs. For example, bone is much stiffer than other tissues, for its primary function is to provide structure and protect our internal organs.

Prolonged changes in ECM mechanics can result in the development and progression of disease state. The ECM is essential for normal wound healing processes, but excessive matrix deposition, as is observed with fibrotic diseases, can lead to organ dysfunction. Fibrotic diseases, which include pulmonary fibrosis, systemic sclerosis, liver cirrhosis, cardiovascular disease, Dupuytren's disease, and others can be characterized by the hyperproliferation of fibroblasts, their differentiation into myofibroblasts, and excessive ECM synthesis and secretion. Constitutive activation of collagen-secreting myofibroblast-like cells leads to increases in both collagen amount and concentration, which throws off normal tissue homeostasis to more heavily favor production and leads to tissue stiffening. This imbalance is often exacerbated by deregulated expression of matrix metalloproteinases (MMPs)—which act to degrade ECM—and tissue inhibitors of metalloproteinases (TIMPs)—which inhibit the activity of MMPs. Specifically, MMP expression is often downregulated and TIMP expression becomes upregulated, resulting in incomplete matrix remodeling and irreversible fibrosis.65 This imbalance, in turn, compromises normal tissue function and drives disease progression. In addition, variations in ECM composition likewise have a profound effect on the biomechanical properties of a tissue. For instance, collagen and elastin fibers are the main structural components in pulmonary connective tissue, but their elastic properties are substantially different. The elastic modulus of collagen fibrils is in the range of 1200 megapascals (MPa), whereas the elastic modulus of elastin is closer to 1 MPa. In the lung, they form a continuous network that allows for passive recoil during expiration. However, during pulmonary fibrosis, an increase in collagen content leads to a stiffening of the tissue, which subsequently results in progressive dyspnea (ie. shortness of breath). Thus, increased matrix deposition and altered composition results in altered tissue mechanics that alter cellular behavior and impair tissue function.

The term "acceptable" with respect to a formulation, composition or ingredient, as used herein, means having no persistent detrimental effect on the general health of the subject being treated.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21st ed.; Lippincott Williams & Wilkins: Philadelphia, PA, 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.;

Gower Publishing Company: 2007; *Pharmaceutical Preformulation and Formulation,* 2nd ed.; Gibson Ed.; CRC Press LLC: Boca Raton, FL, 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt is not specifically limited as far as it can be used in medicaments. Examples of a salt that the compounds described herein form with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid: organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer (such as cis- and trans-isomer), or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses.

Also disclosed herein are all suitable isotopic derivatives of the compounds disclosed herein. An isotope derivative of a compound disclosed herein is defined as wherein at least one atom is replaced by an atom having the same atomic number but differing in atomic mass from the atomic mass typically found in nature. Examples of isotopes that can be listed as compounds disclosed herein include hydrogen, carbon, nitrogen, oxygen, fluorine, and chlorine isotopes, such as $^2$H, $^3$H, $^{13}$C, $^{14}$C, $^{15}$N, $^{17}$O, $^{18}$O, $^{18}$F, $^{31}$P, $^{32}$P, $^{35}$S and $^{36}$Cl, respectively. Certain isotopic derivatives of the compounds disclosed herein, such as the radioisotopes of $^3$H and $^{14}$C, are also among them and are useful in the tissue distribution experiments of drugs and substrates. Tritium, i.e., $^3$H, and carbon-14, i.e., $^{14}$C, are easier to prepare and detect and are the first choice for isotopes. In addition, substitution with isotopes such as deuterium, i.e., $^2$H, has advantages in some therapies due to its good metabolic stability, for example, increased half-life in vivo or reduced dosage, and thus priority may be given in some cases. Isotopic derivatives of the compounds disclosed herein can be prepared by conventional procedures, for example by descriptive methods or by the preparations described in the Examples below, using appropriate isotopic derivatives of the appropriate reagents. The term "stable isotopes" refers to those exist stably in nature.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

Adamantane

The adamantane moiety is the structural backbone of many compounds, such as memantine. In some embodiments, the memantine analog is within the adamantane structural class. Adamantane derivatives can be very potent in their respective therapeutic classes. Currently available adamantane derivatives in clinical practice include amantadine, memantine, rimantadine, tromantadine, adapalene, saxagliptin, vildagliptin. Adamantane derivatives have been approved for a wide spectrum of indications, including antivirals, antidiabetics, and against Alzheimer's and Parkinson's disease.

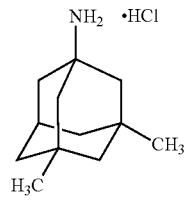

Memantine is a low-affinity voltage-dependent uncompetitive antagonist of the N-methyl-D-aspartate receptors found in nerve cells and is used for the treatment of patients with moderate to severe Alzheimer's disease.

Pharmaceutically Acceptable Salt

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997), which is hereby incorporated by reference in its entirety). In some embodiments, acid addition salts of basic compounds are prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2 dimethylaminoethanol, 2 diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N ethylpiperidine, polyamine resins and the like.

Pharmaceutical Carriers

Prodrug refers to a precursor or derivative form of a pharmaceutically active substance that is less cytotoxic or non-cytotoxic to tumor cells compared to the parent drug and is capable of being enzymatically activated or converted into an active or the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosme and other 5-fluorouridine prodrugs which can be converted into the more active cytotoxic free drug. Examples of cytotoxic drugs that can be derivatized into a prodrug form for use herein include, but are not limited to, those chemotherapeutic agents described above.

Adamantane derivatives, preferably memantine used in the practice of a method of the invention may be formulated into pharmaceutical compositions comprising a carrier suitable for the desired delivery method. Suitable carriers include any material which, when combined with adamantane derivatives, preferably memantine, retains the function of adamantane derivatives, preferably memantine and is non-reactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Therapeutic formulations of adamantane derivatives, preferably memantine are prepared for storage by mixing adamantane derivatives, preferably memantine having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Adamantane derivatives, preferably memantine is administered by any suitable means, including parenteral, subcutaneous, intraperitoneal, intrapulmonary, and intranasal, and, if desired for local treatment, intralesional administration. Parenteral infusions include intravenous, intra-arterial, intraperitoneal, intramuscular, intradermal or subcutaneous administration. In addition, adamantane derivatives, preferably memantine is suitably administered by pulse infusion, particularly with declining doses of adamantane derivatives, preferably memantine. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site.

Compositions of the present invention can be in the form of, for example, granules, powders, tablets, capsules, syrup, suppositories, injections, emulsions, elixirs, suspensions or solutions. The instant compositions can be formulated for various routes of administration, for example, by oral administration, by nasal administration, by rectal administration, subcutaneous injection, intravenous injection, intramuscular injections, or intraperitoneal injection. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

Adamantane derivatives, preferably memantine may be administered in any suitable form, including tablets, liquids, timed release capsules, in the form of sublingual dosing, transepidermal patches, subcutaneous sustained release devices, nasal sprays, rectal suppositories and injections. When a sustained release is desired preferred forms are timed capsules, transepidermal patches, and sustained release devices, such as a biodegradable hydrogel. When a quick response is desired preferred forms are sublingual dosing and injection. For children, geriatric patients, and patients who might have trouble swallowing or compliance problems, preferred forms are rectal suppositories and liquids.

As used herein, "an effective amount" refers to the minimum amount required to reduce the fibrotic tissue of fibromatosis conditions, such as integumentary system fibromatosis conditions. An individual preferably exhibits a reduction in fibrotic tissue after treatment. Those of skill in the art are aware of formulations and methods of administering memantine for the therapeutic intervention of disorders such as Alzheimer's disease (Rive et al., Int J Geriatr Psychiatry. 2004 May; 19 (5): 458-64); vascular dementia (Winblad et al., Lancet Neurol 2002; 1:469); ischemic stroke (Culmsee et al., Stroke. 2004:35:1197:202); Parkinson's disease Merello et al., Clin Neuropharmacol. 1999; 22:273-6); Huntington's disease (Palmer, Curr Drug Targets. 2001; 2:241-71); retinal ganglion injury (Lipton, Surv Ophthalmol. 2003; 48: S38-46); cochlea (Oestreicher et al., ORL J Otorhinolaryngol Relat Spec. 1998:60:18-21); MS-nystagmus in multiple sclerosis (Stark et al., J Neurol 1997; 244:9-16); treatment of severe spastic and extrapyramidal movement disorders in combination with stereotaxic surgery. (Mundinger et al., Nervenarzt. 1985 February; 56 (2): 106-9); drug resistant dyskinesia (Hanagashi et al., Mov Disord 2000; 15:1016-7); painful peripheral neuropathy (Kirby et al., Pain Med 2002; 3:182); modulation of glutamate systems in addiction (Bisaga et al., Psychopharmacology (Berl) 2001; 157:1-10). Each of the foregoing documents is incorporated herein by reference as providing a general teaching of methods and routes of administration of memantine that are well known to those of skill in the art. Memantine is commercially available from Merz Pharma GmbH & Co. KgaA. The commercial formulations are used for the treatment of Alzheimer's disease and are sold as NAMENDA in the United States. In Europe, memantine is available under the commercial name AXURA®. Such formulations may readily be used for use in the treatment of fibromatosis conditions such as Dupuytren's disease.

Alternatively, adamantane derivatives, preferably memantine may be administered on an "as-needed basis". As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution.

Alternatively, sterile oils may be employed as solvents or suspending agents. Preferably, the oil or fatty acid is non-volatile, including natural or synthetic oils, fatty acids, mono-, di- or tri-glycerides. For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Sustained-release preparations may be prepared. Suitable examples of sustained-release preparations include semipermeable matrices of solid hydrophobic polymers containing adamantane derivatives, preferably memantine, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention may be designed to be short-acting, fast-releasing, long-acting, or sustained-releasing as described herein. Thus, the pharmaceutical formulations may also be formulated for initial bolus to sustained-release.

The instant compositions may also comprise, for example, micelles or liposomes, or some other encapsulated form, or may be administered in an extended-release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

Specific dosages maybe adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The compositions of the invention may be sterilized by conventional, well known sterilization techniques. The resulting solutions may be packaged for use or filtered under aseptic conditions and lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride and stabilizers (e.g., 1 20% maltose, etc.). Adamantane derivatives, preferably memantine may also be administered via liposomes, which are small vesicles composed of various types of lipids and/or phospholipids and/or surfactant which are useful for delivery of a drug (such as the antibodies disclosed herein and, optionally, a chemotherapeutic agent). Liposomes include emulsions, foams, micelles, insoluble monolayers, phospholipid dispersions, lamellar layers and the like and can serve as vehicles to target adamantane derivatives, preferably memantine to a particular tissue as well as to increase the half life of the composition. A variety of methods are available for preparing liposomes, as described in, e.g., U.S. Pat. Nos. 4,837,028 and 5,019,369, which patents are incorporated herein by reference.

Liposomes containing adamantane derivatives, preferably memantine are prepared by methods known in the art, such as described in Epstein et al., Proc. Natl. Acad. Sci. USA 82:3688 (1985); Hwang et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

Fibromatosis Diseases and Conditions

Disorders contemplated by the present disclosure to be amenable to treatment with adamantane derivatives, preferably memantine include, but are not limited to, palmar fibromatosis (Dupuytren's disease), plantar fibromatosis (Ledderhose disease), frozen shoulder (adhesive capsulitis), penile fibromatosis (Peyronie's disease), pachydermodactyly, Garrod's knuckle pads, gingival fibromatosis, dermatofibromatosis, neurofibromatosis, nodular fasciitis, elastofibroma, fibrous papule, congenital generalized fibromatosis/infantile myofibromatosis, aponeurotic fibromas, infantile digital fibromatosis, aggressive infantile fibromatosis, fibromatosis colli, dermatofibrosis lenticularis/Buschke-Ollendorf syndrome, scleroderma, localized scleroderma morphed, localized linear scleroderma, systemic scleroderma, graft-versus-host-disease, burn and post-burn skin fibrosis, cutaneous fibrosis, keloids, hypertrophic scarring, desmoid tumor, desmoid fibromatosis, nephrogenic fibrosing dermopathy, mixed connective tissue disease, scleromyxedema (papular mucinosis), scleredema, eosinophilic fasciitis, eosinophilia-myalgia syndrome, ionizing radiation-induced fibrosis, lipodermatosclerosis, collagenomas, diabetic hand (diabetic fibrosis), and nephrogenic systemic fibrosis, pulmonary fibrosis, idiopathic pulmonary fibrosis, and interstitial lung disease, reactive interstitial fibrosis, replacement fibrosis, infiltrate interstitial fibrosis, endomyocardial fibrosis, cardiovascular disease (CVD), heart failure, arrhythmia, valvular disease, vitreous fibrosis, subepithelial fibrosis, macular degeneration, strabismus, chronic kidney disease (CKD), diabetic kidney disease (DKD), progressive kidney disease, non-alcoholic steatohepatitis (NASH), non-alcoholic fatty liver disease (NAFLD), liver cirrhosis, glial scar, spinal cord injury, chronic pancreatitis, pancreatic cancer, Crohn's disease, ulcerative colitis, surgical adhesions, myelofibrosis, chronic myelogenous leukemia, myelodyspastic syndrome, rheumatoid arthritis, systemic lupus erythrematosus, nephrogenic systemic fibrosis, fibrosing hypersensitivity pneumonitis (fHP), idiopathic retroperitoneal fibrosis, and peritoneal fibrosis.

As discussed in the background, there exists a significant need for new therapies for fibromatosis conditions. The present disclosure provides treatment of integumentary system fibromatosis conditions with adamantane derivatives, preferably memantine. In a preferred embodiment, Dupuytren's patients are treated with adamantane derivatives, preferably memantine.

The term "integumentary system" refers to structures such as the epidermis, dermis, and hypodermis. The epidermis is the tough outer layer that acts as the first line of defense against the external environment. It is composed of stratified squamous epithelial cells that further break down into four to five layers. From superficial to deep, the primary layers are the stratum corneum, stratum granulosum, stratum spinosum, and stratum basale. In the palms and soles, where the skin is thicker, there is an additional layer of skin between the stratum corneum and stratum granulosum called the stratum lucidum. The epidermis regenerates from stem cells located in the basal layer that grow up towards the corneum. The epidermis itself is devoid of blood supply and derives its nutrition from the underlying dermis. The dermis is the underlying connective tissue framework that supports the epidermis. It further subdivides into two layers—the superficial papillary dermis and the deep reticular layer. The papillary layer forms finger-like projections into the epidermis, known as dermal papillae, and consists of highly vascularized, loose connective tissue. The reticular layer has dense connective tissue that forms a strong network. The dermis as a whole contains blood and lymph vessels, nerves, sweat glands, hair follicles, and various other structures embedded within the connective tissue. The hypodermis lies between the dermis and underlying organs. It is commonly referred to as subcutaneous tissue and is composed of loose areolar tissue and adipose tissue. This layer provides additional cushion and insulation through its fat storage function and connects the skin to underlying structures such as muscle.

Under normal physiological processes, when the body undergoes trauma with a resulting injury, the integumentary system orchestrates the wound healing process through hemostasis, inflammation, proliferation, and remodeling. Hemostasis occurs through tissue factor located in subendothelial spaces of the skin, which triggers the coagulation cascade to form a fibrin clot. In the following inflammatory phase, immune cells such as neutrophils and monocytes will infiltrate the injury site to attack pathogens and clear out debris. The proliferative phase involves the multiplication of resident cells such as keratinocytes and fibroblasts that contribute to the formation of granulation tissue. Through a matrix of immune cells and the eventual formation of a collagen network by fibroblasts and myofibroblasts, the new extracellular matrix forms. The final remodeling phase consists of apoptosis as cells are no longer needed and excess structures are broken down in efforts to restore the original architecture. Macrophages secrete matrix metalloproteases that remove excess collagen, and remaining immature collagen matures to finalize the extracellular matrix.

Expansion of fibrous connective tissue and abnormal deposition of extracellular matrix (ECM) are at the basis of many fibrotic diseases. Fibrosis may occur as the formation of excessive fibrous connective tissue as a result of chronic inflammation, tissue damage/remodeling (for instance, following chemical or radiation therapy), persistent infections, autoimmune disease, allergic responses and cancer. During this process excessive extracellular matrix (ECM) components, including collagens, are deposited and accumulate. If progressive, fibrosis can become chronic, and can ultimately lead to organ failure and even death. A fibrotic process may entail the activation of fibroblasts into myofibroblasts, cells that acquire a stellate or spindle-shape morphology, are motile and contractile, express α-smooth muscle actin, and secrete/remodel the ECM, altering the stiffness, morphology and composition of the tissue. In the skeletal muscle under healthy conditions fibrosis may occur in the form of scar tissue during the healing process following muscle injury. This may be associated with infiltration of inflammatory cells that induce satellite cells to proliferate and differentiate into new myotubes and myofibers while simultaneously the ECM undergoes remodeling. In disease conditions, such as muscular dystrophies or myopathies, progressive expansion of the connective tissue and abnormal deposition of ECM components, consequent to myofiber degeneration, may ultimately result in full-blown fibrosis.

Despite this variety of causes and disease-specific pathophysiologic processes leading to fibrosis, the cellular and molecular mechanisms of excessive extracellular matrix accumulation in the tissues may be similar. Extensive research in the mechanisms of dermal, pulmonary, hepatic, and renal fibrosis revealed similarities between the molecular and cellular mechanisms of fibrosis and wound healing.

Dupuytren's Disease

Dupuytren's disease, also called Dupuytren's contracture, is an abnormal thickening and tightening of the normally loose and flexible tissue beneath the skin of the palm and fingers, called fascia. The fascia contains strands of fibers, like cords, that run from the palm upward into the fingers. In Dupuytren's disease, these cords tighten, or contract, causing the fingers to bend toward the palm of the hand, or curl forward. Affected fingers may not straighten completely. In severe cases, crippling hand deformities may occur. In addition to issues with the fingers, people with Dupuytren's disease may also experience symptoms in the affected hand such as inflammation or swelling, tenderness, pain or burning, and itching. The condition may gradually get worse with time. Dupuytren's disease most often affects the two fingers farthest from the thumb. It can often occur in both hands, although one may have worse symptoms than the other.

The signs of Dupuytren's disease can show up in phases. Nodules, or lumps under the skin in the palm of the hand are the first symptoms for many people. The lump may feel tender and sore at first, but this discomfort may eventually go away. The nodules cause tough bands of tissue to form under the skin in the palm. These inflexible bands can cause the fingers to bend, or "curl," forward toward the wrist, sometimes severely. As the curling gets worse, it may become difficult, if not impossible, to straighten the fingers. People with Dupuytren's disease often have a hard time picking up large objects, placing their hands into their pockets, placing their hand flat on a table, putting on gloves or shaking hands, which can complicate everyday activities.

Currently, there is no cure for Dupuytren's disease. There are no approved pharmacologic treatments to slow or delay progression of the disease. Radiation in early stages of the disease may relieve symptoms and slow the progression of the worsening of the disease. Surgery is generally an acute fix with limited durability due to immune response, complications, and frequent adverse events. Treatment for Dupuytren's disease may involve breaking apart or removing the cords that pull the fingers towards the palm. Choice of the procedure depends on the severity of symptoms.

Fasciectomy may be the most common treatment worldwide. It involves surgical removal of affected tissue. The procedure divides the thick cord of ligament tissue so the affected finger can move more freely. There can be a 22-40% recurrence after treatment, and in some patients, disease activation occurs. Significant complications and long recovery times may be risks of the procedure. Repeat surgery can worsen outcomes and leads to risks of complications, including amputation.

Needle fasciotomy consists of surgical perforation of diseased tissue to break the cord. Although it may be an effective treatment, there is a 50-85% disease recurrence after the procedure. A reduced effect of the procedure may occur after subsequent treatments. Only a limited number of trained surgeons can perform.

Collagenase injection is an FDA approved treatment for Dupuytren's disease. Collagenase injection, or enzymatic fasciotomy, is a multi-day procedure in which collagenase is injected by a health care provider, followed by physical hand manipulation. This treatment may be used if fingers are already bent. The enzymes in the injection can help dissolve the thick and tight tissue, which can weaken the tight bands and may allow a doctor to stretch the tightened area. This treatment can result in modest benefit with multiple short-term side effects, including bruising and swelling. There may be a 50-70% disease recurrence rate, and the treatment is only available in the U.S., only for patients with contracture and cord.

Steroid injections may be given to help relieve pain from nodules and may help to soften and flatten hard lumps. In some cases, steroid injection may prevent finger contractures from getting worse, but will not straighten the finger if it already has a contracture. A series of shots may be needed to see long term results.

Radiotherapy consists of treatment of targeted low dose radiation of fibrotic areas. Radiotherapy has the potential to reverse node size but does not reverse contractures. It has high cost and limited coverage, and limited patient access to specialists. It is an option only in early disease, is not available to retreat areas, and radiation concerns limit the use of treatment.

Surgical removal of diseased tissue may be performed in cases of severe symptoms. In some severe cases, all tissues affected by Dupuytren's disease are removed, including the attached skin, and a skin graft is used to cover the open wound. This usually results in a more complete and longer lasting release but has the longest recovery time. Contracture of the fingers often recurs over time.

Ledderhose Disease

Ledderhose disease, also called plantar fibromatosis, is a rare disease affecting the plantar fascia, which is the thick layer of tissue that protects and supports the bottom of the foot. There are three stages to Ledderhose disease. In the first stage of Ledderhose disease there is an increase in the number of cells in the area. In the second stage of Ledderhose disease, small, hard nodules develop on the bottom of the feet. The nodules are benign thickening of the plantar fascia, that can look like bumps, knots, or growths on the surface of the skin. The nodules may grow to be 1 to 2 centimeters in size. In the last stage of Ledderhose disease the tissue contracts, in some cases, the toes may contract, or curl down. Symptoms of Ledderhose disease may include pain and swelling in the foot, difficulty walking, a small collection of bumps on the bottom of the foot, and toes that may curl. The pain that occurs in the bottom of the feet and toes in Ledderhose disease can affect the way a person walks. As a result, the person may change the way they naturally walk to offset the pain. This may put too much pressure on other parts of the feet and ankles, which may cause additional injuries. In 25% of cases, Ledderhose disease affects both feet. Treatment for Ledderhose disease may include orthotics, massage, stretching, ice, and medications such as intralesional steroids, verapamil, imatinib, radiation therapy, extracorporeal shock wave therapy, tamoxifen, sorafenib, mitomycin C, collagenase injection, and surgery.

Adhesive Capsulitis

Frozen shoulder, or adhesive capsulitis is a painful condition in which shoulder movement becomes limited. Frozen shoulder may occur when the strong connective tissue surrounding the shoulder joint becomes thick, stiff, and inflamed. The joint capsule contains the ligaments that attach the top of the upper arm bone to the shoulder socket, firmly holding the joint in place. In frozen shoulder, the more pain a person feels, the less likely they will use their shoulder. Frozen shoulder can occur when inflammation causes the shoulder joint capsule to thicken and tighten. Thick bands of scar tissue called adhesions develop over time, and there is less synovial fluid to keep the shoulder joint lubricated. Lack of use can cause the shoulder capsule to thicken and become tight, and can make the shoulder even more difficult to move and rotate and be "frozen" in its position. Healthcare professionals divide frozen shoulder symptoms into three stages. In the freezing stage, the shoulder may become stiff and painful to move. The pain may slowly increase and may worsen at night. Inability to move the shoulder may increase. This stage may last from six weeks to nine months. In the frozen stage the pain may lessen, but the shoulder may remain stiff, making it more difficult to complete daily tasks and activities. This stage may last for two to six months. In the thawing stage pain may lessen and the ability to move the shoulder may slowly improve. Full or near full recovery may occur as typical strength and motion returns. This stage may last from six months to two years. Treatment for adhesive capsulitis may include hot and cold compresses, ibuprofen, acetaminophen, steroid injection, physical therapy, exercise, and transcutaneous electrical nerve stimulation.

Scleroderma

Scleroderma is a long-lasting disease that affects the skin, connective tissue, and internal organs. In scleroderma, the immune system may cause the body to make too much collagen. As a result, skin gets thick and tight, and scars can form on the lungs and kidneys. Blood vessels may thicken and stop functioning normally, which may lead to tissue damage and high blood pressure. Localized scleroderma mainly affects the skin. It occurs in two forms: morphea and linear. In morphea scleroderma, or generalized morphea hard, oval shaped patches may occur on the skin. These patches may start out red or purple and then turn whitish in the center. This type can affect blood vessels or internal organs. In linear scleroderma lines or streaks of thickened skin may occur on the arms, legs, or face. Systemic scleroderma, or generalized scleroderma, can involve many body parts or systems. There are two types of systemic scleroderma: limited and diffuse. In limited scleroderma symptoms may come on slowly and the skin of the face, hands, and feet may be affected. It can also damage the lungs, intestines, or esophagus. In diffuse scleroderma symptoms may come on quickly. Skin on the middle part of the body, thighs, upper arms, hands, and feet may become thick. Internal organs such as the heart, lungs, kidneys, and gastrointestinal tract may be affected.

Some types of scleroderma can cause severe complications, including kidney failure, pulmonary hypertension, pulmonary fibrosis, cardiovascular disease, congestive heart failure, immunodeficiency, gastrointestinal diseases, and cancer. Treatments for scleroderma may include topical skin treatments, immunosuppressants, medicines to manage symptoms, antifibrotics, anti-inflammatory drugs, physical therapy, light therapy, and stem cell transplants. FDA approved treatments for scleroderma include privigen, nintedanib, and Actemra.

Keloids

A keloid scar is a thick raised scar. It can occur wherever there is a skin injury but usually forms on earlobes, shoulders, cheeks, or the chest. In people who are prone to keloids, they may get keloids in more than one place. A keloid scar may form within months to years of the inciting injury. Keloids likely develop due to a dysfunction of the wound-healing process. Keloids are typically characterized by significant fibrosis and an intensive inflammatory response. Collagen is a protein found throughout the body and is useful to wound healing, however, when the body produces too much collagen, keloids may form. Collagen is thicker than the rest of the skin. This thicker, less flexible tissue may become a scar. With keloids the extra connective tissue that forms may extend beyond the original wound area. Signs and symptoms may include thick, irregular scarring, typically on the earlobes, shoulders, cheeks or middle chest, shiny, hairless lumpy, raised skin, varied size, depending on the size of the original injury and when the keloid stops growing, varied texture, from soft to firm and rubbery, reddish, brown or purplish, depending on the skin color, itchiness, and discomfort. When a keloid is located on a joint, it may develop hard, tight tissue that restricts movement. Keloid scar treatment may include wound care, corticosteroid cream, injected medication, freezing the scar, laser treatment, radiation therapy, and surgical removal. There are no FDA approved drugs to treat keloids.

Hypertrophic Scarring

A hypertrophic scar is a thick raised scar. A hypertrophic scar is an abnormal response to wound healing in which extra connective tissue forms within the original wound area. This may result in a raised scar. Typically, a small wound to the top layer of the skin heals as new skin forms as the wound heals. When wounds extend deeper into the dermis layer and lower, the body may respond by making collagen to repair the wound. Collagen is thicker than the rest of the skin. This thicker, less flexible tissue may become a scar. Wounds go through three phases of healing: inflammation, proliferation, and remodeling. Scar tissue forms during the remodeling phase. Specific types of cells such as fibroblasts and myofibroblasts and certain signaling molecules such as transforming growth factor-beta and tumor necrosis factor are all involved in wound healing and the creation of new tissue. In hypertrophic scars this repair response goes haywire. The result is the abnormal production of extra collagen and a decrease in elastin, which may lead to thick, raised stiff scars.

While most scars are flat, in hypertrophic scars, the body makes extra collagen that may result in a raised scar. Raised scars can be either a hypertrophic scar or a keloid. In hypertrophic scars the extra connective tissue that forms stays within the original wound area. Hypertrophic scars more commonly occur in taut skin areas such as the back, chest, shoulders, upper arms, elbows and other joints following skin trauma, burns, or surgical incisions. However, hypertrophic scars can occur anywhere on the skin where an injury or wound occurs. Hypertrophic scars can cause pain or itching. If they form over a joint, hypertrophic scars can limit movement. Signs and symptoms of hypertrophic scars may include hard or thickened raised tissue over the wound site, pink to red to purple skin color over the wound site, scar appears most commonly on the upper trunk of the body and skin that covers the joints, scar that develops one to two months after injury, scar that causes irritation, itching, tenderness, and pain, scar on the skin or over a joint that may limit the joint's natural movement. Treatment options for hypertrophic scars may include corticosteroid injections, laser therapy, bleomycin or fluorouracil injection, cryotherapy, surgery, silicone gel, moist dressing with pressure garment. There are no FDA approved treatments for hypertrophic scars.

Diabetic Fibrosis (Diabetic Hand)

Diabetic hand syndrome, or diabetic fibrosis, also called limited joint mobility, or diabetic cheiroarthropathy, is stiffness of the joints most often affecting the small joints of the hands. In diabetic fibrosis the skin on the hands may become waxy and thickened. Eventually finger movement can be limited. Other joints can be affected, including the shoulders, feet, and ankles. In diabetic fibrosis it may be difficult to extend the fingers or press the palms together flat. Treatment for diabetic fibrosis may include better management of blood sugar levels and physical therapy, which may slow the progress of the condition. However, the limited movement may not be reversible.

Diabetic fibrosis can be a complication of diabetes. Patients with long-standing diabetes may exhibit extensive fibrosis and organ dysfunction. Metabolic dysregulation may be observed in people with diabetes which may directly activate a fibrogenic program causing tissue injury and organ dysfunction. Inappropriate, excessive, or prolonged activation of resident fibroblasts within organs may promote matrix deposition, stimulating tissue fibrosis and causing organ dysfunction. In diabetes, metabolic dysregulation may stimulate activation and expansion of resident fibroblasts populations in several different organs. Hyperglycemia and insulin resistance may be the fundamental metabolic perturbations that can trigger fibrogenic cascades in diabetic subjects.

Nephrogenic Systemic Fibrosis

Nephrogenic systemic fibrosis is a rare disease that occurs mainly in people with advanced kidney failure with or without dialysis. Nephrogenic systemic fibrosis may resemble skin diseases, such as scleroderma and scleromyxedema, with thickening and darkening developing on large areas of the skin. Nephrogenic systemic fibrosis can also affect internal organs, such as the heart and lungs, and it can cause a disabling shortening of muscles and tendons in the joints, or joint contracture. Nephrogenic systemic fibrosis can begin days to months, and even years, after exposure to an older gadolinium-based contrast agent (group 1). Some signs and symptoms of nephrogenic systemic fibrosis may include swelling and tightening of the skin, reddened or darkened patches on the skin, thickening and hardening of the skin, typically on the arms and legs and sometimes on the body, but almost never on the face or head, skin that may feel "woody" and develop an orange-peel appearance, burning, itching, or severe sharp pains in areas of involvement, skin thickening that inhibits movement, resulting in loss of joint flexibility, blisters or ulcers. In some people, involvement of muscles and body organs may cause muscle weakness, limitation of joint motion caused by muscle tightening (contractures) in arms, hands, legs, and feet, bone pain, particularly in the hip bones or ribs, reduced internal organ function, including heart, lung, diaphragm, gastrointestinal tract or liver, and yellow plaques on the sclera of the eyes. Nephrogenic systemic fibrosis is generally long term. In a few people, it can cause severe disability, even death. There is no treatment that is consistently successful in halting or reversing the progression of the disease.

Peyronie's Disease

Peyronie's disease, or penile fibromatosis, occurs when scar tissue, called plaque, forms inside the penis, which can cause a bent, rather than straight, erect penis. The fibrosis plaque may start after trauma that causes bleeding inside the penis. In other cases, which develop over time, may be linked to genes, however, in some, both injury and genes may be involved. Symptoms of Peyronie's disease may develop slowly or appear overnight. When the penis is soft, the condition may not be apparent, but in severe cases, hardened plaque may hamper flexibility, causing pain and forcing the penis to bend or arc when erect. The pain may ease over time, but the bend in the penis can worsen.

The primary symptom of Peyronie's disease is a curve or bend in the penis. It may be possible to feel scar tissue under the skin. Other symptoms of Peyronie's disease may include loss of length in the penis, loss of girth in the shaft of the penis, which may look like an indent or have an hourglass shape, lumps in the penis, painful erections, softer erections, difficulty engaging in intercourse, or pain while having sex. There are two stages of Peyronie's disease. In acute Peyronie's disease a scar forms under the skin of the penis, causing it to curve or change its shape another way. It may be painful when the penis is erect or flaccid. The acute stage can last between six and twelve months. In chronic Peyronie's disease the scar is no longer growing and the curvature may not worsen. Pain usually goes away during the chronic phase, but it can sometimes continue, especially if there is an erection. Erectile dysfunction may develop during this phase. Some men with the condition may develop scar tissue elsewhere in the body, such as on the hand or foot. Men with Dupuytren's disease may be more likely to develop Peyronie's disease. Most men with Peyronie's disease can still have sex. For some, it can be painful and cause erectile dysfunction. Available treatments may include traction therapy, medications including verapamil and interferon, and surgery for severe cases. The only FDA-approved medication for Peyronie's disease is collagenase clostridium histolyticum.

Desmoid Tumor

Desmoid tumors, or desmoid fibromatosis, (also called aggressive infantile fibromatosis) develop in the fibrous tissue that makes up tendons and ligaments. Desmoid tumors are usually considered benign because they rarely spread to different parts of the body. Aggressive desmoid tumors that grow fast can be like cancer in some ways. They can grow into nearby tissues and can be fatal. Types of desmoid tumors may include abdominal wall desmoid tumors, intra-abdominal desmoid tumors, and extra-abdominal desmoid tumors. Symptoms of desmoid tumors may include pain, soreness, or a tingling sensation from a tumor pressing on nearby nerves, organs or blood vessels, a lump or swollen area, usually in the arms, legs and abdomen, trouble moving an arm or leg, or nausea and vomiting from a tumor in the abdomen. Desmoid tumors may occur in the abdomen or colon and may be linked to pregnancy due to high levels of estrogen and to some kinds of severe injuries. If desmoid tumors are close to the surface of the skin, they can be painless or a slightly painful lump. If desmoid tumors are in the abdomen, they can be more aggressive. The tumor may press against blood vessels and nerves and cause pain, a limp, or problems using legs, feet, arms, or hands. The tumor can also block the colon or grow into nearby tissues. This may cause severe pain, bleeding from the rectum, and other health problems. Treatment for desmoid tumors may include active surveillance, targeted therapy, cryoablation, chemotherapy, hormone therapy or surgery. The only FDA approved treatment for desmoid tumors is nirogacestat.

Knuckle Pads

Knuckle pads are benign or noncancerous growths that form on the joints of the fingers or toes. Knuckle pads may cause an unpleasant appearance of the hands. Knuckle pads may be painful or tender. If knuckle pads become large, they may make it more difficult for some people to use their hands. Knuckle pads may cause discomfort or rubbing on the toes and feet. Knuckle pads are a type of fibromatosis which causes noncancerous tumors under the skin. If a person has knuckle pads, they may notice bumps on the knuckles or joints of the fingers or toes which are skin colored, solid and firm, and painless, although they can cause pain or tenderness in some cases. Knuckle pads may appear like corns and callouses, which are thickened, rough areas of skin. However, knuckle pads are dense tissue that forms under the skin. Treatment for knuckle pads can be employed if appearance or symptoms of knuckle pads are bothersome, and may include topical medications, steroid injections, and surgery.

Nodular Fasciitis

Nodular fasciitis, also called pseudosarcomatous fasciitis, proliferative fasciitis, or infiltrative fasciitis, is a fast-growing fibrous lump in the soft tissue that is noncancerous. The connective tissue, or fascia, just under the skin that holds all the muscles, veins, organs, bones, and nerves in place may become inflamed and genetic changes can cause uncontrolled cell growth leading to a lump. Nodular fasciitis may occur in which a lump grows into the fascia. The tumors can also grow in places without fascia, including in the muscle, space between the muscles, blood vessels, and skin. Growths can occur anywhere on the body but may be most common in the upper body, including the neck, head, arms, hands, legs, or torso. Nodular fasciitis may cause a lump under the skin that can be felt when the skin is palpated. Typically, nodular fasciitis appears as a single lump in one body area that may be smaller than 4 centimeters. These lumps can grow quickly and may grow as large as 12 centimeters. Lumps may be firm, rubbery, solid, or tender or painful to touch. In some cases, the lump may press against nerves which may cause loss of sensation in the affected body area, temporary paralysis, or tingling. Nodular fasciitis may not require treatment and in some cases, the lump may go away on its own. However, if the lump causes pain or other symptoms it may be surgically removed.

Elastofibroma

Elastofibroma is a rare, benign, slow-growing fibrous connective tissue tumor that occurs most often in the subscapular area. Elastofibroma can be characterized by accumulated abnormal elastic fibers and is generally regarded as a reactive process. People with an elastofibroma often have a long history of swelling and occasionally have pain and discomfort. Elastofibromas may occur on both sides of the subscapular area, however an elastofibroma may occur on the foot, hand, thigh, olecranon, GI tract, subungal, trachea, dorsal spine, eye, or soft palate. Elastofibromas may appear as large, well-circumscribed tumors that do not adhere to the overlying skin. An elastofibroma may be several centimeters in length. Elastofibromas usually do not cause pain, however, some people may experience stiff shoulders, local pain with arm movement, or a click sound that occurs with shoulder motion. Treatment for elastofibromas may include non-surgical management or surgery.

Nephrogenic Fibrosing Dermopathy

Nephrogenic fibrosing dermopathy (NFD) is an acquired, idiopathic, chronic, progressive eruption of the skin sometimes accompanied by systemic fibrosis that occurs in the context of renal failure. Even in the setting of renal disease, NFD may occur rarely and its cause is unknown. People with NFD may have hard, indurated, sometimes peau d'orange plaques. They often show a distinctive physical appearance, with elbows and knees angled inward, and people with NFD may experience a loss of range of motion. Histology of NFD may demonstrate thickened collagen bundles with surrounding clefts, mucin, and a proliferation of fibroblasts and elastic fibers, sometimes with reticular, dermal, large epithelioid or stellate spindle cells. The fibrosis process of NED can affect the internal organs, which may be caused by circulating fibrocytes. Rare cases of partial-to-complete spontaneous resolution have been reported in the absence of specific therapy. Treatments for NDF may cause inconsistent results and may include restoration of renal function, extracorporeal photopheresis, photodynamic therapy, high-dose intravenous immunoglobulin, and other immunosuppressive therapies.

Mixed Connective Tissue Disease

Mixed Connective Tissue Disease (MCTD) is a rare autoimmune disorder that can show the features of three different connective tissue disease types: Systemic Lupus Erythematosus, Scleroderma, and Polymyositis. MCTD symptoms may not all show up at the same time but can appear over several years. Symptoms can vary from person to person, but can include pain or inflammation in joints, muscle weakness, fever, and fatigue or tiredness. Hands can become puffy and swollen due to fluid buildup. Skin rashes, red-colored patches on knuckles, and violet coloring of eyelids may occur. Hair loss may occur. A condition called periungual telangiectasia, where small blood vessels around the fingernails become dilated may occur. Abnormalities in the esophagus can cause hypomotility, where the contractions that move food down the esophagus are irregular or absent may occur. Abnormalities in the lungs can cause pulmonary hypertension. Heart conditions such as pericarditis, myocarditis, and aortic insufficiency may develop. Kidney disease may occur. Blood disorders such as anemia and leukopenia may occur. Neurological abnormalities may develop. Lymph nodes, spleen, and liver may become enlarged. Intestines may also be affected.

MCTD may be the result of a combination of connective tissue diseases. Treatment can vary depending on the type of connective tissue diseases present and can vary depending on the type of connective tissue diseases the person has, how severe they are, and how quickly the condition advances. There is no known cure for the condition, but MCTD treatments can help manage its signs and symptoms. Medications used for treating MCTD may include corticosteroids, hydroxychloroquine, nifedipine, amlodipine, immunosuppressants, bosentan, sildenafil, ibuprofen, or naproxen.

Scleromyxedma (Papular Mucinosis)

Scleromyxedema is a rare, severe skin disorder. Signs and symptoms may include abnormal accumulation of mucin in the skin (mucinosis), causing papular and sclerodermoid bumps; increased production of fibroblasts (connective tissue cells) in the absence of a thyroid disorder; and monoclonal gammopathy (abnormal proteins in the blood). It often involves internal organs and may affect various body systems. Symptoms of scleromyxedema may include generalized abnormality of the skin, papules, facial abnormality, abnormality of the forearm, glabella, hand, or neck, joint pain, difficulty swallowing, muscle pain, muscle weakness, localized thickening and tightness of the skin of the fingers or toes, stiff skin, thickened skin, abnormal lung morphology, skeletal muscle, cardiovascular system, gastrointestinal tract, or kidney, shortness of breath upon physical activity, encephalopathy, gastroesophageal reflux, hypoperistalsis, narrow mouth, itching, or seizure. Treatment for scleromyxedema may include lenalidomide, bortezomib, and dexamethasone, however, no standard treatment exists.

Cutaneous Fibrosis

Cutaneous fibrosis is the accumulation of extracellular matrix (ECM) components in the dermis, leading to compromised function and altered architecture of the dermis. Cutaneous fibrosis involves the proliferation of fibroblasts and collagen fibers in the dermis or around hair follicles. In more severe cases, the fibrosis can extend deeper into the dermis and subcutaneous tissue. Areas of fibrosis may appear slightly basophilic compared to the non-fibrotic dermis. The appearance can vary based on staining quality and the maturity of the fibrotic lesion. In early stages, fibrosis is often accompanied by inflammatory cells, especially when associated with an epidermal ulcer. Fibroblasts tend to be larger and more active, and collagen fibers are less compact and more disorganized. As fibrosis progresses, fibroblasts may become smaller and more spindle-shaped. Collagen fibers may become more organized and compact, and inflammation may tend to decrease. Cutaneous fibrosis can result from suboptimal wound healing following significant tissue injury such as severe burns, trauma, and major surgeries.

Scleredema

Scleredema is an uncommon fibromucinous connective-tissue disease. It can be characterized clinically by woody induration and hardening of the skin that results from excessive mucin deposition between thickened collagen bundles in the dermis. There are three clinical forms of scleredema, which are classified by their associated condition. Scleredema may be associated with a history of an antecedent infection (type 1), a blood dyscrasia (type 2), or diabetes mellitus (type 3). Each of these clinical forms may have a different history, course, and prognosis. Scleredema can be a self-resolving or a persistent skin condition. It is typically considered benign, but it can involve internal organs and rarely may result in death. There is no standard therapeutic protocol nor established effective treatment for the treatment of scleredema.

Dermatofibroma

A dermatofibroma is a noncancerous skin growth, or tumor. Dermatofibromas may appear as firm bumps, or nodules. Usually, dermatofibromas are superficial and grow on the top layer of skin, or on the epidermis, and may often form on the arms or legs. Dermatofibromas may feel firm to the touch and can be itchy, tender or painful. About 3 in every 100 skin lesions is a dermatofibroma. About 1 in 5 people who have a dermatofibroma may have had an injury or wound where the tumor forms. Sometimes, a dermatofibroma can develop spontaneously, for no known reason. Because dermatofibromas are often noncancerous, treatment is not always indicated. If a dermatofibroma is large or causes discomfort, a healthcare provider may remove it.

Eosinophilic Fasciitis

Eosinophilic fasciitis (EF) (also known as Shulman's syndrome) is a rare condition that causes the fascia, or the layer of tissue under the skin that covers the muscles, to swell and thicken quickly. Over time, the fascia may thicken and expand, which can make it difficult to move the skin and muscles around it. If it is not treated, EF can freeze the fascia in place. This is called contracture. EF is a type of autoimmune disease, which, if not treated or diagnosed quickly, can cause chronic skin changes and limited joint range of motion. EF can cause inflammation in fascia located anywhere in the body, but it most commonly affects the arms, legs, or joints around them. EF can also affect the skin on the face, chest, and abdomen.

EF is an idiopathic fibrotic disorder with the histopathologic hallmark of fascial fibrosis. Some people with EF may also develop inflammation of the joints similar to rheumatoid arthritis. Uncontrolled joint inflammation can damage joint cartilage and can lead to chronic arthritis. If the fascia in the hand or wrist is affected by EF, the inflammation can put pressure on the median nerve and cause carpal tunnel syndrome. People may notice symptoms of EF such as pain or swelling after intense physical activity. Symptoms of EF may include muscle pain, areas of tender skin, inflammation or swelling, carpal tunnel syndrome, arthritis, skin that looks or feels thicker than usual, and puckered skin. EF may be treated with corticosteroids, non-steroidal anti-inflammatory drugs, immune system suppressing medications, physical therapy and surgery.

Eosinophilia-Myalgia Syndrome

Eosinophilia-myalgia syndrome (EMS) is a rare condition that affects the muscles, skin, and lungs. EMS is a type of eosinophilia, which is a condition that causes white blood cells called eosinophils to collect in the blood and tissues. The pathogenesis of EMS likely involves acute inflammation, activation of innate immune pathways, and eosinophil activation, followed by chronic tissue fibrosis. Common symptoms of EMS may include muscle pain, a skin rash, and breathing problems. Severe symptoms can be life-threatening, or may cause severe pain that can prevent a person from completing their daily activities. The symptoms usually develop quickly and can target several parts of the body as a result of eosinophils building up in the blood and tissues. These eosinophil cells can create inflammation, which can cause symptoms including fatigue, fever, swelling of the arms and legs, numbness in the hands and feet, difficulty remembering or trouble concentrating, mood or behavior changes, nausea or vomiting, and diarrhea. Symptoms can also affect the muscles, skin, heart, and lungs.

EMS symptoms may affect muscles and joints, including pain, aches, spasms, weakness, and loss of function in muscles or joints. Pain may range from mild to severe and pain may become progressively worse over several weeks. Skin symptoms can last for three to six months and may include a skin rash, itchy skin, patches of skin with hair loss, and thick patches of skin, or eosinophilic fasciitis. Symptoms that affect the lungs could be mild or severe, and can include coughing, difficulty breathing, shortness of breath, chest pain, irregular heartbeat, and heart muscle inflammation, or myocarditis. Treatment for EMS may include medications such as muscle relaxants, pain relievers, diuretics, and corticosteroids.

Lipodermatosclerosis

Lipodermatosclerosis, also known as sclerosing panniculitis and hypodermitis sclerodermaformis, is a chronic inflammatory condition characterized by subcutaneous fibrosis and hardening of the skin on the lower legs. Lipodermatosclerosis is an inflammatory skin condition which may result from underlying venous insufficiency, which may be caused by incompetent venous valves, venous outflow obstruction, or dysfunction of the calf muscle pump. The resulting venous hypertension may cause an increase of leukocytes within the veins, which then migrate into surrounding tissue. The leukocytes become activated, attracting and releasing proinflammatory cells and cytokines, inducing a chronic inflammatory state. Increased collagen production may lead to the fibrosis of subcutaneous fat.

Acute lipodermatosclerosis may mimic cellulitis, with induration, erythema, pain, itch, aching, and a feeling of swelling or heaviness in one or, more often, both lower limbs. Induration, erythema, and pain may continue in the chronic phase of lipodermatosclerosis. Subcutaneous fibrosis may result in significant narrowing of the distal lower limb, causing the leg to have an 'upside-down champagne bottle' appearance. Other clinical features of chronic venous insufficiency may be present, including hyperpigmentation of the skin from haemosiderin deposition, atrophie blanche, varicose veins, venous eczema, and venous ulcers. Lipodermatosclerosis may be associated with poor wound healing because of the chronic inflammatory state and fibrosis. Venous ulcers commonly co-exist and may be difficult to treat. Treatment for lipodermatosclerosis may include physical activity, compression therapy and elevation, medical treatment, or surgical treatment.

Collagenomas

Collagenomas are an uncommon skin lesion that occur when the deeper layers of the skin do not develop correctly or the components of the layers occur in the wrong proportion where there is too much collagen. Accumulation of collagen can be the major pathologic feature in collagenomas. Collagenomas include familial cutaneous collagenoma, isolated collagenomas, or shagreen patch. Familial cutaneous collagenoma lesions usually appear during adolescence and may be characterized by multiple hard nodules of varying sizes over the upper back. They are sometimes associated with cardiac disease. Shagreen patch may be commonly associated with tuberous sclerosis. These are flesh colored 'orange peel' textured lesions of varying sizes, which are usually found on the back and neck.

Pachydermodactyly

Pachydermodactyly is a benign digital fibromatosis presenting as a progressive asymptomatic periarticular thickening, most commonly around the proximal interphalangeal joints. Pachydermodactylyl may affect the second, third, and fourth fingers of both hands. The thumbs and fifth fingers may be rarely involved. Movement of the fingers may not be restricted. Pachydermodactyly may not be associated with symptoms of pain or stiffness. The toes of a person who has pachydermodactyly may not be affected. Pachydermodactyly may occur in the palmar and distal interphalangeal or metacarpophalangeal joints. Pachydermodactyly may occur due to deposition of abnormal collagen in the dermis, especially loose strands of type III and type V collagen. Treatment for pachydermodactyly may include intralesional corticosteroid or surgical resection.

Gingival Fibromatosis

Gingival fibromatosis is a rare condition in which accumulation of ECM components causes slowly progressive enlargement of the gingiva. Gingival fibromatosis may be generalized or localized to one or more quadrants. Localized gingival fibromatosis may involve the maxillary tuberosities or the facial gingivae in the mandibular molar regions. The onset of enlargement may coincide with eruption of the deciduous or permanent dentition. With progression, the gingival tissue may cover all or part of the tooth crowns and displace teeth. A person who has gingival fibromatosis may develop problems with mastication, speech, or aesthetics. In gingival fibromatosis, the gingiva typically may be firm, normal in color, nonhemorrhagic, and smooth or finely stippled. However, it may appear erythematous if there is superimposed inflammation due to plaque accumulation. Usually, there is involvement of the free and attached gingivae without extension beyond the mucogingival junction. Treatment of gingival fibromatosis may include professional prophylaxis and oral hygiene reinforcement to minimize exacerbation by plaque-related gingival inflammation. For severe cases, surgical removal of excess gingival tissue may be performed. There may be a high risk for recurrence in tooth-bearing areas, and gingivectomy may be combined with selective tooth extraction. In addition, orthodontic and prosthodontic treatment may be needed.

Neurofibromatosis

Neurofibromatosis is a group of neurological and genetic conditions. Neurofibromatosis may cause symptoms that may affect the brain, spinal cord, nerves and skin. Symptoms may vary and depend on the neurofibromatosis type but can include birthmarks and the growth of usually noncancerous tumors. Neurofibromatosis may appear differently for each person with the condition. Small, round bumps may form on the skin. Some people with neurofibromatosis may have more than two of these small bumps or one larger skin growth that forms from multiple nerves under the skin, called plexiform neurofibroma. Some people with neurofibromatosis may have multiple café au lait spots which are flat, light-to-dark brown birthmarks on the skin that range in size and shape. Some people with neurofibromatosis may develop freckles which appear as small, red-to-brown dots in the armpits and groin area.

There are three types of neurofibromatosis, neurofibromatosis type 1, neurofibromatosis type 2, and schwannomatosis. Neurofibromatosis type 1 causes café au lait spots, nerve tumors, or neurofibromas, armpit and groin freckles, eye nerve tumors and bone deformities. Neurofibromatosis type 2, or NF2, also called NF2-related schwannomatosis, causes slow-growing nerve tumors, hearing changes, vision changes, and numbness or weakness. Schwannomatosis is the least common type of neurofibromatosis. Some cases of schwannomatosis do not cause symptoms. In other cases of schwannomatosis the condition can cause slow-growing nerve tumors, or schwannomas sometimes located only on one part of the body, chronic pain, numbness and tingling in the fingers and toes. Symptoms of neurofibromatosis may vary by type; some types do not cause symptoms and others may cause severe symptoms. The most common symptoms of all types include tumors and skin growths. The tumors may grow slowly and may be benign but some can turn into cancer. Other signs and symptoms may include hearing or vision loss, spine curvature, muscle weakness, numbness or tingling, pain and headaches, behavioral changes, learning difficulties, and seizures. Treatment for neurofibromatosis may include tumor removal, medications, surgery, chemotherapy, and radiation therapy. FDA approved treatment for neurofibromatosis type one may include selumetinib.

Fibrous Papule

Fibrous papules are benign growths that show as hard nodules on the sides of the nose or on the wings of the nostrils. Fibrous papules may appear as one papule, although there might be several at the same time. Affected areas such as the face and neck, as well as the lip and forehead, can develop fibrous papules. A fibrous papule is often shaped like a little dome, however, it can occasionally grow up like a wart in progress. The papules may be hard, vary in hue from skin-toned to pink to red, and may range in size from 1 to 6 millimeters in diameter. Fibrous papules are fibrous masses that may include collagen and blood vessels. The development of numerous fibrous papules may be related to the existence of genetic disorders and other conditions. When these factors are present, the papules may extend beyond the nasal area and appear to be many and distributed. Treatment for fibrous papules may include surgery.

Congenital Generalized Fibromatosis (Infantile Myofibromatosis)

Congenital Generalized fibromatosis, or infantile myofibromatosis is a rare disorder characterized by the growth of one or more noncancerous tumors affecting the skin, bone, muscle, soft tissue, and rarely the internal organs. The severity and specific symptoms, including the specific location and number of tumors can vary greatly from one person to another. These tumors may not metastasize but can grow large enough to cause symptoms by compressing or damaging nearby organs or other parts of the body. Treatment for congenital generalized fibromatosis may depend upon the location of the lesion. Spontaneous regression may occur; however, recurrence of the lesion may be possible. Treatment for congenital generalized fibromatosis may include surgery.

Aponeurotic Fibromas

Aponeurotic fibroma also known as calcifying juvenile aponeurotic fibroma, juvenile aponeurotic fibromatosis, or juvenile nodular aponeurotic fibroma, is a rare, painless, and slow-growing tumor mass. Aponeurotic fibroma may be attached to a tendon or a fascia and may appear on the hands or legs. Symptoms of aponeurotic fibromas may include swollen mass of the tumor, which may appear on the hands and feet and the tumor may be less than 3 centimeters in dimension. Over 50% of tumors may recur after surgical excision and the risk of recurrence may be higher in children. Aponeurotic fibroma tumor size and resulting pain or disability with movement may affect the person's quality of life. Treatment of aponeurotic fibroma may include complete surgical excision.

Infantile Digital Fibromatosis

Infantile digital fibroma, or fibromatosis, may present as single or multiple gelatinous or firm pinkish nodules on the fingers or toes of an infant. Similar lesions may occasionally be diagnosed elsewhere on the hands, feet, arms or elsewhere on the body. Although infantile digital fibromas may grow to a size of 2 cm, they are harmless and do not usually cause any symptoms unless they rub on the neighboring toe or footwear. Eventually, many fibromas may resorb and disappear by themselves over 2 to 3 years. Where infantile digital fibromas are not causing problems, a conservative wait and see approach may be used. Treatment for infantile digital fibroma may include surgical excision. However, infantile digital fibromas may recur after surgery.

Fibromatosis Colli

Fibromatosis colli, or sternocleidomastoideor of infancy, is a rare benign mass in the muscle on the side of the neck. The tumor may appear on the right side, and may be firm, measuring a couple centimeters in diameter. Fibromatosis colli tumor of infancy may be the most common of the congenital muscular "torticollis" or "twisted neck" conditions. Symptoms of fibromatosis colli of infancy may include a firm lump that appears on the side of a newborn's neck, usually between the second and eighth weeks of life that appears to be part of the neck muscle, the lump is not attached to the skin and is able to be moved when manipulated, a neck that bends slightly, a head that tilts, facial asymmetry, flat spot on the side of the head, infant preferring to look in the direction away from the affected neck muscle, infant that was positioned breech late in pregnancy, and delivery that was long and difficult. Treatment options for fibromatosis colli may include passive stretching, repositioning, massage, corrective helmet or molding cup, or surgery.

Dermatofibrosis Lenticularis (Buschke-Ollendorf Syndrome)

Dermatofibrosis lenticularis or Buschke-Ollendorf syndrome is a rare, hereditary disorder affecting the connective tissues. It is also known as dermatofibrosis lenticularis disseminata, dermato-osteopoikilosis and familial cutaneous collagenoma. Buschke-Ollendorf syndrome lesions may be present at birth. Buschke-Ollendorf syndrome can be characterized by small connective tissue naevi. The torso and extremities are most often affected. The naevi are elastomas, collagenomas, or fibromas and may be slightly elevated, yellowish papules, nodules, or plaques. Buschke-Ollendorf lesions may be painless and do not itch. Non-cutaneous but significant features of Buschke-Ollendorf syndrome may include: osteopoikilosis, nasolacrimal duct obstruction, amblyopia or strabismus, benign lymphoid hyperplasia, short stature, diabetes mellitus, aortic stenosis, and hearing impairment. Treatment for Buschke-Ollendorf may include surgical treatment of deafness where indicated or surgery.

Ionizing Radiation-Induced Fibrosis

Ionizing radiation may cause morphological and functional alterations in the tissues and is an important treatment modality for cancer patients. The extent of radiation damage can be related to several factors, including the total radiation dose, tissue irradiation volume, and the radiation dose's time interval. The highly proliferative and oxygenated cells may be the most sensitive to radiation damage; therefore, the most radiosensitive organs are the bone marrow, the reproductive and gastrointestinal systems, the skin, the muscles, and the brain. Radiation damage can be divided into acute or late (chronic); acute damage occurs within hours or weeks of radiation exposure, while chronic damage occurs months or years after radiation exposure.

Fibrosis is a late effect of ionizing radiation therapy, which can significantly reduce patients' quality of life. Radiation-induced fibrosis (RIF) may occur 4 to 12 months after radiation therapy in the skin, subcutaneous tissue, and other organs exposed to irradiation (radiation dose >50 gray). RIF's pathogenetic mechanism is similar to the wound healing process; ionizing radiation causes DNA damage and induces reactive oxygen and nitrogen species production, stimulating inflammatory and fibrotic processes. Fibroblasts and myofibroblasts produce collagen, fibronectin, and proteoglycans resulting in increased tissue thickening, reduced tissue compliance, and functional alteration. The transforming growth factor-beta (TGFβ) may be the prevalent growth factor that mediates the fibrotic response. Symptoms of RIF of the skin can include cutaneous induration and retraction, lymphedema, restricted movements, necrosis, and ulceration. Treatment options for RIF may include topical and oral medications and physical therapies. Mechanical massage of the affected area may counter tissue fibrosis, reducing pain, itching, and thickening of the skin. Oral administration of antioxidants such as alpha-tocopherol (vitamin E) can help protect cells from radiation-induced DNA damage. Similarly, pentoxifylline, can effectively inhibit the proliferation of fibroblasts. Other therapeutic agents used for RIF treatment include hyperbaric oxygen therapy, superoxide dismutase (SOD), IFNγ, and laser therapy with epidermal grafting.

Pulmonary Fibrosis

Pulmonary fibrosis is a lung disease that occurs when lung tissue becomes damaged and scarred. Pulmonary fibrosis scars and thickens lung tissue. It impacts the connecting tissue in the lung and alveoli (air sacs inside the lungs). Alveoli are tiny, delicate air sacs in the lungs. In pulmonary fibrosis, the thin walls of these air sacs scar and thicken. The lung damage gradually gets worse over time. The thickened, stiff tissue can make it harder for the lungs to work properly. Hard, stiff lung tissues may not expand as well as they should, making it harder to breathe. Symptoms of pulmonary fibrosis may include shortness of breath, dry cough, extreme tiredness, weight loss that is not intended, aching muscles and joints, and widening and rounding of the tips of the fingers or toes, called clubbing.

Pulmonary fibrosis is a progressive disease, which means it worsens over time. As the condition gets worse, people may become more and more short of breath. The lung damage caused by pulmonary fibrosis cannot be repaired. There is no cure, and it eventually leads to death. Medicines and therapies can sometimes help slow down the rate of fibrosis, ease symptoms, and improve quality of life. For some people, a lung transplant might be an option.

Idiopathic Pulmonary Fibrosis

Idiopathic pulmonary fibrosis (IPF) of undetermined etiology is a serious lung disease where scar tissue grows inside the lungs making it hard to breathe. The condition gets worse over time. In IPF thick scar tissue slows oxygen flow from the lungs to the blood, which can keep the body from working as it should. In the lungs, scar tissue forms on air sac walls and in the spaces around them, making them thick and hard. This scarring may make it harder for air to pass in and out of the sacs. Rapid, shallow breathing or a dry, hacking cough that does not go away may occur. There is no cure for IPF. For most, symptoms do not get better, but treatments can slow damage to the lungs. Treatments can help manage symptoms and make breathing easier. FDA approved treatments for idiopathic pulmonary fibrosis include nintedanib and pirfenidone.

Interstitial Lung Disease

Interstitial lung disease describes a large group of disorders, which include IPF and other pulmonary fibroses, most of which can cause inflammation and progressive scarring of lung tissue. Interstitial lung disease may damage tissues between the small air sacs, or alveoli, in the lungs and the blood vessels around them. This can make it harder to move oxygen out of the lungs and into the body. Interstitial lung disease can occur when an injury to the lungs triggers an abnormal healing response, causing the tissue around the alveoli to become scarred and thickened. Scarring in the lungs can make it hard to breathe, and a chronic cough could develop. Lack of oxygen can cause feelings of fatigue. Interstitial lung disease can cause symptoms of shortness of breath that can become worse with exercise or exertion, dry cough, fatigue, and chest discomfort. Symptoms may be mild at first but get worse over months or years. Interstitial lung disease can lead to serious life-threatening complications, including pulmonary hypertension, right-sided heart failure, and respiratory failure. There is no cure for interstitial lung disease. Treatments focus on treating underlying disease and improving symptoms, and may include azithromycin, pirfenidone, nintedanib, azathioprine, or prednisolone.

Fibrosing Hypersensitivity Pneumonitis

Fibrosing hypersensitivity pneumonitis (FHP) is a type of allergic reaction that causes inflammation in the small air sacs, or alveoli in the lungs. In FHP ongoing immune activation and inflammation are believed to lead to the expansion/activation of the fibroblast population and the accumulation of extracellular matrix. Unlike common allergies that cause hay fever and asthma, repeated exposure to allergens that cause FHP can lead to inflammation that can permanently damage the lungs.

Symptoms of acute FHP may include shortness of breath, dry cough, chest tightness, chills, fatigue, fever, and muscle aches. Symptoms of chronic FHP may include shortness of breath, especially with exertion or activity, cough, fatigue, weight loss, and finger or toe clubbing. Chronic FHP is considered an interstitial lung disease. It can lead to lung scarring over time. With continued exposure to an allergen that causes FHP, serious complications may occur, including scarring in the lungs and pulmonary hypertension. Damage caused by chronic FHP is not reversible. People in whom the offending antigen is identified have a better prognosis. However, disease progression even after termination of the antigen exposure may occur. For people who have lung scarring due to FHP, the disease may be fatal within a few years without a lung transplant. Treatment for FHP may include medications to reduce inflammation, open the airways, or increase the person's oxygen levels. FDA approved treatment for FHP may include steroids, nintedanib or pirfenidone.

Cardiovascular Disease

Cardiovascular disease (CVD) is a group of diseases that affect the heart and blood vessels. The diseases can affect one or many parts of the heart and may include the blood vessels. CVD includes heart or blood vessel issues including narrowing of the blood vessels in the heart or other organs in the body, heart and blood vessel problems present at birth, heart valve disease, disease of the heart muscle, and irregular heart rhythms. Cardiovascular fibrosis may be a critical pathological process of CVD. Generally, cardiovascular fibrosis arises from enhanced resident immune and inflammatory response, uncontrolled cellular proliferation, and activation of ECM-producing myofibroblasts due to an aberrant wound-healing response to myocardial injury, ultimately leading to cardiovascular stiffness, pathological remodeling and cardiovascular disorders.

CVD symptoms may include chest pain, chest tightness, chest pressure, and chest discomfort or angina, shortness of breath during activity or at rest, pain in the neck, jaw, throat, upper belly area or back, pain, numbness, weakness, or coldness in the extremities if the blood vessels in those areas are narrowed. Treatment of CVD can vary depending on the symptoms and type of CVD presenting, and may include lifestyle changes, medications, procedures or surgeries, cardiac rehabilitation, and active surveillance. Untreated CVD can lead to serious complications, including a higher risk of heart attack, stroke, acute limb ischemia, aortic dissection, and sudden cardiac death.

Reactive Interstitial Fibrosis

Cardiac fibrosis is a process of pathological ECM remodeling, leading to abnormalities in matrix composition and quality, as well as an impaired heart muscle function. Initially, ECM deposition is a protective mechanism and can be beneficial for wound healing and tissue regeneration. However, excessive and continuous ECM deposition, particularly collagen type I secretion, may lead to impaired tissue function. Fibrotic scars of the cardiac muscle most commonly occur after myocardial infarction; however, there may be various other conditions promoting cardiac fibrosis such as hypertensive heart disease, diabetic hypertrophic cardiomyopathy and idiopathic dilated cardiomyopathy.

In the heart, these scars can cause several cardiac dysfunctions either by reducing ejection fraction due to a stiffened myocardial matrix, or by impairing electric conductance, or they can even lead to death. There are several different types of cardiac scars depending on the underlying cause of fibrosis. Cardiac fibrosis may occur when there is scarring in the cardiac muscle that is characterized by an increased collagen type I deposition as well as cardiac fibroblast activation and differentiation into myofibroblasts. These pathological changes may lead to an increased matrix stiffness and lead to abnormalities in cardiac function. Three types of myocardial fibrosis have been identified: reactive interstitial fibrosis, infiltrative interstitial fibrosis and replacement fibrosis. Reactive interstitial fibrosis can lead to a pressure overload and cardiomyopathies due to an increased ECM deposition without a significant loss of cardiomyocytes. Treatments used to impact the fibrotic response in injuries are angiotensin (AT)-converting enzyme and angiotensin receptor antagonist, β-blockers, endothelin antagonists, statins and eplerenone. There also may be approaches to influence fibroblast activation by blocking TGFβ or Smad3 signaling.

Replacement Fibrosis

Replacement fibrosis occurs after cardiac injury like myocardial infarction, where cardiac cells are damaged. In replacement fibrosis, dead cells may be replaced and a predominantly collagen type I-containing scar may be formed in the cardiac tissue. Cardiomyocyte death after injury or due to diseases may lead to an inflammatory response and activation of cardiac fibroblasts. Under physiological conditions, cardiac fibroblasts may express no stress fibers. After injury however, fibroblasts are activated and may transdifferentiate into stress-fiber expressing myofibroblasts. This phenotype may express α smooth muscle actin and develop contractile bundles. Changes in the mechanical and structural microenvironment but also the increase of certain factors such as transforming growth factor β (TGFβ) can lead to the activation of cardiac fibroblasts.

Furthermore, mast cell accumulation has been observed at sites of injury. These cells degranulate and release histamine, which may stimulate fibroblast proliferation and collagen synthesis. The relative contribution of pro-fibrotic factors inducing fibroblast activation may depend on the underlying disease or injury. Activated fibroblasts may have an increased proliferation and migration capacity. ECM synthesis and deposition can be further characteristics of activated myofibroblasts. Treatments used to impact the fibrotic response in injuries are angiotensin (AT)-converting enzyme and angiotensin receptor antagonist, β-blockers, endothelin antagonists, statins and eplerenone. There also may be approaches to influence fibroblast activation by blocking TGFβ or Smad3 signaling.

Infiltrate Interstitial Fibrosis

Infiltrative interstitial fibrosis is another type of cardiac fibrosis. Infiltrative interstitial fibrosis can be characterized by glycolipid build up in different cells of the heart, which can be observed in patients with Fabry disease. The pathological changes that occur due to myocardial fibrosis can lead to an increased matrix stiffness and lead to abnormalities in cardiac function. Treatments used to impact the fibrotic response in injuries are angiotensin (AT)-converting enzyme and angiotensin receptor antagonist, β-blockers, endothelin antagonists, statins and eplerenone. There also may be approaches to influence fibroblast activation by blocking TGFβ or Smad3 signaling.

Endomyocardial Fibrosis

Endomyocardial fibrosis (EMF) is characterized by left and right ventricular endocardial fibrosis and resultant restrictive cardiomyopathy. The underlying process of EMF may produce focal or diffuse endocardial thickening and fibrosis which may lead to restrictive physiology. Endomyocardial fibrosis may involve the apices of the right and left ventricle. In the left ventricle, the fibrosis typically extends from the apex to the posterior leaflet of the mitral valve, sparing the anterior mitral valve leaflet and the left ventricular outflow tract. Furthermore, in some cases fibrosis can involve the papillary muscles and chordae tendineae resulting in atrioventricular valve regurgitation and distortion. In advanced stages, endocardial calcific deposits and thrombus formation can occur. In EMF the fibrotic thickening of the endocardium may occur due to acellular collagen tissue deposition with the proliferation of fibrous tissue in the underlying myocardium.

Symptoms of EMF may depend on the cardiac chamber involved and its severity. The initial phase of EMF is the acute carditis phase, characterized by a febrile illness and in severe cases cardiogenic shock. Those who survive the acute illness may progress into sub-acute and chronic phase. In the chronic phase, symptoms may include advanced complications such as heart failure, arrhythmias or thromboembolic disease. For people who have advanced complications, EMF may be fatal. Treatment for EMF may include strategies to provide symptomatic relief and may include immunosuppressive therapies, diuretics, ACE inhibitors, beta-blockers, anticoagulation, and surgery.

Heart Failure

Heart failure is a chronic condition in which the heart cannot pump blood well enough to meet the body's needs. Although the heart is working, it cannot handle the amount of blood it should, and blood builds up in other parts of the body. Conditions such as narrowed arteries in the heart and high blood pressure may gradually leave the heart too weak or stiff to fill and pump blood properly. Cardiac fibroblasts (CFs) can play a crucial role in myocardial disease and healing. These cells are responsible for the production and deposition of ECM proteins—type 1 collagen—which serves as a scaffold for other cellular components and is integral to the structural integrity and function of the myocardium. Fibroblasts respond to cytokines and neurohormal factors, differentiating into activated fibroblasts and smooth muscle-like myofibroblasts that are critical in the healing response of diseased or injured myocardium. These cells may exert their effects on the ECM via regulation of matrix metalloproteinases and fibronectin. Although the primary response to myocardial injury—wound healing, reparative scar formation and remodelling—is important in limiting tissue damage, chronic changes may become maladaptive, ultimately impairing cardiac function. Myocardial fibrosis may be a common final pathway in chronic myocardial disease and is the structural correlate of heart failure.

Heart failure symptoms may include shortness of breath with activity or when lying down, fatigue and weakness, swelling in the legs, ankles, and feet, rapid or irregular heartbeat, reduced ability to exercise, wheezing, cough that does not go away or a cough that produces white or pink mucus with spots of blood, swelling of the abdomen, very rapid weight gain from fluid buildup, nausea and lack of appetite, difficulty concentrating or decreased alertness, and chest pain. Complications of heart failure may include kidney damage or failure, other heart problems, liver damage, sudden cardiac death, heart attack, stroke, aneurysm, peripheral artery disease, and sudden cardiac arrest. Treatment of heart failure may improve the symptoms of heart failure and may help some people live longer. However, heart failure can be life-threatening and people with heart failure may develop severe symptoms. Some people with heart failure may need a heart transplant or a device to help the heart pump blood.

Arrhythmia

An arrhythmia, or dysrhythmia, is an abnormal, or irregular heartbeat. An arrhythmia may occur when the electrical signals that cause the heart to beat do not function properly and the heart beats too fast or too slow or the pattern of the heartbeat is inconsistent. Cardiac fibroblasts (CFs) are an essential cell type, mainly derived from the proepicardium, endothelial cells, and neural crest cells, and reside within the myocardial and valve interstitium, epicardial, and perivascular regions. CFs are essential for normal cardiac function and mediate various physiological forces, including mechanical and electrical stimuli. CFs produce paracrine factors that significantly change the electrophysiological activity in cardiomyocytes. CFs can interact with cardiomyocytes through gap-junctional proteins, such as connexins. Additionally, CFs may be widely accepted as the main regulator of the heart's response to various pathological injuries, such as ECM production, matrix degradation, inflammatory cell recruitment, and scar formation. After an acute myocardial injury, the expression of various proinflammatory cytokines is upregulated in the initial inflammatory response in CFs, resulting in subsequent inflammatory cell infiltration and cytokine expression in the heart. In this setting, mechanical stress and inflammation may stimulate CF activation, which may show morphological characteristics of both fibroblasts and smooth muscle cells with the expression of a smooth muscle actin (αSMA). Activated CFs secrete elevated levels of collagen and other ECM proteins. This reaction maintains the heart's structural integrity and pressure-generating capacity. In the advanced phases of fibrotic scar formation, the tensile strength of collagen may increase within the injury site. Excess ECM deposition and fibroblast proliferation can disturb the mechano-electric coupling of cardiomyocytes, thereby increasing the risk of arrhythmia and mortality.

Arrhythmia symptoms may include heart palpitations, dizziness or lightheadedness, fainting, shortness of breath, chest pain, tightness, or discomfort, weakness or fatigue, anxiety, blurry vision, sweating, rapid heartbeat, and slow heartbeat. Complications of arrhythmia may include blood clots, which can lead to stroke, heart failure, weakening of the heart muscle or cardiomyopathy, cardiac arrest, sudden cardiac death alzheimer's disease and dementia. Having an arrhythmia may impact the person's ability to drive safely, which could interfere with a normal life. Arrhythmia treatment depends on the type of arrhythmia a person has, and may include medication, vagal maneuvers, pacemaker, implantable cardioverter defibrillator, biventricular pacemaker and defibrillators, catheter ablation, pulmonary vein isolation, cardiac surgery, lifestyle and alternative treatments.

Valvular Disease

Valvular disease, or heart valve disease refers to any of several conditions that prevent one or more of the valves in the heart from functioning properly. In heart valve disease a valve can have damage or be diseased. There are four heart valves, which keep blood flowing through the heart in the correct direction. Heart valves are composed of leaflets or flaps that work together to open and close to allow blood to flow across the opening. Healthy heart valve leaflets are able to fully open and close the valve during the heartbeat, but diseased valves may not open or close completely. This can change how blood flows through the heart to the rest of the body.

Myocardial fibrosis may be common in valvular disease and may be closely associated with impaired ventricular function. This can lead to heart failure, sudden cardiac arrest, and death. Symptoms of valvular disease may include increasing shortness of breath, especially with physical activity or lying down, palpitations, swelling of the ankles, feet, or abdomen, weakness or dizziness, rapid weight gain, chest discomfort upon exertion, or fatigue. Treatment for valvular disease may depend on the underlying cause of the disease, and may include protecting the valve from further damage, medication therapy, and surgery.

Vitreous Fibrosis

Various insults to the vitreous, such as penetrating injury, inflammation, etc., can result in reactive vascularization and organization with proliferation of vitreal fibrous connective tissue, such as vitreal scar or fibrous membrane formation. In early fibrosis, loose fibrous connective tissue can fill the vitreous space between the lens and retina. More advanced fibrosis can be characterized by dense sheets of mature fibrous tissue that replace the normal vitreous. Vitreous fibrosis may be associated with chronic inflammation and/or pigmented macrophage accumulations. Reactive retinal pigment epithelium (RPE) cells may migrate transretinally into the vitreous and spread along the inner surface of the retina. Such migrant RPE cells can undergo fibrous metaplasia (epithelial-to-mesenchymal transition) into fibroblast-like cells and participate in the formation of abnormal vitreal fibrous tissue, including fibrous membranes on the surface of the retina and other posterior ocular structures. Other cells that participate in development of vitreal fibrosis may include activated resident vitreal hyalocytes, retinal Müller cells and astrocytes, immigrant macrophages, and scleral fibroblasts. Cartilaginous or osseous metaplasia can occasionally form in late-stage vitreal fibrosis.

Subepithelial Fibrosis

Fibrosis is a common pathologic event observed in various organs of the body. Fibrotic diseases of the ocular surface, including corneal and conjunctival scar, have been recognized as having a mechanism similar to that of fibrotic disorders in other tissues of the human body. Inflammation is thought to trigger and facilitate the progression of fibrosis. Subsequently, epithelial cells may be stimulated and injured without appropriate repair, resulting in activation of underlying fibroblasts. These fibroblasts derive from bone marrow but may also arise as a result of epithelial-mesenchymal transition (EMT) in cells at injury sites. This process of fibrotic tissue transformation can be characterized by an increase in abnormal extracellular matrix, including collagen fibers. Epithelial cells may undergo a change in phenotype, differentiating into fibroblastic cells in response to morphogenic pressure from injured tissue in what is known as EMT. Abnormal subepithelial fibrosis and epithelial keratinization, can cause vision-threatening diseases such as severe ocular surface fibrosis due to total limbal stem cell deficiency. Histopathologically, corneas with total limbal stem cell deficiency can be characterized by conjunctival ingrowth (conjunctivalization), vascularization and chronic inflammation. These diseases may destroy limbal epithelial stem cells, their surrounding environment, or a combination of both.

Generally, the mechanism of corneal subepithelial fibrosis is initiated by corneal stromal fibroblast activation due to inflammatory cytokines. This activation may then lead to transdifferentiation into α-smooth muscle actin (α-SMA)-positive myofibroblasts. Contraction of the stress fibers in myofibroblasts can subsequently result in the development of fibrosis.

Macular Degeneration

Macular Degeneration is an eye disease that affects central vision. People with macular degeneration cannot see things directly in front of them. Macular degeneration affects the macula, or the central part of the retina. Subretinal fibrosis may be the most common natural sequela of macular neovascularization and may develop despite successful anti-VEGF therapy. Current evidence suggests that subretinal fibrosis and its ECM components are produced mainly by activated myofibroblasts that transdifferentiate from retinal pigment epithelium, pericytes, endothelial, glial, and immune cells, leading to a secondary response involving the innate immune system. The biological function of subretinal fibrotic material deposition may limit the spread of tissue injury, but the associated prolonged and massive reaction may eventually lead to irreversible vision loss and impede tissue regeneration.

Macular degeneration may develop in one eye or both eyes with different levels of severity. Symptoms may include being less able to see in low light, blurred vision, problems or changes in the way people see colors, low vision, straight lines perceived as being curvy or wavy, and blank spots or dark spots in a person's field of vision. There are two types of macular degeneration: dry and wet. Dry macular degeneration can develop when tiny yellow protein deposits, called drusen, form under the macula. The built-up deposits dry and thin the macula. Vision loss with dry macular degeneration may occur gradually. Wet, or exudative macular degeneration may occur when abnormal blood vessels develop under the retina and macula. The blood vessels leak blood and fluid. Because of fluid buildup, a bulge may form in the macula. Dark spots in the center of vision may occur. This type of macular degeneration can quickly lead to total loss of central vision. FDA approved treatments for macular degeneration include syfovre, izervay, ranibizumab, ranibizumab-nuna, or vabysmo.

Strabismus

Strabismus, or crossed eyes, is a condition in which the eyes do not line up with one another, or point in different directions. In strabismus, the eyes do not work together to look at objects, and the muscles that control eye movement may have problems controlling eye movement and cannot keep normal ocular alignment. Strabismus may be caused by congenital fibrosis of extraocular muscles or congenital orbital fibrosis, or maldevelopment of orbital structures.

Symptoms of strabismus may include double vision, closing or covering one eye when looking at something nearby, tilting or turning the head, headaches, difficulty reading, eye strain, and closing one eye when looking at objects that are far away or when in bright light. If the eyes are not properly aligned, it may cause lazy eye, called amblyopia, or permanent poor vision in the turned eye, blurry vision, which can affect performance in school and at work, and interfere with enjoyment of hobbies and leisure activities, eye strain, fatigue, headaches, double vision, poor three-dimensional vision, low self-esteem. In some cases, a serious problem, such as a brain tumor may be overlooked if the healthcare provider does not diagnose and follow the strabismus. Treatment options for strabismus may include eyeglasses or contact lenses, prism lenses, orthoptics, medications, patching, and eye muscle surgery. FDA approved treatment for strabismus may include botulinum toxin.

Chronic Kidney Disease

Chronic kidney disease (CKD), or chronic kidney failure, involves a gradual loss of kidney function. The kidneys filter waste and excess fluids from the blood, which are then removed in the urine. When the kidneys begin to lose their function, they cannot filter waste, and waste builds up in the blood. Renal inflammation may be the fuel for the initiation of renal fibrosis. In acute and chronic kidney injury, the release of cytokines, infiltration of inflammatory cells, and subsequent EMT may lead to renal fibrosis and failure. Tubular repair mechanisms involve epithelial growth factor receptor (EGFR) activation. Although its acute activation may be beneficial in the early stages of kidney injury, its chronic activation may lead to renal fibrosis. This activation may increase the expression of TGF-ß1, which stimulates interstitial myofibroblast proliferation, inducing the secretion of collagen and other ECM proteins, leading to interstitial fibrosis and functional failure of nephrons.

Complications of CKD may include a low red blood cell count, or anemia, weak and brittle bones, gout, metabolic acidosis, high blood pressure, heart disease and blood vessel disease, including increased risk of stroke and heart attack, nerve damage, high potassium or hyperkalemia, high phosphorous or hyperphosphatemia, decreased immune response due to a weak immune system, damage to the central nervous system which can cause difficulty concentrating, personality changes, or seizures, pericarditis, pregnancy complications that carry risks for the mother and developing fetus, irreversible damage to the kidneys, and fluid buildup, leading to swelling of the feet, ankles and hands. FDA approved treatment for CKD may include finerenone, dapagliflozin, or empagliflozin. However, controlling the cause may not keep kidney damage from progressing. CKD can progress to end-stage kidney failure, which is fatal without dialysis or a kidney transplant.

Diabetic Kidney Disease

Diabetic kidney disease, or diabetic nephropathy, is a progressive disease that affects the kidneys. Each kidney contains more than one million nephrons, which help filter blood and balance fluids and electrolytes in the body. Each nephron contains groups of tiny blood vessels called glomeruli. The glomeruli perform the first step in filtering the blood. Glomeruli have semi-permeable membranes which allow water and soluble wastes to pass through, which eventually leave the body in the urine. Diabetes may cause diabetes-related nephropathy. In diabetes the body cannot properly process blood sugar from foods and drinks that are consumed. Extra glucose in the bloodstream may damage the glomerular membranes as well as other parts of the nephron. Damaged glomeruli may not properly filter fluids. When the glomeruli cannot properly filter fluids, toxins that should be excreted in the urine may accumulate in the blood and body. Inflammation and resulting fibrosis may be main features of diabetic kidney disease. Renal interstitial fibrosis may be a crucial metabolic change in the late stage of diabetic kidney disease, which is considered to be complex and irreversible.

Diabetic kidney disease symptoms usually do not appear until the disease has affected at least 80% to 90% of the kidneys. Symptoms may include swelling in the face, hands and feet, nausea and vomiting, tiredness or fatigue, dyspnea, loss of appetite, foamy or bubbly urine, difficulty focusing or confusion, dry, itchy skin, muscle cramps, and not needing to take as much insulin. Diabetic kidney disease cannot be reversed. FDA approved treatment for diabetic kidney disease may include canagliflozin. In advanced diabetic kidney disease, treatment options include dialysis and kidney transplant.

Liver Cirrhosis

Liver cirrhosis is late-stage liver disease in which healthy liver tissue has been gradually replaced with scar tissue. Liver cirrhosis can be a result of long-term, chronic hepatitis. Hepatitis is inflammation of the liver, which has many causes. When inflammation is ongoing, the liver attempts to repair itself by scarring. Cirrhosis occurs when there is permanent scarring in the liver, which cannot be reversed, and there are not enough healthy cells left for the liver to heal itself. Cirrhosis is a progressive condition that worsens as more scar tissue develops. Scarring in the liver may block the flow of blood and oxygen through liver tissues. This may slow the liver's ability to process blood, metabolize nutrients, and filter out toxins. Scar tissue can also compress blood vessels running through the liver, including the portal vein system, leading to portal hypertension.

Complications of cirrhosis may include general toxicity, feeling ill and foggy, reduced immunity, healing, and recovery, fluid leakage from the veins, causing swelling in the body, hormonal imbalances and deficiencies, digestive difficulties, malabsorption and malnutrition, mild cognitive impairment and motor dysfunction. Life-threatening complications of cirrhosis and portal hypertension can include gastrointestinal varices and gastrointestinal bleeding, spontaneous bacterial peritonitis, kidney failure, respiratory failure, chronic liver failure, and liver cancer. Depending on what is causing cirrhosis, how treatable the cause is, and how well the treatment response is, it may be possible to slow or stop cirrhosis from progressing further. Treatment for cirrhosis of the liver may include managing the cause, if possible, to slow or reduce the damage, general diet and lifestyle measures to reduce the stress on the liver, managing or screening for complications of cirrhosis, and liver transplant.

Nonalcoholic Steatohepatitis (NASH)

Nonalcoholic steatohepatitis, or NASH, also called MASH, is a serious form of fatty liver disease that causes the liver to swell and become damaged due to fat deposits in the liver. NASH may get worse and may lead to serious liver scarring, called cirrhosis, and even liver cancer. Cirrhosis may be the main complication of NASH. Cirrhosis can occur because of liver injury, such as the damage caused by inflammation in NASH. As the liver tries to stop inflammation, it may create areas of scarring, called fibrosis. With ongoing inflammation, fibrosis may spread and take up more liver tissue. As steatohepatitis progresses and more liver tissue turns to scar tissue, the liver may begin to lose blood supply. This may cause irreversible cell death. The most common symptoms of moderate NASH are pain in the upper right abdomen, weakness and fatigue, loss of appetite, and unexplained weight loss. More advanced stages may begin to resemble symptoms of cirrhosis, which may include yellowing of the skin and whites of the eyes, easy bruising and bleeding, ascites, swelling in the legs and feet, enlarged liver or enlarged spleen, enlarged spider-like veins under the skin, persistent itchiness, swollen veins in the esophagus, or esophageal varices, which can rupture and bleed, confusion, sleepiness and slurred speech, also called hepatic encephalopathy and portal hypertension, which can cause intestinal bleeding.

The primary risk of NASH is progressive fibrosis leading to cirrhosis of the liver. Cirrhosis is associated with an increased risk of liver cancer. Most people with liver cancer have cirrhosis. Currently, there are no medications available that can reverse the disease process in NASH. FDA approved treatment for NASH includes resmetirom.

Nonalcoholic Fatty Liver Disease (NAFLD)

Non-alcoholic fatty liver disease, or NAFLD, also called MASLD, is a liver condition that occurs when the body stores excess fat in the liver. NAFLD often has no symptoms. When symptoms occur, they may include fatigue, not feeling well, or malaise, and pain or discomfort in the upper right abdomen. Some people with NAFLD can develop NASH. Severe liver scarring, or cirrhosis, can be the main complication of NAFLD. Cirrhosis may occur due to liver injury. As the liver tries to stop inflammation, it may create areas of scarring, or fibrosis. With ongoing inflammation, fibrosis may spread and take up more liver tissue. Existing scar tissue cannot be revived. If nothing is done to stop the scarring, cirrhosis can lead to fluid buildup in the abdomen, swollen veins in the esophagus, or esophageal varices, which can rupture and bleed, hepatic encephalopathy, overactive spleen, liver cancer, and end-stage liver failure. Treatment for NAFLD may include lifestyle changes, which can reduce or eliminate the inflammation associated with steatohepatitis. Inflammation can be what triggers fibrosis and progressive liver damage and may be what separates those with NASH from those who live without problems from NAFLD.

Glial Scar

Fibrosis is formed after injury in most of the organs as a common and complex response that affects regeneration of damaged tissue. In central nervous system (CNS), glial scar grows as a major physical and chemical barrier against regeneration of neurons as it forms dense isolation and creates an inhibitory environment, resulting in limitation of optimal neural function and permanent deficits of human body. In neurological damage, glial scar is mainly attributed to the activation of resident astrocytes which surrounds the lesion core and walls off intact neurons. Glial cells may induce the infiltration of immune cells, resulting in transient increase in ECM deposition and inflammatory factors which inhibit axonal regeneration, impede functional recovery, and may contribute to the occurrence of neurological complications. Signal molecules in coordination can play crucial roles in astrocytes for glial scar formation after damage occurs. Some of the key molecules that are involved in astrocytic hypertrophy, proliferation, migration, and gliogenesis may orchestrate the formation of glial scars. The response of the glial scar to CNS injury, traumatic brain injury and spinal cord injury may involve a cascade of cellular and molecular changes that influence the local microenvironment and the recovery of neuronal function. Glial scars in different pathological conditions such as CNS infection, brain stroke, and traumatic injuries may exhibit their own patterns to reorganize the nerve tissue and to repair neuronal damages. Moreover, the ECM of the glial scar may influence the prognosis and the onset of neurological complications.

Glial scar formation may depend on the interactions between CNS cells and non-CNS cells including hematogenous macrophages and fibroblasts. Traumatic injury causes direct large-scale death of neurons and glia around the site of the injury, shearing of ascending and descending axons and damage to the vasculature. Traumatic injury can lead to hemorrhage at the lesion and release of factors associated with glial scar formation and immune response. Astrocytes and microglia begin to accumulate around the lesion and increase the expression of pro-inflammatory cytokines and chemokines that inhibit axonal regeneration. Increased levels of pro-inflammatory cytokines, myelin debris, and CSPGs in the glial scar may contribute to secondary damage to neurons, oligodendrocytes, and dystrophic endings of axonal dieback and inhibit the recovery. Perivascular fibroblasts may be attracted by hematogenous macrophages, which infiltrate the lesion, and the perivascular fibroblasts form the fibrotic part of the scar. This part of the scar may show increased density in a week, and the scar starts to mature during the second week by forming tight borders between fibrotic components with glial components after spinal cord injury.

Spinal Cord Injury

Severe spinal cord injury causes permanent loss of function and sensation throughout the body. The trauma may cause a multifaceted torrent of pathophysiological processes which ultimately act to form a complex structure, permanently remodeling the cellular architecture and extracellular matrix. This structure is traditionally termed the glial/fibrotic scar. Similar cellular formations occur following stroke, infection, and neurodegenerative diseases of the central nervous system (CNS) signifying their fundamental importance to preservation of function. The scar may perform multiple roles affecting recovery following traumatic injury.

Traumatic SCI begins with physical (primary) injury to the spinal cord, which may immediately cause axon shearing, bleeding, and cell death. This may lead to the release of alarmins, which recruit local microglia and systemically circulating immune cells that pass through the damaged blood-spinal cord barrier to propagate inflammation and secondary damage. This ensures that formation of the scar is triggered, in part, by inflammatory processes and requires the concerted effort of a myriad of different cell types as well as transcriptomic and molecular changes driven initially by inflammation-induced reactivity. The hypertrophic lesion penumbra which forms the following injury to the CNS (encapsulating reactive astrocytes, activated microglia, and oligodendrocyte progenitor cells) may comprise one of three inhibitory cellular compartments which impede axon regeneration both at PNS-to-CNS graft interfaces and within the lesion parenchyma. This is the glial scar. The second barrier to regeneration, which also may reside near the lesion penumbra but lies inside the glial scar, is the fibrotic scar—a structure replete with fibroblasts or fibroblastic-like cells including those derived from the meninges, mural/adventitial sources, or pericytes. Swirls of rigid basal lamina membrane may form between the astrocytic and fibroblastic layers of the scar further preventing axonal growth. The third barrier is the lesion epicenter itself, which may comprise mostly systemically derived inflammatory cells such as activated macrophages. While all these compartments are dynamic in composition, their formation may permanently alter the cellular landscape and extracellular matrix of the spinal cord up to centimeters rostral and caudal from the initial impact.

Chronic Pancreatitis

Pancreatitis is inflammation of the pancreas that causes swelling and pain. The pancreas is involved in digestion and regulating blood sugar. It makes digestive enzymes and hormones and delivers these substances to the small intestine through the pancreatic duct. Inflammation of the pancreas may occur due to gallstones blocking the pancreatic duct or from alcohol. Chronic pancreatitis is a long-term, progressive condition. It does not go away and gets worse over time. Chronic pancreatitis may occur when the injury or damage to the pancreas does not stop. Constant inflammation may cause scarring or fibrosis of the pancreas tissues, which can prevent the pancreas from making enzymes and hormones. Pancreatic fibrosis can be a pathological feature of pancreatitis and is frequently present in chronic pancreatitis.

Symptoms of chronic pancreatitis may include abdominal pain, indigestion and pain after eating, loss of appetite and unintended weight loss, fatty stool that leaves an oily film in the toilet, and lightheadedness. Abdominal pain from pancreatitis may be moderate to severe and may radiate to the back. Complications of chronic pancreatitis develop over time and may include exocrine pancreatic insufficiency, malabsorption, and malnutrition, hypoglycemia, hyperglycemia and type 1 diabetes, chronic pain, and increased risk of pancreatic cancer. Treatment for chronic pancreatitis may begin with pain management and lifestyle changes to slow the progression of the disease. Eventually, enzyme supplements and insulin injections to replace enzymes and insulin the pancreas no longer produces may be necessary.

Pancreatic Cancer

Pancreatic cancer occurs when cells in the pancreas mutate and multiply out of control, forming a tumor. The most common type of pancreatic cancer is pancreatic ductal adenocarcinoma. This type begins in the cells that line the ducts that carry digestive enzymes out of the pancreas. As pancreatic cancer progresses, it can cause complications such as weight loss, jaundice, pain, and bowel blockage.

Pancreatic fibrosis is a pathological feature of pancreatic cancer and is frequently present in pancreatic cancer. Studies have found that pancreatic fibrosis may be involved in the transformation of pancreatitis to pancreatic cancer. Treatment for pancreatic cancer may include surgery, pancreaticoduodenectomy, distal pancreatectomy, chemotherapy, radiation therapy, targeted drug therapy, and pain management. FDA approved treatments for pancreatic cancer include capecitabine, fluorouracil, gemcitabine, irinotecan, leucovorin, nab-paclitaxel, nanoliposomal irinotecan, and oxaliplatin.

Crohn's Disease

Crohn's disease is a condition that causes inflammation in part of the digestive system. Crohn's disease can affect any part of the digestive tract, but most often involves the small intestine and large intestine. Symptoms depend on where the disease occurs and the severity of disease. Early signs of Crohn's disease may include frequent diarrhea, abdominal pain and tenderness, unexplained weight loss, and blood in the stool. Other symptoms of Crohn's disease may include nausea, tiredness, joint pain, fever, long-lasting diarrhea, often bloody and with mucus or pus, weight loss and mouth sores.

In some people, the chronic inflammation of the gastrointestinal tract in Crohn's disease may lead to remodelling of the ECM and fibrosis. Fibrosis, in combination with expansion of smooth muscle layers, may leave the bowel segment narrowed and stiff resulting in strictures, which may require medical intervention. Treatment for Crohn's disease depends on what is causing the symptoms and how serious the symptoms are. FDA approved medications for Crohn's disease include adalimumab, adalimumab-adbm, adalimumab-atto, certolizumab, infliximab, infliximab-abda, infliximab-dyyb, and natalizumab. In 66% to 75% of people with Crohn's disease, surgery may be indicated.

Ulcerative Colitis

Ulcerative colitis is a lifelong condition that causes inflammation and ulcers inside the large intestine. Ulcerative colitis often causes bloody diarrhea and abdominal cramping. In ulcerative colitis, inflammation usually starts in the rectum. The inflammation can spread and affect all or part of the colon. Intestinal fibrosis can occur in ulcerative colitis and is defined as an excessive accumulation of scar tissue in the intestinal wall. Intestinal fibrosis followed by chronic and recurrent inflammation may lead to deposition of ECM in the mucosa, including collagen and fibronectin. Unhealed inflammation may trigger the excessive accumulation of ECM and increased production of collagen. Intestinal fibrosis may cause narrowing, intestinal obstruction, and need for surgical intervention.

Ulcerative colitis may be mild, moderate or severe, depending on symptoms. The most severe form, fulminant ulcerative colitis, is rare. It can cause life-threatening complications that require urgent medical treatment. About 25% of people with ulcerative colitis may eventually develop conditions and associated symptoms that affect body parts other than the colon. The inflammation can spread to bones, joints, eyes, skin, and liver. Treatments for ulcerative colitis may include medication and surgery. FDA approved treatments for ulcerative colitis include adalimumab, golimumab, infliximab, vedolizumab, ustekinumab, tofacitinib, and upadacitinib.

Idiopathic Retroperitoneal Fibrosis

Retroperitoneal fibrosis is a rare form of retroperitoneal disease that causes scar-like tissue, or fibrosis, over organs in the retroperitoneum. The retroperitoneum is a space behind the abdominal cavity. It includes the urinary system, kidneys, large vessels that transport blood to and from the legs, and adrenal glands. In retroperitoneal fibrosis, as the fibrosis progresses, it can affect the organs and structures in the retroperitoneum. It often affects the ureters, which transport urine from the kidneys to the bladder. In advanced cases, fibrosis may cause life-threatening complications, including kidney failure.

Symptoms of retroperitoneal fibrosis vary based on the location of fibrosis and how advanced it is. Treatment for retroperitoneal fibrosis may depend on the location and severity of the fibrosis. Treatments may include medications such as corticosteroids, immunomodulators, medications, surgery, and stents.

Peritoneal Fibrosis

The peritoneum is made up of a single layer of mesoderm-derived mesothelial cells and a thin layer of connective tissue consisting of a dense subepithelial band. The dense band, composed mainly of collagen fibre bundles, along with some lymphocyte tubes, fibroblasts, mast cells, macrophages, and capillaries, plays a crucial role in maintaining the function and structure of the peritoneum. The peritoneal natural semipermeable membrane is responsible for ultra-filtration and solute diffusion during dialysis by converting solutes and water and removing metabolites while maintaining water and electrolyte balance. Peritoneal dialysis (PD) is a cost-effective method of dialysis and an alternative treatment for patients with end-stage renal disease. However, as the duration of peritoneal dialysis extends, it can expose problems with dialysis inadequacy and ultrafiltration failure.

Various nonphysiological factors in the dialysate, such as hyperosmolarity, hyperglycemia, low pH, glucose degradation products (GDPs), and advanced glycosylation end products (AGEs), can lead to chronic stimulation and damage of the peritoneum in PD patients. Triggers such as biological incompatibility of peritoneal dialysis solutions, uraemia toxins, and recurrent intraperitoneal inflammation initiating multiple pathways that regulate the release of various cytokines, promote the transcription of fibrosis-related genes, and deposit extracellular matrix. As a result, peritoneal fibrosis may occur. Inflammation is a frequent underlying cause of peritoneal fibrosis in patients with PD. While it can be directly induced by pathogenic microorganisms, peritoneal inflammation may also result from the accumulation of uraemia toxins, mechanical stress on blood vessel walls, ageing, and complications of diabetes.

Surgical Adhesions

An adhesion is a band of scar tissue that binds two parts of the tissue that are not normally joined together. Adhesions may appear as thin sheets of tissue similar to plastic wrap or as thick as fibrous bands. Adhesions may develop when the body's repair mechanisms respond to any tissue disturbance, such as surgery, infection, trauma, radiation, resulting in inflammation. Repair cells within the body cannot differentiate between one organ and another. If an organ undergoes repair and comes into contact with another part of itself, or another organ, scar tissue may form to connect the two surfaces.

Adhesions may cause small bowel obstructions in adults. As scar tissue begins to restrict motion of the small intestines, passing food through the digestive system may become progressively more difficult. The bowel may become blocked. In extreme cases, adhesions may form fibrous bands around a segment of the intestine. This may constrict blood flow and lead to tissue death. Pelvic adhesions may involve any organ within the pelvis, such as the uterus, ovaries, fallopian tubes, or bladder, and usually occur after surgery. Fallopian adhesions can lead to infertility and increased incidence of ectopic pregnancy in which a fertilized egg develops outside the uterus. Endometriosis may also be caused by pelvic adhesions. Pleural adhesions are adhesions that form around the lungs after pneumonia, tuberculosis, rheumatologic or autoimmune disease, or surgery. Heart adhesions may occur when scar tissue forms within the membranes that surround the heart, called the pericardial sac, thus restricting heart function. Infections, such as rheumatic arthritis, may lead to adhesions forming on heart valves and can lead to decreased heart efficiency. Treatment for adhesions vary depending on the location, extent of adhesion formation, and problems the adhesion is causing. Unless a surgical emergency becomes evident, a healthcare provider may treat symptoms rather than perform surgery.

Myelofibrosis

Myelofibrosis is a rare type of blood cancer where the bone marrow is replaced by fibrous scar tissue. Myelofibrosis is a form of chronic leukemia and a myeloproliferative disorder. Myeloproliferative disorders involve too many blood cells being made in the bone marrow where blood cells are produced. In myelofibrosis, a mutation in a stem cell's DNA may cause the cell to become defective, or a cancer cell. The cell multiplies, passing the mutation on to new cells. Over time, more abnormal cancer cells may be produced. Some of these cells may create inflammation that causes scar tissue to form in the bone marrow. The scarring and the excess cancer cells can prevent the bone marrow from making healthy blood cells.

The abnormal blood cell production associated with myelofibrosis can lead to a variety of conditions, including anemia, thrombocytopenia, splenomegaly, extramedullary hematopoiesis, and portal hypertension. In about 12% of all cases, primary myelofibrosis progresses to acute myeloid leukemia, a very aggressive form of blood cancer. Myelofibrosis symptoms may include fatigue, fever, itching, pale skin, weight loss, night sweats, bone or joint pain, frequent infections, enlarged spleen or liver, unexplained blood clots, abnormal bleeding or bruising, enlarged veins in the stomach or esophagus which may rupture and cause bleeding. Medications that are approved for treating intermediate or high-risk myelofibrosis may include fedratinib, momelotinib, or ruxolitinib.

Chronic Myelogenous Leukemia

Chronic myelogenous leukemia, or CML, is cancer of the bone marrow. CML causes an increased number of white blood cells in the blood. When CML symptoms occur, they may include bone pain, bleeding easily, feeling full after eating a small amount of food, fatigue, fever, unintended weight loss, loss of appetite, pain or fullness below the ribs on the left side of the body, excessive sweating during sleep, and blurry vision caused by bleeding in the back of the eye.

CML may occur when chromosomes swap sections with each other. A section of chromosome 9 switches places with a section of chromosome 22 and an extra-long chromosome 9. The extra-short chromosome 22 is called the Philadelphia chromosome, and it is present in the blood cells of 90% of people with chronic myelogenous leukemia. Genes from chromosome 9 may combine with genes from chromosome 22 to create a new gene called BCR-ABL. The BCR-ABL gene tells blood cells to produce too much of a chimeric protein that is a tyrosine kinase. This chimeric tyrosine kinase can promote cancer by allowing certain blood cells to grow out of control. Blood cells may begin growing in the bone marrow. In CML the chimeric tyrosine kinase may allow too many white blood cells to grow. They can crowd out healthy blood cells and damage the bone marrow. Some degree of bone marrow fibrosis is present in most patients with chronic myelogenous leukemia. Advanced fibrosis is also common. For some people, treatment of CML may include chemotherapy. FDA approved treatment for CML may include imatinib mesylate or asciminib.

Myelodysplastic Syndrome

Myelodysplastic syndromes (MDS) are a group of cancers in which blood stem cells do not mature into healthy blood cells. Without enough healthy blood cells serious conditions such as anemia, frequent infections and bleeding that will not stop may occur. MDS may present with bone marrow fibrosis. The presence of significant marrow fibrosis has been shown to be a poor prognostic factor in patients with MDS. Fibrosis may be associated with higher transfusion requirements, multilineage dysplasia, and an increased rate of leukaemic transformation.

MDS may occur without any symptoms. Low levels of red blood cells are the most common symptom of myelodysplastic syndrome. However, other symptoms that may occur in myelodysplastic syndrome may include dyspnea, fatigue, pale skin, bruising or bleeding more often than usual, petechiae, or pinpoint-sized spots of bleeding under the skin, and frequent infections and fevers. Treatment for MDS may include blood transfusion, erythropoiesis-stimulating agents, antibiotics, chemotherapy, immunosuppressive therapy, and stem cell transplant. FDA approved treatment for MDS may include decitabine and cedazuridine or ivosidenib.

Rheumatoid Arthritis

Rheumatoid arthritis (RA) is a chronic autoimmune disease. RA occurs in the joints on both sides of the body. In RA, people may experience symptoms of pain and inflammation in the fingers, hands, wrists, knees, ankles, feet, and toes. In RA uncontrolled inflammation may damage cartilage, which normally acts as a shock absorber in the joints. Over time, the inflammation in the joints can deform the joints and eventually, the bone may erode. This can lead to fusion of the joint. Immune cells are produced in the joints and can circulate and cause symptoms throughout the body. In addition to affecting the joints, RA may affect other parts of the body, including the skin, eyes, mouth, lungs, and heart. Over time, inflammation from RA may lead to pulmonary fibrosis.

Symptoms of RA may include pain, swelling, stiffness and tenderness in more than one joint, stiffness, especially in the morning or after sitting for long periods, pain and stiffness in the same joints on both sides of the body, fatigue, weakness, and fever. Treatment goals for RA are to reduce joint pain and swelling, maintain or improve joint function, and to slow or stop joint damage. FDA approved treatments for RA include upadacitinib, baricitinib, sarilumab, and tofacitinib.

Systemic Lupus Erythematosus

Systemic lupus erythematosus (SLE), or lupus, is an autoimmune disease that causes inflammation throughout the body, which can affect the skin, joints, blood, and organs, such as the kidneys, lungs, and heart. People with SLE may experience symptoms throughout the body depending on where the autoimmune system damages tissue, including in the skin, blood, joints, kidneys, brain, heart, and lungs.

SLE symptoms usually come and go in waves called flare-ups. During a flare up, the symptoms can be severe enough to affect the person's daily routine. There may also be periods of remission where the person has mild or no symptoms. SLE symptoms usually develop slowly. The most common symptoms may include joint pain, muscle pain, or chest pain, headaches, rashes, fever, hair loss, mouth sores, fatigue, shortness of breath, swollen glands, swelling in the arms, legs, or on the face, confusion, and blood clots. SLE can sometimes cause other health conditions or issues, including photosensitivity, dry eye, depression, seizures, anemia, Raynaud's syndrome, osteoporosis, heart disease, kidney disease, and myelofibrosis. FDA approved treatment for SLE may include anifrolumab-fnia.

Memantine has been approved by FDA for the treatment of memory loss in Alzheimer's disease, a neurodegenerative disorder of the nervous system. This approval was based on three randomized placebo-controlled trials that showed significant improvements in cognitive, functional and global endpoints in this population (Tariot et al., JAMA. 2004; 291:317-24, Reisberg et al, N Engl J Med., April 3; 348 (14): 1333-41 (2003), Winblad et al., Int J Geriatr Psychiatry, 14 (2): 135-46 (1999)). Similar results were seen in two trials in vascular dementia (Wilcock et al., Int Clin Psychopharmacol., 17 (6): 297-305 (2002), Orgogozo et al., Stroke, 33:1834-9 (2002)). Memantine has been used in Germany for a variety of neurological syndromes and cognitive deficits since 1982 with good tolerability. In animal models, memantine has been shown to prolong the duration of long term potentiation in vivo and to improve learning and memory. (Zajaczkowski et al., Eur J Pharmacol., 296 (3): 239-46 (1996)).

A fibrotic expression profile analysis found seven biological pathways associated with nine fibrotic diseases (Karatzas et al., 2021).

Dupuytren's disease, unlike Alzheimer's disease, is a fibromatosis disease rather than a neurodegenerative disease. Dupuytren's disease is a systemic, chronic, fibrotic, and inflammatory disease that affects the palmar and digital fascia and causes deformities, loss of function, and pain. Dupuytren's disease may cause one or more fingers to bend toward the palm of the hand. Affected fingers may not straighten completely. Knots of tissue may form under the skin. These knots may eventually create a thick cord that can pull the fingers into a bent position. The condition gradually gets worse with time. Dupuytren's disease most often affects the two fingers farthest from the thumb. It can often occur in both hands. This can complicate everyday activities such as placing your hands in your pockets, putting on gloves or shaking hands. Dupuytren's disease can cause disability, loss of hand function, pain, and reduced ability to work and participate in activities. Dupuytren's disease impacts around 40 million patients across the United States and Europe alone. Ledderhose disease occurs in up to 25% of Dupuytren's patients.

Currently, there is no cure for Dupuytren's disease. There are no approved disease modifying pharmacological treatments for early and mid to moderate Dupuytren's disease and other integumentary system fibromatosis conditions. Surgery remains the standard of care. However, 85% of patients undergoing surgical procedures for Dupuytren's disease may have disease recurrence and 39% of patients may experience post-operative complications, including wound complication, site infection, incisional scar pain, and paresthesia. A new standard of care is needed to reduce disease recurrence and improve patients' quality of life post-surgical procedure in moderate to severe disease.

Because current treatments for fibromatosis conditions are often inadequate, new treatments are needed. The present disclosure addresses that need.

Effects of Adamantane Derivatives, Preferably Memantine on Integumentary System Fibromatosis Fibrotic Tissue Volume The present disclosure recognizes the effect of use of adamantane derivatives, preferably memantine on fibrotic tissue volume. In some embodiments, the fibrotic tissue volume is reduced by about 1% to about 60%. In some embodiments, the fibrotic tissue volume is reduced by about 1% to about 55%. In some embodiments, the fibrotic tissue volume is reduced by about 1% to about 50%. In some embodiments, the fibrotic tissue volume is reduced by about 1% to about 45%. In some embodiments, the fibrotic tissue volume is reduced by about 1% to about 40%. In some embodiments, the fibrotic tissue volume is reduced by about 1% to about 35%. In some embodiments, the fibrotic tissue volume is reduced by about 1% to about 30%. In some embodiments, the fibrotic tissue volume is reduced by about 1% to about 25%. In some embodiments, the fibrotic tissue volume is reduced by about 1% to about 20%. In some embodiments, the fibrotic tissue volume is reduced by about 1% to about 15%. In some embodiments, the fibrotic tissue volume is reduced by about 1% to about 10%. In some embodiments, the fibrotic tissue volume is reduced by about 1% to about 5%. In some embodiments, the fibrotic tissue volume is reduced by about 1% to about 2.5%.

The present disclosure recognizes the effect of use of adamantane derivatives, preferably memantine on fibrotic tissue volume. In some embodiments, the fibrotic tissue volume is reduced by about 5% to about 60%. In some embodiments, the fibrotic tissue volume is reduced by about 5% to about 55%. In some embodiments, the fibrotic tissue volume is reduced by about 5% to about 50%. In some embodiments, the fibrotic tissue volume is reduced by about 5% to about 45%. In some embodiments, the fibrotic tissue volume is reduced by about 5% to about 40%. In some embodiments, the fibrotic tissue volume is reduced by about 5% to about 35%. In some embodiments, the fibrotic tissue volume is reduced by about 5% to about 30%. In some embodiments, the fibrotic tissue volume is reduced by about 5% to about 25%. In some embodiments, the fibrotic tissue volume is reduced by about 5% to about 20%. In some embodiments, the fibrotic tissue volume is reduced by about 5% to about 15%. In some embodiments, the fibrotic tissue volume is reduced by about 5% to about 10%. In some embodiments, the fibrotic tissue volume is reduced by about 5% to about 7.5%.

The present disclosure recognizes the effect of use of adamantane derivatives, preferably memantine on fibrotic tissue volume. In some embodiments, the fibrotic tissue volume is reduced by about 10% to about 60%. In some embodiments, the fibrotic tissue volume is reduced by about 10% to about 55%. In some embodiments, the fibrotic tissue volume is reduced by about 10% to about 50%. In some embodiments, the fibrotic tissue volume is reduced by about 10% to about 45%. In some embodiments, the fibrotic tissue volume is reduced by about 10% to about 40%. In some embodiments, the fibrotic tissue volume is reduced by about 10% to about 35%. In some embodiments, the fibrotic tissue volume is reduced by about 10% to about 30%. In some embodiments, the fibrotic tissue volume is reduced by about 10% to about 25%. In some embodiments, the fibrotic tissue volume is reduced by about 10% to about 20%. In some embodiments, the fibrotic tissue volume is reduced by about 10% to about 15%. In some embodiments, the fibrotic tissue volume is reduced by about 10% to about 12%.

The present disclosure recognizes the effect of use of adamantane derivatives, preferably memantine on fibrotic tissue volume. In some embodiments, the fibrotic tissue volume is reduced by about 15% to about 60%. In some embodiments, the fibrotic tissue volume is reduced by about 15% to about 55%. In some embodiments, the fibrotic tissue volume is reduced by about 15% to about 50%. In some embodiments, the fibrotic tissue volume is reduced by about 15% to about 45%. In some embodiments, the fibrotic tissue volume is reduced by about 15% to about 40%. In some embodiments, the fibrotic tissue volume is reduced by about 15% to about 35%. In some embodiments, the fibrotic tissue volume is reduced by about 15% to about 30%. In some embodiments, the fibrotic tissue volume is reduced by about 15% to about 25%. In some embodiments, the fibrotic tissue volume is reduced by about 15% to about 20%. In some embodiments, the fibrotic tissue volume is reduced by about 15% to about 18%.

The present disclosure recognizes the effect of use of adamantane derivatives, preferably memantine on fibrotic tissue volume. In some embodiments, the fibrotic tissue volume is reduced by about 20% to about 60%. In some embodiments, the fibrotic tissue volume is reduced by about 20% to about 55%. In some embodiments, the fibrotic tissue volume is reduced by about 20% to about 50%. In some embodiments, the fibrotic tissue volume is reduced by about 20% to about 45%. In some embodiments, the fibrotic tissue volume is reduced by about 20% to about 40%. In some embodiments, the fibrotic tissue volume is reduced by about 20% to about 35%. In some embodiments, the fibrotic tissue volume is reduced by about 20% to about 30%. In some embodiments, the fibrotic tissue volume is reduced by about 20% to about 25%. In some embodiments, the fibrotic tissue volume is reduced by about 20% to about 22%.

The present disclosure recognizes the effect of use of adamantane derivatives, preferably memantine on fibrotic tissue volume. In some embodiments, the fibrotic tissue volume is reduced by about 25% to about 60%. In some embodiments, the fibrotic tissue volume is reduced by about 25% to about 55%. In some embodiments, the fibrotic tissue volume is reduced by about 25% to about 50%. In some embodiments, the fibrotic tissue volume is reduced by about 25% to about 45%. In some embodiments, the fibrotic tissue volume is reduced by about 25% to about 40%. In some embodiments, the fibrotic tissue volume is reduced by about 25% to about 35%. In some embodiments, the fibrotic tissue volume is reduced by about 25% to about 30%. In some embodiments, the fibrotic tissue volume is reduced by about 25% to about 28%.

The present disclosure recognizes the effect of use of adamantane derivatives, preferably memantine on fibrotic tissue volume. In some embodiments, the fibrotic tissue volume is reduced by about 30% to about 60%. In some embodiments, the fibrotic tissue volume is reduced by about 30% to about 55%. In some embodiments, the fibrotic tissue volume is reduced by about 30% to about 50%. In some embodiments, the fibrotic tissue volume is reduced by about 30% to about 45%. In some embodiments, the fibrotic tissue volume is reduced by about 30% to about 40%. In some embodiments, the fibrotic tissue volume is reduced by about 30% to about 35%. In some embodiments, the fibrotic tissue volume is reduced by about 30% to about 33%.

The present disclosure recognizes the effect of use of adamantane derivatives, preferably memantine on fibrotic tissue volume. In some embodiments, the fibrotic tissue volume is reduced by about 35% to about 60%. In some embodiments, the fibrotic tissue volume is reduced by about 35% to about 55%. In some embodiments, the fibrotic tissue volume is reduced by about 35% to about 50%. In some embodiments, the fibrotic tissue volume is reduced by about 35% to about 45%. In some embodiments, the fibrotic tissue volume is reduced by about 35% to about 40%. In some embodiments, the fibrotic tissue volume is reduced by about 35% to about 38%.

The present disclosure recognizes the effect of use of adamantane derivatives, preferably memantine on fibrotic tissue volume. In some embodiments, the fibrotic tissue volume is reduced by about 40% to about 60%. In some embodiments, the fibrotic tissue volume is reduced by about 40% to about 55%. In some embodiments, the fibrotic tissue volume is reduced by about 40% to about 50%. In some embodiments, the fibrotic tissue volume is reduced by about 40% to about 45%. In some embodiments, the fibrotic tissue volume is reduced by about 40% to about 43%.

The present disclosure recognizes the effect of use of adamantane derivatives, preferably memantine on fibrotic tissue volume. In some embodiments, the fibrotic tissue volume is reduced by about 45% to about 60%. In some embodiments, the fibrotic tissue volume is reduced by about 45% to about 55%. In some embodiments, the fibrotic tissue volume is reduced by about 45% to about 50%. In some embodiments, the fibrotic tissue volume is reduced by about 45% to about 48%.

The present disclosure recognizes the effect of use of adamantane derivatives, preferably memantine on fibrotic tissue volume. In some embodiments, the fibrotic tissue volume is reduced by about 50% to about 60%. In some embodiments, the fibrotic tissue volume is reduced by about 50% to about 55%. In some embodiments, the fibrotic tissue volume is reduced by about 50% to about 52.5%.

The present disclosure recognizes the effect of use of adamantane derivatives, preferably memantine on fibrotic tissue volume. In some embodiments, the fibrotic tissue volume is reduced by about 55% to about 60%.

The present disclosure recognizes the effect of use of adamantane derivatives, preferably memantine on fibrotic tissue volume. In some embodiments, the fibrotic tissue volume is reduced by about 1% to about 80%. In some embodiments, the fibrotic tissue volume is reduced by about 1% to about 75%. In some embodiments, the fibrotic tissue volume is reduced by about 1% to about 70%. In some embodiments, the fibrotic tissue volume is reduced by about 1% to about 65%. In some embodiments, the fibrotic tissue volume is reduced by about 1% to about 60%. In some embodiments, the fibrotic tissue volume is reduced by about 1% to about 55%. In some embodiments, the fibrotic tissue volume is reduced by about 1% to about 50%. In some embodiments, the fibrotic tissue volume is reduced by about 1% to about 45%. In some embodiments, the fibrotic tissue volume is reduced by about 1% to about 40%. In some embodiments, the fibrotic tissue volume is reduced by about 1% to about 35%. In some embodiments, the fibrotic tissue volume is reduced by about 1% to about 30%. In some embodiments, the fibrotic tissue volume is reduced by about 1% to about 25%. In some embodiments, the fibrotic tissue volume is reduced by about 1% to about 20%. In some embodiments, the fibrotic tissue volume is reduced by about 1% to about 15%. In some embodiments, the fibrotic tissue volume is reduced by about 1% to about 10%. In some embodiments, the fibrotic tissue volume is reduced by about 1% to about 5%.

The present disclosure recognizes the effect of use of adamantane derivatives, preferably memantine on fibrotic tissue volume. In some embodiments, the fibrotic tissue volume is reduced by about 5% to about 80%. In some embodiments, the fibrotic tissue volume is reduced by about 5% to about 75%. In some embodiments, the fibrotic tissue volume is reduced by about 5% to about 70%. In some embodiments, the fibrotic tissue volume is reduced by about 5% to about 65%. In some embodiments, the fibrotic tissue volume is reduced by about 5% to about 60%. In some embodiments, the fibrotic tissue volume is reduced by about 5% to about 55%. In some embodiments, the fibrotic tissue volume is reduced by about 5% to about 50%. In some embodiments, the fibrotic tissue volume is reduced by about 5% to about 45%. In some embodiments, the fibrotic tissue volume is reduced by about 5% to about 40%. In some embodiments, the fibrotic tissue volume is reduced by about 5% to about 35%. In some embodiments, the fibrotic tissue volume is reduced by about 5% to about 30%. In some embodiments, the fibrotic tissue volume is reduced by about 5% to about 25%. In some embodiments, the fibrotic tissue volume is reduced by about 5% to about 20%. In some embodiments, the fibrotic tissue volume is reduced by about 5% to about 15%. In some embodiments, the fibrotic tissue volume is reduced by about 5% to about 10%. In some embodiments, the fibrotic tissue volume is reduced by about 5% to about 7.5%.

The present disclosure recognizes the effect of use of adamantane derivatives, preferably memantine on fibrotic tissue volume. In some embodiments, the fibrotic tissue volume is reduced by about 10% to about 80%. In some embodiments, the fibrotic tissue volume is reduced by about 10% to about 75%. In some embodiments, the fibrotic tissue volume is reduced by about 10% to about 70%. In some embodiments, the fibrotic tissue volume is reduced by about 10% to about 65%. In some embodiments, the fibrotic tissue volume is reduced by about 10% to about 60%. In some embodiments, the fibrotic tissue volume is reduced by about 10% to about 55%. In some embodiments, the fibrotic tissue volume is reduced by about 10% to about 50%. In some embodiments, the fibrotic tissue volume is reduced by about 10% to about 45%. In some embodiments, the fibrotic tissue volume is reduced by about 10% to about 40%. In some embodiments, the fibrotic tissue volume is reduced by about 10% to about 35%. In some embodiments, the fibrotic tissue volume is reduced by about 10% to about 30%. In some embodiments, the fibrotic tissue volume is reduced by about 10% to about 25%. In some embodiments, the fibrotic tissue volume is reduced by about 10% to about 20%. In some embodiments, the fibrotic tissue volume is reduced by about 10% to about 15%. In some embodiments, the fibrotic tissue volume is reduced by about 10% to about 12.5%.

The present disclosure recognizes the effect of use of adamantane derivatives, preferably memantine on fibrotic tissue volume. In some embodiments, the fibrotic tissue volume is reduced by about 15% to about 80%. In some embodiments, the fibrotic tissue volume is reduced by about 15% to about 75%. In some embodiments, the fibrotic tissue volume is reduced by about 15% to about 70%. In some embodiments, the fibrotic tissue volume is reduced by about 15% to about 65%. In some embodiments, the fibrotic tissue volume is reduced by about 15% to about 60%. In some embodiments, the fibrotic tissue volume is reduced by about 15% to about 55%. In some embodiments, the fibrotic tissue volume is reduced by about 15% to about 50%. In some embodiments, the fibrotic tissue volume is reduced by about 15% to about 45%. In some embodiments, the fibrotic tissue volume is reduced by about 15% to about 40%. In some embodiments, the fibrotic tissue volume is reduced by about 15% to about 35%. In some embodiments, the fibrotic tissue volume is reduced by about 15% to about 30%. In some embodiments, the fibrotic tissue volume is reduced by about 15% to about 25%. In some embodiments, the fibrotic tissue volume is reduced by about 15% to about 20%. In some embodiments, the fibrotic tissue volume is reduced by about 15% to about 17.5%.

The present disclosure recognizes the effect of use of adamantane derivatives, preferably memantine on fibrotic tissue volume. In some embodiments, the fibrotic tissue volume is reduced by about 20% to about 80%. In some embodiments, the fibrotic tissue volume is reduced by about 20% to about 75%. In some embodiments, the fibrotic tissue volume is reduced by about 20% to about 70%. In some embodiments, the fibrotic tissue volume is reduced by about 20% to about 65%. In some embodiments, the fibrotic tissue volume is reduced by about 20% to about 60%. In some embodiments, the fibrotic tissue volume is reduced by about 20% to about 55%. In some embodiments, the fibrotic tissue volume is reduced by about 20% to about 50%. In some embodiments, the fibrotic tissue volume is reduced by about 20% to about 45%. In some embodiments, the fibrotic tissue volume is reduced by about 20% to about 40%. In some embodiments, the fibrotic tissue volume is reduced by about 20% to about 35%. In some embodiments, the fibrotic tissue volume is reduced by about 20% to about 30%. In some embodiments, the fibrotic tissue volume is reduced by about 20% to about 25%. In some embodiments, the fibrotic tissue volume is reduced by about 20% to about 22.5%.

The present disclosure recognizes the effect of use of adamantane derivatives, preferably memantine on fibrotic tissue volume. In some embodiments, the fibrotic tissue volume is reduced by about 25% to about 80%. In some embodiments, the fibrotic tissue volume is reduced by about 25% to about 75%. In some embodiments, the fibrotic tissue volume is reduced by about 25% to about 70%. In some embodiments, the fibrotic tissue volume is reduced by about 25% to about 65%. In some embodiments, the fibrotic tissue volume is reduced by about 25% to about 60%. In some embodiments, the fibrotic tissue volume is reduced by about 25% to about 55%. In some embodiments, the fibrotic tissue volume is reduced by about 25% to about 50%. In some embodiments, the fibrotic tissue volume is reduced by about 25% to about 45%. In some embodiments, the fibrotic tissue volume is reduced by about 25% to about 40%. In some embodiments, the fibrotic tissue volume is reduced by about 25% to about 35%. In some embodiments, the fibrotic tissue volume is reduced by about 25% to about 30%. In some embodiments, the fibrotic tissue volume is reduced by about 25% to about 27.5%.

The present disclosure recognizes the effect of use of adamantane derivatives, preferably memantine on fibrotic tissue volume. In some embodiments, the fibrotic tissue volume is reduced by about 30% to about 80%. In some embodiments, the fibrotic tissue volume is reduced by about 30% to about 75%. In some embodiments, the fibrotic tissue volume is reduced by about 30% to about 70%. In some embodiments, the fibrotic tissue volume is reduced by about 30% to about 65%. In some embodiments, the fibrotic tissue volume is reduced by about 30% to about 60%. In some embodiments, the fibrotic tissue volume is reduced by about 30% to about 55%. In some embodiments, the fibrotic tissue volume is reduced by about 30% to about 50%. In some embodiments, the fibrotic tissue volume is reduced by about 30% to about 45%. In some embodiments, the fibrotic tissue volume is reduced by about 30% to about 40%. In some embodiments, the fibrotic tissue volume is reduced by about 30% to about 35%. In some embodiments, the fibrotic tissue volume is reduced by about 30% to about 33%.

The present disclosure recognizes the effect of use of adamantane derivatives, preferably memantine on fibrotic tissue volume. In some embodiments, the fibrotic tissue volume is reduced by about 35% to about 80%. In some embodiments, the fibrotic tissue volume is reduced by about 35% to about 75%. In some embodiments, the fibrotic tissue volume is reduced by about 35% to about 70%. In some embodiments, the fibrotic tissue volume is reduced by about 35% to about 65%. In some embodiments, the fibrotic tissue volume is reduced by about 35% to about 60%. In some embodiments, the fibrotic tissue volume is reduced by about 35% to about 55%. In some embodiments, the fibrotic tissue volume is reduced by about 35% to about 50%. In some embodiments, the fibrotic tissue volume is reduced by about 35% to about 45%. In some embodiments, the fibrotic tissue volume is reduced by about 35% to about 40%. In some embodiments, the fibrotic tissue volume is reduced by about 35% to about 37.5%.

The present disclosure recognizes the effect of use of adamantane derivatives, preferably memantine on fibrotic tissue volume. In some embodiments, the fibrotic tissue volume is reduced by about 40% to about 80%. In some embodiments, the fibrotic tissue volume is reduced by about 40% to about 75%. In some embodiments, the fibrotic tissue volume is reduced by about 40% to about 70%. In some embodiments, the fibrotic tissue volume is reduced by about 40% to about 65%. In some embodiments, the fibrotic tissue volume is reduced by about 40% to about 60%. In some embodiments, the fibrotic tissue volume is reduced by about 40% to about 55%. In some embodiments, the fibrotic tissue volume is reduced by about 40% to about 50%. In some embodiments, the fibrotic tissue volume is reduced by about 40% to about 45%. In some embodiments, the fibrotic tissue volume is reduced by about 40% to about 42.5%.

The present disclosure recognizes the effect of use of adamantane derivatives, preferably memantine on fibrotic tissue volume. In some embodiments, the fibrotic tissue volume is reduced by about 45% to about 80%. In some embodiments, the fibrotic tissue volume is reduced by about 45% to about 75%. In some embodiments, the fibrotic tissue volume is reduced by about 45% to about 70%. In some embodiments, the fibrotic tissue volume is reduced by about 45% to about 65%. In some embodiments, the fibrotic tissue volume is reduced by about 45% to about 60%. In some embodiments, the fibrotic tissue volume is reduced by about 45% to about 55%. In some embodiments, the fibrotic tissue volume is reduced by about 45% to about 50%. In some embodiments, the fibrotic tissue volume is reduced by about 45% to about 47.5%.

The present disclosure recognizes the effect of use of adamantane derivatives, preferably memantine on fibrotic tissue volume. In some embodiments, the fibrotic tissue volume is reduced by about 50% to about 80%. In some embodiments, the fibrotic tissue volume is reduced by about 50% to about 75%. In some embodiments, the fibrotic tissue volume is reduced by about 50% to about 70%. In some embodiments, the fibrotic tissue volume is reduced by about 50% to about 65%. In some embodiments, the fibrotic tissue volume is reduced by about 50% to about 60%. In some embodiments, the fibrotic tissue volume is reduced by about 50% to about 55%. In some embodiments, the fibrotic tissue volume is reduced by about 50% to about 52.5%.

The present disclosure recognizes the effect of use of adamantane derivatives, preferably memantine on fibrotic tissue volume. In some embodiments, the fibrotic tissue volume is reduced by about 55% to about 80%. In some embodiments, the fibrotic tissue volume is reduced by about 55% to about 75%. In some embodiments, the fibrotic tissue volume is reduced by about 55% to about 70%. In some embodiments, the fibrotic tissue volume is reduced by about 55% to about 65%. In some embodiments, the fibrotic tissue volume is reduced by about 55% to about 60%. In some embodiments, the fibrotic tissue volume is reduced by about 55% to about 57.5%.

The present disclosure recognizes the effect of use of adamantane derivatives, preferably memantine on fibrotic tissue volume. In some embodiments, the fibrotic tissue volume is reduced by about 60% to about 80%. In some embodiments, the fibrotic tissue volume is reduced by about 60% to about 75%. In some embodiments, the fibrotic tissue volume is reduced by about 60% to about 70%. In some embodiments, the fibrotic tissue volume is reduced by about 60% to about 65%. In some embodiments, the fibrotic tissue volume is reduced by about 60% to about 62.5%.

Fibrotic Tissue Dermal Fibrosis Area

The present disclosure recognizes the effect of use of adamantane derivatives, preferably memantine on fibrotic tissue dermal fibrosis area. In some embodiments, the fibrotic tissue dermal fibrosis area is reduced by about 1% to about 80%. In some embodiments, the fibrotic tissue dermal fibrosis area is reduced by about 1% to about 75%. In some embodiments, the fibrotic tissue dermal fibrosis area is reduced by about 1% to about 70%. In some embodiments, the fibrotic tissue dermal fibrosis area is reduced by about 1% to about 65%. In some embodiments, the fibrotic tissue dermal fibrosis area is reduced by about 1% to about 60%. In some embodiments, the fibrotic tissue dermal fibrosis area is reduced by about 1% to about 55%. In some embodiments, the fibrotic tissue dermal fibrosis area is reduced by about 1% to about 50%. In some embodiments, the fibrotic tissue dermal fibrosis area is reduced by about 1% to about 45%. In some embodiments, the fibrotic tissue dermal fibrosis area is reduced by about 1% to about 40%. In some embodiments, the fibrotic tissue dermal fibrosis area is reduced by about 1% to about 35%. In some embodiments, the fibrotic tissue dermal fibrosis area is reduced by about 1% to about 30%. In some embodiments, the fibrotic tissue dermal fibrosis area is reduced by about 1% to about 25%. In some embodiments, the fibrotic tissue dermal fibrosis area is reduced by about 1% to about 20%. In some embodiments, the fibrotic tissue dermal fibrosis area is reduced by about 1% to about 15%. In some embodiments, the fibrotic tissue dermal fibrosis area is reduced by about 1% to about 10%. In some embodiments, the fibrotic tissue dermal fibrosis area is reduced by about 1% to about 5%.

The present disclosure recognizes the effect of use of adamantane derivatives, preferably memantine on fibrotic tissue dermal fibrosis area. In some embodiments, the fibrotic tissue dermal fibrosis area is reduced by about 5% to about 80%. In some embodiments, the fibrotic tissue dermal fibrosis area is reduced by about 5% to about 75%. In some embodiments, the fibrotic tissue dermal fibrosis area is reduced by about 5% to about 70%. In some embodiments, the fibrotic tissue dermal fibrosis area is reduced by about 5% to about 65%. In some embodiments, the fibrotic tissue dermal fibrosis area is reduced by about 5% to about 60%. In some embodiments, the fibrotic tissue dermal fibrosis area is reduced by about 5% to about 55%. In some embodiments, the fibrotic tissue dermal fibrosis area is reduced by about 5% to about 50%. In some embodiments, the fibrotic tissue dermal fibrosis area is reduced by about 5% to about 45%. In some embodiments, the fibrotic tissue dermal fibrosis area is reduced by about 5% to about 40%. In some embodiments, the fibrotic tissue dermal fibrosis area is reduced by about 5% to about 35%. In some embodiments, the fibrotic tissue dermal fibrosis area is reduced by about 5% to about 30%. In some embodiments, the fibrotic tissue dermal fibrosis area is reduced by about 5% to about 25%. In some embodiments, the fibrotic tissue dermal fibrosis area is reduced by about 5% to about 20%. In some embodiments, the fibrotic tissue dermal fibrosis area is reduced by about 5% to about 15%. In some embodiments, the fibrotic tissue dermal fibrosis area is reduced by about 5% to about 10%. In some embodiments, the fibrotic tissue dermal fibrosis area is reduced by about 5% to about 7.5%.

The present disclosure recognizes the effect of use of adamantane derivatives, preferably memantine on fibrotic tissue dermal fibrosis area. In some embodiments, the fibrotic tissue dermal fibrosis area is reduced by about 10% to about 80%. In some embodiments, the fibrotic tissue dermal fibrosis area is reduced by about 10% to about 75%. In some embodiments, the fibrotic tissue dermal fibrosis area is reduced by about 10% to about 70%. In some embodiments, the fibrotic tissue dermal fibrosis area is reduced by about 10% to about 65%. In some embodiments, the fibrotic tissue dermal fibrosis area is reduced by about 10% to about 60%. In some embodiments, the fibrotic tissue dermal fibrosis area is reduced by about 10% to about 55%. In some embodiments, the fibrotic tissue dermal fibrosis area is reduced by about 10% to about 50%. In some embodiments, the fibrotic tissue dermal fibrosis area is reduced by about 10% to about 45%. In some embodiments, the fibrotic tissue dermal fibrosis area is reduced by about 10% to about 40%. In some embodiments, the fibrotic tissue dermal fibrosis area is reduced by about 10% to about 35%. In some embodiments, the fibrotic tissue dermal fibrosis area is reduced by about 10% to about 30%. In some embodiments, the fibrotic tissue dermal fibrosis area is reduced by about 10% to about 25%. In some embodiments, the fibrotic tissue dermal fibrosis area is reduced by about 10% to about 20%. In some embodiments, the fibrotic tissue dermal fibrosis area is reduced by about 10% to about 15%. In some embodiments, the fibrotic tissue dermal fibrosis area is reduced by about 10% to about 12.5%.

The present disclosure recognizes the effect of use of adamantane derivatives, preferably memantine on fibrotic tissue dermal fibrosis area. In some embodiments, the fibrotic tissue dermal fibrosis area is reduced by about 15% to about 80%. In some embodiments, the fibrotic tissue dermal fibrosis area is reduced by about 15% to about 75%. In some embodiments, the fibrotic tissue dermal fibrosis area is reduced by about 15% to about 70%. In some embodiments, the fibrotic tissue dermal fibrosis area is reduced by about 15% to about 65%. In some embodiments, the fibrotic tissue dermal fibrosis area is reduced by about 15% to about 60%. In some embodiments, the fibrotic tissue dermal fibrosis area is reduced by about 15% to about 55%. In some embodiments, the fibrotic tissue dermal fibrosis area is reduced by about 15% to about 50%. In some embodiments, the fibrotic tissue dermal fibrosis area is reduced by about 15% to about 45%. In some embodiments, the fibrotic tissue dermal fibrosis area is reduced by about 15% to about 40%. In some embodiments, the fibrotic tissue dermal fibrosis area is reduced by about 15% to about 35%. In some embodiments, the fibrotic tissue dermal fibrosis area is reduced by about 15% to about 30%. In some embodiments, the fibrotic tissue dermal fibrosis area is reduced by about 15% to about 25%. In some embodiments, the fibrotic tissue dermal fibrosis area is reduced by about 15% to about 20%. In some embodiments, the fibrotic tissue dermal fibrosis area is reduced by about 15% to about 17.5%.

The present disclosure recognizes the effect of use of adamantane derivatives, preferably memantine on fibrotic tissue dermal fibrosis area. In some embodiments, the fibrotic tissue dermal fibrosis area is reduced by about 20% to about 80%. In some embodiments, the fibrotic tissue dermal fibrosis area is reduced by about 20% to about 75%. In some embodiments, the fibrotic tissue dermal fibrosis area is reduced by about 20% to about 70%. In some embodiments, the fibrotic tissue dermal fibrosis area is reduced by about 20% to about 65%. In some embodiments, the fibrotic tissue dermal fibrosis area is reduced by about 20% to about 60%. In some embodiments, the fibrotic tissue dermal fibrosis area is reduced by about 20% to about 55%. In some embodiments, the fibrotic tissue dermal fibrosis area is reduced by about 20% to about 50%. In some embodiments, the fibrotic tissue dermal fibrosis area is reduced by about 20% to about 45%. In some embodiments, the fibrotic tissue dermal fibrosis area is reduced by about 20% to about 40%. In some embodiments, the fibrotic tissue dermal fibrosis area is reduced by about 20% to about 35%. In some embodiments, the fibrotic tissue dermal fibrosis area is reduced by about 20% to about 30%. In some embodiments, the fibrotic tissue dermal fibrosis area is reduced by about 20% to about 25%. In some embodiments, the fibrotic tissue dermal fibrosis area is reduced by about 20% to about 22.5%.

The present disclosure recognizes the effect of use of adamantane derivatives, preferably memantine on fibrotic tissue dermal fibrosis area. In some embodiments, the fibrotic tissue dermal fibrosis area is reduced by about 25% to about 80%. In some embodiments, the fibrotic tissue dermal fibrosis area is reduced by about 25% to about 75%. In some embodiments, the fibrotic tissue dermal fibrosis area is reduced by about 25% to about 70%. In some embodiments, the fibrotic tissue dermal fibrosis area is reduced by about 25% to about 65%. In some embodiments, the fibrotic tissue dermal fibrosis area is reduced by about 25% to about 60%. In some embodiments, the fibrotic tissue dermal fibrosis area is reduced by about 25% to about 55%. In some embodiments, the fibrotic tissue dermal fibrosis area is reduced by about 25% to about 50%. In some embodiments, the fibrotic tissue dermal fibrosis area is reduced by about 25% to about 45%. In some embodiments, the fibrotic tissue dermal fibrosis area is reduced by about 25% to about 40%. In some embodiments, the fibrotic tissue dermal fibrosis area is reduced by about 25% to about 35%. In some embodiments, the fibrotic tissue dermal fibrosis area is reduced by about 25% to about 30%. In some embodiments, the fibrotic tissue dermal fibrosis area is reduced by about 25% to about 27.5%.

The present disclosure recognizes the effect of use of adamantane derivatives, preferably memantine on fibrotic tissue dermal fibrosis area. In some embodiments, the fibrotic tissue dermal fibrosis area is reduced by about 30% to about 80%. In some embodiments, the fibrotic tissue dermal fibrosis area is reduced by about 30% to about 75%. In some embodiments, the fibrotic tissue dermal fibrosis area is reduced by about 30% to about 70%. In some embodiments, the fibrotic tissue dermal fibrosis area is reduced by about 30% to about 65%. In some embodiments, the fibrotic tissue dermal fibrosis area is reduced by about 30% to about 60%. In some embodiments, the fibrotic tissue dermal fibrosis area is reduced by about 30% to about 55%. In some embodiments, the fibrotic tissue dermal fibrosis area is reduced by about 30% to about 50%. In some embodiments, the fibrotic tissue dermal fibrosis area is reduced by about 30% to about 45%. In some embodiments, the fibrotic tissue dermal fibrosis area is reduced by about 30% to about 40%. In some embodiments, the fibrotic tissue dermal fibrosis area is reduced by about 30% to about 35%. In some embodiments, the fibrotic tissue dermal fibrosis area is reduced by about 30% to about 32.5%.

The present disclosure recognizes the effect of use of adamantane derivatives, preferably memantine on fibrotic tissue dermal fibrosis area. In some embodiments, the fibrotic tissue dermal fibrosis area is reduced by about 35% to about 80%. In some embodiments, the fibrotic tissue dermal fibrosis area is reduced by about 35% to about 75%. In some embodiments, the fibrotic tissue dermal fibrosis area is reduced by about 35% to about 70%. In some embodiments, the fibrotic tissue dermal fibrosis area is reduced by about 35% to about 65%. In some embodiments, the fibrotic tissue dermal fibrosis area is reduced by about 35% to about 60%. In some embodiments, the fibrotic tissue dermal fibrosis area is reduced by about 35% to about 55%. In some embodiments, the fibrotic tissue dermal fibrosis area is reduced by about 35% to about 50%. In some embodiments, the fibrotic tissue dermal fibrosis area is reduced by about 35% to about 45%. In some embodiments, the fibrotic tissue dermal fibrosis area is reduced by about 35% to about 40%. In some embodiments, the fibrotic tissue dermal fibrosis area is reduced by about 35% to about 37.5%.

The present disclosure recognizes the effect of use of adamantane derivatives, preferably memantine on fibrotic tissue dermal fibrosis area. In some embodiments, the fibrotic tissue dermal fibrosis area is reduced by about 40% to about 80%. In some embodiments, the fibrotic tissue dermal fibrosis area is reduced by about 40% to about 75%. In some embodiments, the fibrotic tissue dermal fibrosis area is reduced by about 40% to about 70%. In some embodiments, the fibrotic tissue dermal fibrosis area is reduced by about 40% to about 65%. In some embodiments, the fibrotic tissue dermal fibrosis area is reduced by about 40% to about 60%. In some embodiments, the fibrotic tissue dermal fibrosis area is reduced by about 40% to about 55%. In some embodiments, the fibrotic tissue dermal fibrosis area is reduced by about 40% to about 50%. In some embodiments, the fibrotic tissue dermal fibrosis area is reduced by about 40% to about 45%. In some embodiments, the fibrotic tissue dermal fibrosis area is reduced by about 40% to about 42.5%.

The present disclosure recognizes the effect of use of adamantane derivatives, preferably memantine on fibrotic tissue dermal fibrosis area. In some embodiments, the fibrotic tissue dermal fibrosis area is reduced by about 45% to about 80%. In some embodiments, the fibrotic tissue dermal fibrosis area is reduced by about 45% to about 75%. In some embodiments, the fibrotic tissue dermal fibrosis area is reduced by about 45% to about 70%. In some embodiments, the fibrotic tissue dermal fibrosis area is reduced by about 45% to about 65%. In some embodiments, the fibrotic tissue dermal fibrosis area is reduced by about 45% to about 60%. In some embodiments, the fibrotic tissue dermal fibrosis area is reduced by about 45% to about 55%. In some embodiments, the fibrotic tissue dermal fibrosis area is reduced by about 45% to about 50%. In some embodiments, the fibrotic tissue dermal fibrosis area is reduced by about 45% to about 47.5%.

The present disclosure recognizes the effect of use of adamantane derivatives, preferably memantine on fibrotic tissue dermal fibrosis area. In some embodiments, the fibrotic tissue dermal fibrosis area is reduced by about 50% to about 80%. In some embodiments, the fibrotic tissue dermal fibrosis area is reduced by about 50% to about 75%. In some embodiments, the fibrotic tissue dermal fibrosis area is reduced by about 50% to about 70%. In some embodiments, the fibrotic tissue dermal fibrosis area is reduced by about 50% to about 65%. In some embodiments, the fibrotic tissue dermal fibrosis area is reduced by about 50% to about 60%. In some embodiments, the fibrotic tissue dermal fibrosis area is reduced by about 50% to about 55%. In some embodiments, the fibrotic tissue dermal fibrosis area is reduced by about 50% to about 52.5%.

The present disclosure recognizes the effect of use of adamantane derivatives, preferably memantine on fibrotic tissue dermal fibrosis area. In some embodiments, the fibrotic tissue dermal fibrosis area is reduced by about 55% to about 80%. In some embodiments, the fibrotic tissue dermal fibrosis area is reduced by about 55% to about 75%. In some embodiments, the fibrotic tissue dermal fibrosis area is reduced by about 55% to about 70%. In some embodiments, the fibrotic tissue dermal fibrosis area is reduced by about 55% to about 65%. In some embodiments, the fibrotic tissue dermal fibrosis area is reduced by about 55% to about 60%. In some embodiments, the fibrotic tissue dermal fibrosis area is reduced by about 55% to about 57.5%.

The present disclosure recognizes the effect of use of adamantane derivatives, preferably memantine on fibrotic tissue dermal fibrosis area. In some embodiments, the fibrotic tissue dermal fibrosis area is reduced by about 60% to about 80%. In some embodiments, the fibrotic tissue dermal fibrosis area is reduced by about 60% to about 75%. In some embodiments, the fibrotic tissue dermal fibrosis area is reduced by about 60% to about 70%. In some embodiments, the fibrotic tissue dermal fibrosis area is reduced by about 60% to about 65%. In some embodiments, the fibrotic tissue dermal fibrosis area is reduced by about 60% to about 62.5%.

The present disclosure recognizes the effect of use of adamantane derivatives, preferably memantine on fibrotic tissue dermal fibrosis area. In some embodiments, the fibrotic tissue dermal fibrosis area is reduced by about 65% to about 80%. In some embodiments, the fibrotic tissue dermal fibrosis area is reduced by about 65% to about 75%. In some embodiments, the fibrotic tissue dermal fibrosis area is reduced by about 65% to about 70%. In some embodiments, the fibrotic tissue dermal fibrosis area is reduced by about 65% to about 67.5%.

The present disclosure recognizes the effect of use of adamantane derivatives, preferably memantine on fibrotic tissue dermal fibrosis area. In some embodiments, the fibrotic tissue dermal fibrosis area is reduced by about 70% to about 80%. In some embodiments, the fibrotic tissue dermal fibrosis area is reduced by about 70% to about 75%. In some embodiments, the fibrotic tissue dermal fibrosis area is reduced by about 70% to about 72.5%.

The present disclosure recognizes the effect of use of adamantane derivatives, preferably memantine on fibrotic tissue dermal fibrosis area. In some embodiments, the fibrotic tissue dermal fibrosis area is reduced by about 75% to about 80%. In some embodiments, the fibrotic tissue dermal fibrosis area is reduced by about 75% to about 77.5%.

Fibrotic Tissue Dermal Fibrosis Percent

The present disclosure recognizes the effect of use of adamantane derivatives, preferably memantine on fibrotic tissue dermal fibrosis percent. In some embodiments, the fibrotic tissue dermal fibrosis percent is reduced by about 1% to about 90%. In some embodiments, the fibrotic tissue dermal fibrosis percent is reduced by about 1% to about 85%. In some embodiments, the fibrotic tissue dermal fibrosis percent is reduced by about 1% to about 80%. In some embodiments, the fibrotic tissue dermal fibrosis percent is reduced by about 1% to about 75%. In some embodiments, the fibrotic tissue dermal fibrosis percent is reduced by about 1% to about 70%. In some embodiments, the fibrotic tissue dermal fibrosis percent is reduced by about 1% to about 65%. In some embodiments, the fibrotic tissue dermal fibrosis percent is reduced by about 1% to about 60%. In some embodiments, the fibrotic tissue dermal fibrosis percent is reduced by about 1% to about 55%. In some embodiments, the fibrotic tissue dermal fibrosis percent is reduced by about 1% to about 50%. In some embodiments, the fibrotic tissue dermal fibrosis percent is reduced by about 1% to about 45%. In some embodiments, the fibrotic tissue dermal fibrosis percent is reduced by about 1% to about 40%. In some embodiments, the fibrotic tissue dermal fibrosis percent is reduced by about 1% to about 35%. In some embodiments, the fibrotic tissue dermal fibrosis percent is reduced by about 1% to about 30%. In some embodiments, the fibrotic tissue dermal fibrosis percent is reduced by about 1% to about 25%. In some embodiments, the fibrotic tissue dermal fibrosis percent is reduced by about 1% to about 20%. In some embodiments, the fibrotic tissue dermal fibrosis percent is reduced by about 1% to about 15%. In some embodiments, the fibrotic tissue dermal fibrosis percent is reduced by about 1% to about 10%. In some embodiments, the fibrotic tissue dermal fibrosis percent is reduced by about 1% to about 5%.

The present disclosure recognizes the effect of use of adamantane derivatives, preferably memantine on fibrotic tissue dermal fibrosis percent. In some embodiments, the fibrotic tissue dermal fibrosis percent is reduced by about 5% to about 90%. In some embodiments, the fibrotic tissue dermal fibrosis percent is reduced by about 5% to about 85%. In some embodiments, the fibrotic tissue dermal fibrosis percent is reduced by about 5% to about 80%. In some embodiments, the fibrotic tissue dermal fibrosis percent is reduced by about 5% to about 75%. In some embodiments, the fibrotic tissue dermal fibrosis percent is reduced by about 5% to about 70%. In some embodiments, the fibrotic tissue dermal fibrosis percent is reduced by about 5% to about 65%. In some embodiments, the fibrotic tissue dermal fibrosis percent is reduced by about 5% to about 60%. In some embodiments, the fibrotic tissue dermal fibrosis percent is reduced by about 5% to about 55%. In some embodiments, the fibrotic tissue dermal fibrosis percent is reduced by about 5% to about 50%. In some embodiments, the fibrotic tissue dermal fibrosis percent is reduced by about 5% to about 45%. In some embodiments, the fibrotic tissue dermal fibrosis percent is reduced by about 5% to about 40%. In some embodiments, the fibrotic tissue dermal fibrosis percent is reduced by about 5% to about 35%. In some embodiments, the fibrotic tissue dermal fibrosis percent is reduced by about 5% to about 30%. In some embodiments, the fibrotic tissue dermal fibrosis percent is reduced by about 5% to about 25%. In some embodiments, the fibrotic tissue dermal fibrosis percent is reduced by about 5% to about 20%. In some embodiments, the fibrotic tissue dermal fibrosis percent is reduced by about 5% to about 15%. In some embodiments, the fibrotic tissue dermal fibrosis percent is reduced by about 5% to about 10%. In some embodiments, the fibrotic tissue dermal fibrosis percent is reduced by about 5% to about 7.5%.

The present disclosure recognizes the effect of use of adamantane derivatives, preferably memantine on fibrotic tissue dermal fibrosis percent. In some embodiments, the fibrotic tissue dermal fibrosis percent is reduced by about 10% to about 90%. In some embodiments, the fibrotic tissue dermal fibrosis percent is reduced by about 10% to about 85%. In some embodiments, the fibrotic tissue dermal fibrosis percent is reduced by about 10% to about 80%. In some embodiments, the fibrotic tissue dermal fibrosis percent is reduced by about 10% to about 75%. In some embodiments, the fibrotic tissue dermal fibrosis percent is reduced by about 10% to about 70%. In some embodiments, the fibrotic tissue dermal fibrosis percent is reduced by about 10% to about 65%. In some embodiments, the fibrotic tissue dermal fibrosis percent is reduced by about 10% to about 60%. In some embodiments, the fibrotic tissue dermal fibrosis percent is reduced by about 10% to about 55%. In some embodiments, the fibrotic tissue dermal fibrosis percent is reduced by about 10% to about 50%. In some embodiments, the fibrotic tissue dermal fibrosis percent is reduced by about 10% to about 45%. In some embodiments, the fibrotic tissue dermal fibrosis percent is reduced by about 10% to about 40%. In some embodiments, the fibrotic tissue dermal fibrosis percent is reduced by about 10% to about 35%. In some embodiments, the fibrotic tissue dermal fibrosis percent is reduced by about 10% to about 30%. In some embodiments, the fibrotic tissue dermal fibrosis percent is reduced by about 10% to about 25%. In some embodiments, the fibrotic tissue dermal fibrosis percent is reduced by about 10% to about 20%. In some embodiments, the fibrotic tissue dermal fibrosis percent is reduced by about 10% to about 15%. In some embodiments, the fibrotic tissue dermal fibrosis percent is reduced by about 10% to about 12.5%.

The present disclosure recognizes the effect of use of adamantane derivatives, preferably memantine on fibrotic tissue dermal fibrosis percent. In some embodiments, the fibrotic tissue dermal fibrosis percent is reduced by about 15% to about 90%. In some embodiments, the fibrotic tissue dermal fibrosis percent is reduced by about 15% to about 85%. In some embodiments, the fibrotic tissue dermal fibrosis percent is reduced by about 15% to about 80%. In some embodiments, the fibrotic tissue dermal fibrosis percent is reduced by about 15% to about 75%. In some embodiments, the fibrotic tissue dermal fibrosis percent is reduced by about 15% to about 70%. In some embodiments, the fibrotic tissue dermal fibrosis percent is reduced by about 15% to about 65%. In some embodiments, the fibrotic tissue dermal fibrosis percent is reduced by about 15% to about 60%. In some embodiments, the fibrotic tissue dermal fibrosis percent is reduced by about 15% to about 55%. In some embodiments, the fibrotic tissue dermal fibrosis percent is reduced by about 15% to about 50%. In some embodiments, the fibrotic tissue dermal fibrosis percent is reduced by about 15% to about 45%. In some embodiments, the fibrotic tissue dermal fibrosis percent is reduced by about 15% to about 40%. In some embodiments, the fibrotic tissue dermal fibrosis percent is reduced by about 15% to about 35%. In some embodiments, the fibrotic tissue dermal fibrosis percent is reduced by about 15% to about 30%. In some embodiments, the fibrotic tissue dermal fibrosis percent is reduced by about 15% to about 25%. In some embodiments, the fibrotic tissue dermal fibrosis percent is reduced by about 15% to about 20%. In some embodiments, the fibrotic tissue dermal fibrosis percent is reduced by about 15% to about 17.5%.

The present disclosure recognizes the effect of use of adamantane derivatives, preferably memantine on fibrotic tissue dermal fibrosis percent. In some embodiments, the fibrotic tissue dermal fibrosis percent is reduced by about 20% to about 90%. In some embodiments, the fibrotic tissue dermal fibrosis percent is reduced by about 20% to about 85%. In some embodiments, the fibrotic tissue dermal fibrosis percent is reduced by about 20% to about 80%. In some embodiments, the fibrotic tissue dermal fibrosis percent is reduced by about 20% to about 75%. In some embodiments, the fibrotic tissue dermal fibrosis percent is reduced by about 20% to about 70%. In some embodiments, the fibrotic tissue dermal fibrosis percent is reduced by about 20% to about 65%. In some embodiments, the fibrotic tissue dermal fibrosis percent is reduced by about 20% to about 60%. In some embodiments, the fibrotic tissue dermal fibrosis percent is reduced by about 20% to about 55%. In some embodiments, the fibrotic tissue dermal fibrosis percent is reduced by about 20% to about 50%. In some embodiments, the fibrotic tissue dermal fibrosis percent is reduced by about 20% to about 45%. In some embodiments, the fibrotic tissue dermal fibrosis percent is reduced by about 20% to about 40%. In some embodiments, the fibrotic tissue dermal fibrosis percent is reduced by about 20% to about 35%. In some embodiments, the fibrotic tissue dermal fibrosis percent is reduced by about 20% to about 30%. In some embodiments, the fibrotic tissue dermal fibrosis percent is reduced by about 20% to about 25%. In some embodiments, the fibrotic tissue dermal fibrosis percent is reduced by about 20% to about 22.5%.

The present disclosure recognizes the effect of use of adamantane derivatives, preferably memantine on fibrotic tissue dermal fibrosis percent. In some embodiments, the fibrotic tissue dermal fibrosis percent is reduced by about 25% to about 90%. In some embodiments, the fibrotic tissue dermal fibrosis percent is reduced by about 25% to about 85%. In some embodiments, the fibrotic tissue dermal fibrosis percent is reduced by about 25% to about 80%. In some embodiments, the fibrotic tissue dermal fibrosis percent is reduced by about 25% to about 75%. In some embodiments, the fibrotic tissue dermal fibrosis percent is reduced by about 25% to about 70%. In some embodiments, the fibrotic tissue dermal fibrosis percent is reduced by about 25% to about 65%. In some embodiments, the fibrotic tissue dermal fibrosis percent is reduced by about 25% to about 60%. In some embodiments, the fibrotic tissue dermal fibrosis percent is reduced by about 25% to about 55%. In some embodiments, the fibrotic tissue dermal fibrosis percent is reduced by about 25% to about 50%. In some embodiments, the fibrotic tissue dermal fibrosis percent is reduced by about 25% to about 45%. In some embodiments, the fibrotic tissue dermal fibrosis percent is reduced by about 25% to about 40%. In some embodiments, the fibrotic tissue dermal fibrosis percent is reduced by about 25% to about 35%. In some embodiments, the fibrotic tissue dermal fibrosis percent is reduced by about 25% to about 30%. In some embodiments, the fibrotic tissue dermal fibrosis percent is reduced by about 25% to about 27.5%.

The present disclosure recognizes the effect of use of adamantane derivatives, preferably memantine on fibrotic tissue dermal fibrosis percent. In some embodiments, the fibrotic tissue dermal fibrosis percent is reduced by about 30% to about 90%. In some embodiments, the fibrotic tissue dermal fibrosis percent is reduced by about 30% to about 85%. In some embodiments, the fibrotic tissue dermal fibrosis percent is reduced by about 30% to about 80%. In some embodiments, the fibrotic tissue dermal fibrosis percent is reduced by about 30% to about 75%. In some embodiments, the fibrotic tissue dermal fibrosis percent is reduced by about 30% to about 70%. In some embodiments, the fibrotic tissue dermal fibrosis percent is reduced by about 30% to about 65%. In some embodiments, the fibrotic tissue dermal fibrosis percent is reduced by about 30% to about 60%. In some embodiments, the fibrotic tissue dermal fibrosis percent is reduced by about 30% to about 55%. In some embodiments, the fibrotic tissue dermal fibrosis percent is reduced by about 30% to about 50%. In some embodiments, the fibrotic tissue dermal fibrosis percent is reduced by about 30% to about 45%. In some embodiments, the fibrotic tissue dermal fibrosis percent is reduced by about 30% to about 40%. In some embodiments, the fibrotic tissue dermal fibrosis percent is reduced by about 30% to about 35%. In some embodiments, the fibrotic tissue dermal fibrosis percent is reduced by about 30% to about 32.5%.

The present disclosure recognizes the effect of use of adamantane derivatives, preferably memantine on fibrotic tissue dermal fibrosis percent. In some embodiments, the fibrotic tissue dermal fibrosis percent is reduced by about 35% to about 90%. In some embodiments, the fibrotic tissue dermal fibrosis percent is reduced by about 35% to about 85%. In some embodiments, the fibrotic tissue dermal fibrosis percent is reduced by about 35% to about 80%. In some embodiments, the fibrotic tissue dermal fibrosis percent is reduced by about 35% to about 75%. In some embodiments, the fibrotic tissue dermal fibrosis percent is reduced by about 35% to about 70%. In some embodiments, the fibrotic tissue dermal fibrosis percent is reduced by about 35% to about 65%. In some embodiments, the fibrotic tissue dermal fibrosis percent is reduced by about 35% to about 60%. In some embodiments, the fibrotic tissue dermal fibrosis percent is reduced by about 35% to about 55%. In some embodiments, the fibrotic tissue dermal fibrosis percent is reduced by about 35% to about 50%. In some embodiments, the fibrotic tissue dermal fibrosis percent is reduced by about 35% to about 45%. In some embodiments, the fibrotic tissue dermal fibrosis percent is reduced by about 35% to about 40%. In some embodiments, the fibrotic tissue dermal fibrosis percent is reduced by about 35% to about 37.5%.

The present disclosure recognizes the effect of use of adamantane derivatives, preferably memantine on fibrotic tissue dermal fibrosis percent. In some embodiments, the fibrotic tissue dermal fibrosis percent is reduced by about 40% to about 90%. In some embodiments, the fibrotic tissue dermal fibrosis percent is reduced by about 40% to about 85%. In some embodiments, the fibrotic tissue dermal fibrosis percent is reduced by about 40% to about 80%. In some embodiments, the fibrotic tissue dermal fibrosis percent is reduced by about 40% to about 75%. In some embodiments, the fibrotic tissue dermal fibrosis percent is reduced by about 40% to about 70%. In some embodiments, the fibrotic tissue dermal fibrosis percent is reduced by about 40% to about 65%. In some embodiments, the fibrotic tissue dermal fibrosis percent is reduced by about 40% to about 60%. In some embodiments, the fibrotic tissue dermal fibrosis percent is reduced by about 40% to about 55%. In some embodiments, the fibrotic tissue dermal fibrosis percent is reduced by about 40% to about 50%. In some embodiments, the fibrotic tissue dermal fibrosis percent is reduced by about 40% to about 45%. In some embodiments, the fibrotic tissue dermal fibrosis percent is reduced by about 40% to about 42.5%.

The present disclosure recognizes the effect of use of adamantane derivatives, preferably memantine on fibrotic tissue dermal fibrosis percent. In some embodiments, the fibrotic tissue dermal fibrosis percent is reduced by about 45% to about 90%. In some embodiments, the fibrotic tissue dermal fibrosis percent is reduced by about 45% to about 85%. In some embodiments, the fibrotic tissue dermal fibrosis percent is reduced by about 45% to about 80%. In some embodiments, the fibrotic tissue dermal fibrosis percent is reduced by about 45% to about 75%. In some embodiments, the fibrotic tissue dermal fibrosis percent is reduced by about 45% to about 70%. In some embodiments, the fibrotic tissue dermal fibrosis percent is reduced by about 45% to about 65%. In some embodiments, the fibrotic tissue dermal fibrosis percent is reduced by about 45% to about 60%. In some embodiments, the fibrotic tissue dermal fibrosis percent is reduced by about 45% to about 55%. In some embodiments, the fibrotic tissue dermal fibrosis percent is reduced by about 45% to about 50%. In some embodiments, the fibrotic tissue dermal fibrosis percent is reduced by about 45% to about 47.5%.

The present disclosure recognizes the effect of use of adamantane derivatives, preferably memantine on fibrotic tissue dermal fibrosis percent. In some embodiments, the fibrotic tissue dermal fibrosis percent is reduced by about 50% to about 90%. In some embodiments, the fibrotic tissue dermal fibrosis percent is reduced by about 50% to about 85%. In some embodiments, the fibrotic tissue dermal fibrosis percent is reduced by about 50% to about 80%. In some embodiments, the fibrotic tissue dermal fibrosis percent is reduced by about 50% to about 75%. In some embodiments, the fibrotic tissue dermal fibrosis percent is reduced by about 50% to about 70%. In some embodiments, the fibrotic tissue dermal fibrosis percent is reduced by about 50% to about 65%. In some embodiments, the fibrotic tissue dermal fibrosis percent is reduced by about 50% to about 60%. In some embodiments, the fibrotic tissue dermal fibrosis percent is reduced by about 50% to about 55%. In some embodiments, the fibrotic tissue dermal fibrosis percent is reduced by about 50% to about 52.5%.

The present disclosure recognizes the effect of use of adamantane derivatives, preferably memantine on fibrotic tissue dermal fibrosis percent. In some embodiments, the fibrotic tissue dermal fibrosis percent is reduced by about 55% to about 90%. In some embodiments, the fibrotic tissue dermal fibrosis percent is reduced by about 55% to about 85%. In some embodiments, the fibrotic tissue dermal fibrosis percent is reduced by about 55% to about 80%. In some embodiments, the fibrotic tissue dermal fibrosis percent is reduced by about 55% to about 75%. In some embodiments, the fibrotic tissue dermal fibrosis percent is reduced by about 55% to about 70%. In some embodiments, the fibrotic tissue dermal fibrosis percent is reduced by about 55% to about 65%. In some embodiments, the fibrotic tissue dermal fibrosis percent is reduced by about 55% to about 60%. In some embodiments, the fibrotic tissue dermal fibrosis percent is reduced by about 55% to about 57.5%.

The present disclosure recognizes the effect of use of adamantane derivatives, preferably memantine on fibrotic tissue dermal fibrosis percent. In some embodiments, the fibrotic tissue dermal fibrosis percent is reduced by about 60% to about 90%. In some embodiments, the fibrotic tissue dermal fibrosis percent is reduced by about 60% to about 85%. In some embodiments, the fibrotic tissue dermal fibrosis percent is reduced by about 60% to about 80%. In some embodiments, the fibrotic tissue dermal fibrosis percent is reduced by about 60% to about 75%. In some embodiments, the fibrotic tissue dermal fibrosis percent is reduced by about 60% to about 70%. In some embodiments, the fibrotic tissue dermal fibrosis percent is reduced by about 60% to about 65%. In some embodiments, the fibrotic tissue dermal fibrosis percent is reduced by about 60% to about 62.5%.

The present disclosure recognizes the effect of use of adamantane derivatives, preferably memantine on fibrotic tissue dermal fibrosis percent. In some embodiments, the fibrotic tissue dermal fibrosis percent is reduced by about 65% to about 90%. In some embodiments, the fibrotic tissue dermal fibrosis percent is reduced by about 65% to about 85%. In some embodiments, the fibrotic tissue dermal fibrosis percent is reduced by about 65% to about 80%. In some embodiments, the fibrotic tissue dermal fibrosis percent is reduced by about 65% to about 75%. In some embodiments, the fibrotic tissue dermal fibrosis percent is reduced by about 65% to about 70%. In some embodiments, the fibrotic tissue dermal fibrosis percent is reduced by about 65% to about 67.5%.

The present disclosure recognizes the effect of use of adamantane derivatives, preferably memantine on fibrotic tissue dermal fibrosis percent. In some embodiments, the fibrotic tissue dermal fibrosis percent is reduced by about 70% to about 90%. In some embodiments, the fibrotic tissue dermal fibrosis percent is reduced by about 70% to about 85%. In some embodiments, the fibrotic tissue dermal fibrosis percent is reduced by about 70% to about 80%. In some embodiments, the fibrotic tissue dermal fibrosis percent is reduced by about 70% to about 75%. In some embodiments, the fibrotic tissue dermal fibrosis percent is reduced by about 70% to about 72.5%.

The present disclosure recognizes the effect of use of adamantane derivatives, preferably memantine on fibrotic tissue dermal fibrosis percent. In some embodiments, the fibrotic tissue dermal fibrosis percent is reduced by about 80% to about 90%. In some embodiments, the fibrotic tissue dermal fibrosis percent is reduced by about 80% to about 85%. In some embodiments, the fibrotic tissue dermal fibrosis percent is reduced by about 80% to about 82.5%.

The present disclosure recognizes the effect of use of adamantane derivatives, preferably memantine on fibrotic tissue dermal fibrosis percent. In some embodiments, the fibrotic tissue dermal fibrosis percent is reduced by about 85% to about 90%. In some embodiments, the fibrotic tissue dermal fibrosis percent is reduced by about 85% to about 87.5%.

Fibrotic Tissue Epidermal Fibrosis Area

The present disclosure recognizes the effect of use of adamantane derivatives, preferably memantine on fibrotic tissue epidermal fibrosis area. In some embodiments, the fibrotic tissue epidermal fibrosis area is reduced by about 1% to about 90%. In some embodiments, the fibrotic tissue epidermal fibrosis area is reduced by about 1% to about 85%. In some embodiments, the fibrotic tissue epidermal fibrosis area is reduced by about 1% to about 80%. In some embodiments, the fibrotic tissue epidermal fibrosis area is reduced by about 1% to about 75%. In some embodiments, the fibrotic tissue epidermal fibrosis area is reduced by about 1% to about 70%. In some embodiments, the fibrotic tissue epidermal fibrosis area is reduced by about 1% to about 65%. In some embodiments, the fibrotic tissue epidermal fibrosis area is reduced by about 1% to about 60%. In some embodiments, the fibrotic tissue epidermal fibrosis area is reduced by about 1% to about 55%. In some embodiments, the fibrotic tissue epidermal fibrosis area is reduced by about 1% to about 50%. In some embodiments, the fibrotic tissue epidermal fibrosis area is reduced by about 1% to about 45%. In some embodiments, the fibrotic tissue epidermal fibrosis area is reduced by about 1% to about 40%. In some embodiments, the fibrotic tissue epidermal fibrosis area is reduced by about 1% to about 35%. In some embodiments, the fibrotic tissue epidermal fibrosis area is reduced by about 1% to about 30%. In some embodiments, the fibrotic tissue epidermal fibrosis area is reduced by about 1% to about 25%. In some embodiments, the fibrotic tissue epidermal fibrosis area is reduced by about 1% to about 20%. In some embodiments, the fibrotic tissue epidermal fibrosis area is reduced by about 1% to about 15%. In some embodiments, the fibrotic tissue epidermal fibrosis area is reduced by about 1% to about 10%. In some embodiments, the fibrotic tissue epidermal fibrosis area is reduced by about 1% to about 5%.

The present disclosure recognizes the effect of use of adamantane derivatives, preferably memantine on fibrotic tissue epidermal fibrosis area. In some embodiments, the fibrotic tissue epidermal fibrosis area is reduced by about 5% to about 90%. In some embodiments, the fibrotic tissue epidermal fibrosis area is reduced by about 5% to about 85%. In some embodiments, the fibrotic tissue epidermal fibrosis area is reduced by about 5% to about 80%. In some embodiments, the fibrotic tissue epidermal fibrosis area is reduced by about 5% to about 75%. In some embodiments, the fibrotic tissue epidermal fibrosis area is reduced by about 5% to about 70%. In some embodiments, the fibrotic tissue epidermal fibrosis area is reduced by about 5% to about 65%. In some embodiments, the fibrotic tissue epidermal fibrosis area is reduced by about 5% to about 60%. In some embodiments, the fibrotic tissue epidermal fibrosis area is reduced by about 5% to about 55%. In some embodiments, the fibrotic tissue epidermal fibrosis area is reduced by about 5% to about 50%. In some embodiments, the fibrotic tissue epidermal fibrosis area is reduced by about 5% to about 45%. In some embodiments, the fibrotic tissue epidermal fibrosis area is reduced by about 5% to about 40%. In some embodiments, the fibrotic tissue epidermal fibrosis area is reduced by about 5% to about 35%. In some embodiments, the fibrotic tissue epidermal fibrosis area is reduced by about 5% to about 30%. In some embodiments, the fibrotic tissue epidermal fibrosis area is reduced by about 5% to about 25%. In some embodiments, the fibrotic tissue epidermal fibrosis area is reduced by about 5% to about 20%. In some embodiments, the fibrotic tissue epidermal fibrosis area is reduced by about 5% to about 15%. In some embodiments, the fibrotic tissue epidermal fibrosis area is reduced by about 5% to about 10%. In some embodiments, the fibrotic tissue epidermal fibrosis area is reduced by about 5% to about 7.5%.

The present disclosure recognizes the effect of use of adamantane derivatives, preferably memantine on fibrotic tissue epidermal fibrosis area. In some embodiments, the fibrotic tissue epidermal fibrosis area is reduced by about 10% to about 90%. In some embodiments, the fibrotic tissue epidermal fibrosis area is reduced by about 10% to about 85%. In some embodiments, the fibrotic tissue epidermal fibrosis area is reduced by about 10% to about 80%. In some embodiments, the fibrotic tissue epidermal fibrosis area is reduced by about 10% to about 75%. In some embodiments, the fibrotic tissue epidermal fibrosis area is reduced by about 10% to about 70%. In some embodiments, the fibrotic tissue epidermal fibrosis area is reduced by about 10% to about 65%. In some embodiments, the fibrotic tissue epidermal fibrosis area is reduced by about 10% to about 60%. In some embodiments, the fibrotic tissue epidermal fibrosis area is reduced by about 10% to about 55%. In some embodiments, the fibrotic tissue epidermal fibrosis area is reduced by about 10% to about 50%. In some embodiments, the fibrotic tissue epidermal fibrosis area is reduced by about 10% to about 45%. In some embodiments, the fibrotic tissue epidermal fibrosis area is reduced by about 10% to about 40%. In some embodiments, the fibrotic tissue epidermal fibrosis area is reduced by about 10% to about 35%. In some embodiments, the fibrotic tissue epidermal fibrosis area is reduced by about 10% to about 30%. In some embodiments, the fibrotic tissue epidermal fibrosis area is reduced by about 10% to about 25%. In some embodiments, the fibrotic tissue epidermal fibrosis area is reduced by about 10% to about 20%. In some embodiments, the fibrotic tissue epidermal fibrosis area is reduced by about 10% to about 15%. In some embodiments, the fibrotic tissue epidermal fibrosis area is reduced by about 10% to about 12.5%.

The present disclosure recognizes the effect of use of adamantane derivatives, preferably memantine on fibrotic tissue epidermal fibrosis area. In some embodiments, the fibrotic tissue epidermal fibrosis area is reduced by about 15% to about 90%. In some embodiments, the fibrotic tissue epidermal fibrosis area is reduced by about 15% to about 85%. In some embodiments, the fibrotic tissue epidermal fibrosis area is reduced by about 15% to about 80%. In some embodiments, the fibrotic tissue epidermal fibrosis area is reduced by about 15% to about 75%. In some embodiments, the fibrotic tissue epidermal fibrosis area is reduced by about 15% to about 70%. In some embodiments, the fibrotic tissue epidermal fibrosis area is reduced by about 15% to about 65%. In some embodiments, the fibrotic tissue epidermal fibrosis area is reduced by about 15% to about 60%. In some embodiments, the fibrotic tissue epidermal fibrosis area is reduced by about 15% to about 55%. In some embodiments, the fibrotic tissue epidermal fibrosis area is reduced by about 15% to about 50%. In some embodiments, the fibrotic tissue epidermal fibrosis area is reduced by about 15% to about 45%. In some embodiments, the fibrotic tissue epidermal fibrosis area is reduced by about 15% to about 40%. In some embodiments, the fibrotic tissue epidermal fibrosis area is reduced by about 15% to about 35%. In some embodiments, the fibrotic tissue epidermal fibrosis area is reduced by about 15% to about 30%. In some embodiments, the fibrotic tissue epidermal fibrosis area is reduced by about 15% to about 25%. In some embodiments, the fibrotic tissue epidermal fibrosis area is reduced by about 15% to about 20%. In some embodiments, the fibrotic tissue epidermal fibrosis area is reduced by about 15% to about 17.5%.

The present disclosure recognizes the effect of use of adamantane derivatives, preferably memantine on fibrotic tissue epidermal fibrosis area. In some embodiments, the fibrotic tissue epidermal fibrosis area is reduced by about 20% to about 90%. In some embodiments, the fibrotic tissue epidermal fibrosis area is reduced by about 20% to about 85%. In some embodiments, the fibrotic tissue epidermal fibrosis area is reduced by about 20% to about 80%. In some embodiments, the fibrotic tissue epidermal fibrosis area is reduced by about 20% to about 75%. In some embodiments, the fibrotic tissue epidermal fibrosis area is reduced by about 20% to about 70%. In some embodiments, the fibrotic tissue epidermal fibrosis area is reduced by about 20% to about 65%. In some embodiments, the fibrotic tissue epidermal fibrosis area is reduced by about 20% to about 60%. In some embodiments, the fibrotic tissue epidermal fibrosis area is reduced by about 20% to about 55%. In some embodiments, the fibrotic tissue epidermal fibrosis area is reduced by about 20% to about 50%. In some embodiments, the fibrotic tissue epidermal fibrosis area is reduced by about 20% to about 45%. In some embodiments, the fibrotic tissue epidermal fibrosis area is reduced by about 20% to about 40%. In some embodiments, the fibrotic tissue epidermal fibrosis area is reduced by about 20% to about 35%. In some embodiments, the fibrotic tissue epidermal fibrosis area is reduced by about 20% to about 30%. In some embodiments, the fibrotic tissue epidermal fibrosis area is reduced by about 20% to about 25%. In some embodiments, the fibrotic tissue epidermal fibrosis area is reduced by about 20% to about 22.5%.

The present disclosure recognizes the effect of use of adamantane derivatives, preferably memantine on fibrotic tissue epidermal fibrosis area. In some embodiments, the fibrotic tissue epidermal fibrosis area is reduced by about 25% to about 90%. In some embodiments, the fibrotic tissue epidermal fibrosis area is reduced by about 25% to about 85%. In some embodiments, the fibrotic tissue epidermal fibrosis area is reduced by about 25% to about 80%. In some embodiments, the fibrotic tissue epidermal fibrosis area is reduced by about 25% to about 75%. In some embodiments, the fibrotic tissue epidermal fibrosis area is reduced by about 25% to about 70%. In some embodiments, the fibrotic tissue epidermal fibrosis area is reduced by about 25% to about 65%. In some embodiments, the fibrotic tissue epidermal fibrosis area is reduced by about 25% to about 60%. In some embodiments, the fibrotic tissue epidermal fibrosis area is reduced by about 25% to about 55%. In some embodiments, the fibrotic tissue epidermal fibrosis area is reduced by about 25% to about 50%. In some embodiments, the fibrotic tissue epidermal fibrosis area is reduced by about 25% to about 45%. In some embodiments, the fibrotic tissue epidermal fibrosis area is reduced by about 25% to about 40%. In some embodiments, the fibrotic tissue epidermal fibrosis area is reduced by about 25% to about 35%. In some embodiments, the fibrotic tissue epidermal fibrosis area is reduced by about 25% to about 30%. In some embodiments, the fibrotic tissue epidermal fibrosis area is reduced by about 25% to about 27.5%.

The present disclosure recognizes the effect of use of adamantane derivatives, preferably memantine on fibrotic tissue epidermal fibrosis area. In some embodiments, the fibrotic tissue epidermal fibrosis area is reduced by about 30% to about 90%. In some embodiments, the fibrotic tissue epidermal fibrosis area is reduced by about 30% to about 85%. In some embodiments, the fibrotic tissue epidermal fibrosis area is reduced by about 30% to about 80%. In some embodiments, the fibrotic tissue epidermal fibrosis area is reduced by about 30% to about 75%. In some embodiments, the fibrotic tissue epidermal fibrosis area is reduced by about 30% to about 70%. In some embodiments, the fibrotic tissue epidermal fibrosis area is reduced by about 30% to about 65%. In some embodiments, the fibrotic tissue epidermal fibrosis area is reduced by about 30% to about 60%. In some embodiments, the fibrotic tissue epidermal fibrosis area is reduced by about 30% to about 55%. In some embodiments, the fibrotic tissue epidermal fibrosis area is reduced by about 30% to about 50%. In some embodiments, the fibrotic tissue epidermal fibrosis area is reduced by about 30% to about 45%. In some embodiments, the fibrotic tissue epidermal fibrosis area is reduced by about 30% to about 40%. In some embodiments, the fibrotic tissue epidermal fibrosis area is reduced by about 30% to about 35%. In some embodiments, the fibrotic tissue epidermal fibrosis area is reduced by about 30% to about 32.5%.

The present disclosure recognizes the effect of use of adamantane derivatives, preferably memantine on fibrotic tissue epidermal fibrosis area. In some embodiments, the fibrotic tissue epidermal fibrosis area is reduced by about 35% to about 90%. In some embodiments, the fibrotic tissue epidermal fibrosis area is reduced by about 35% to about 85%. In some embodiments, the fibrotic tissue epidermal fibrosis area is reduced by about 35% to about 80%. In some embodiments, the fibrotic tissue epidermal fibrosis area is reduced by about 35% to about 75%. In some embodiments, the fibrotic tissue epidermal fibrosis area is reduced by about 35% to about 70%. In some embodiments, the fibrotic tissue epidermal fibrosis area is reduced by about 35% to about 65%. In some embodiments, the fibrotic tissue epidermal fibrosis area is reduced by about 35% to about 60%. In some embodiments, the fibrotic tissue epidermal fibrosis area is reduced by about 35% to about 55%. In some embodiments, the fibrotic tissue epidermal fibrosis area is reduced by about 35% to about 50%. In some embodiments, the fibrotic tissue epidermal fibrosis area is reduced by about 35% to about 45%. In some embodiments, the fibrotic tissue epidermal fibrosis area is reduced by about 35% to about 40%. In some embodiments, the fibrotic tissue epidermal fibrosis area is reduced by about 35% to about 37.5%.

The present disclosure recognizes the effect of use of adamantane derivatives, preferably memantine on fibrotic tissue epidermal fibrosis area. In some embodiments, the fibrotic tissue epidermal fibrosis area is reduced by about 40% to about 90%. In some embodiments, the fibrotic tissue epidermal fibrosis area is reduced by about 40% to about 85%. In some embodiments, the fibrotic tissue epidermal fibrosis area is reduced by about 40% to about 80%. In some embodiments, the fibrotic tissue epidermal fibrosis area is reduced by about 40% to about 75%. In some embodiments, the fibrotic tissue epidermal fibrosis area is reduced by about 40% to about 70%. In some embodiments, the fibrotic tissue epidermal fibrosis area is reduced by about 40% to about 65%. In some embodiments, the fibrotic tissue epidermal fibrosis area is reduced by about 40% to about 60%. In some embodiments, the fibrotic tissue epidermal fibrosis area is reduced by about 40% to about 55%. In some embodiments, the fibrotic tissue epidermal fibrosis area is reduced by about 40% to about 50%. In some embodiments, the fibrotic tissue epidermal fibrosis area is reduced by about 40% to about 45%. In some embodiments, the fibrotic tissue epidermal fibrosis area is reduced by about 40% to about 42.5%.

The present disclosure recognizes the effect of use of adamantane derivatives, preferably memantine on fibrotic tissue epidermal fibrosis area. In some embodiments, the fibrotic tissue epidermal fibrosis area is reduced by about 45% to about 90%. In some embodiments, the fibrotic tissue epidermal fibrosis area is reduced by about 45% to about 85%. In some embodiments, the fibrotic tissue epidermal fibrosis area is reduced by about 45% to about 80%. In some embodiments, the fibrotic tissue epidermal fibrosis area is reduced by about 45% to about 75%. In some embodiments, the fibrotic tissue epidermal fibrosis area is reduced by about 45% to about 70%. In some embodiments, the fibrotic tissue epidermal fibrosis area is reduced by about 45% to about 65%. In some embodiments, the fibrotic tissue epidermal fibrosis area is reduced by about 45% to about 60%. In some embodiments, the fibrotic tissue epidermal fibrosis area is reduced by about 45% to about 55%. In some embodiments, the fibrotic tissue epidermal fibrosis area is reduced by about 45% to about 50%. In some embodiments, the fibrotic tissue epidermal fibrosis area is reduced by about 45% to about 47.5%.

The present disclosure recognizes the effect of use of adamantane derivatives, preferably memantine on fibrotic tissue epidermal fibrosis area. In some embodiments, the fibrotic tissue epidermal fibrosis area is reduced by about 50% to about 90%. In some embodiments, the fibrotic tissue epidermal fibrosis area is reduced by about 50% to about 85%. In some embodiments, the fibrotic tissue epidermal fibrosis area is reduced by about 50% to about 80%. In some embodiments, the fibrotic tissue epidermal fibrosis area is reduced by about 50% to about 75%. In some embodiments, the fibrotic tissue epidermal fibrosis area is reduced by about 50% to about 70%. In some embodiments, the fibrotic tissue epidermal fibrosis area is reduced by about 50% to about 65%. In some embodiments, the fibrotic tissue epidermal fibrosis area is reduced by about 50% to about 60%. In some embodiments, the fibrotic tissue epidermal fibrosis area is reduced by about 50% to about 55%. In some embodiments, the fibrotic tissue epidermal fibrosis area is reduced by about 50% to about 52.5%.

The present disclosure recognizes the effect of use of adamantane derivatives, preferably memantine on fibrotic tissue epidermal fibrosis area. In some embodiments, the fibrotic tissue epidermal fibrosis area is reduced by about 55% to about 90%. In some embodiments, the fibrotic tissue epidermal fibrosis area is reduced by about 55% to about 85%. In some embodiments, the fibrotic tissue epidermal fibrosis area is reduced by about 55% to about 80%. In some embodiments, the fibrotic tissue epidermal fibrosis area is reduced by about 55% to about 75%. In some embodiments, the fibrotic tissue epidermal fibrosis area is reduced by about 55% to about 70%. In some embodiments, the fibrotic tissue epidermal fibrosis area is reduced by about 55% to about 65%. In some embodiments, the fibrotic tissue epidermal fibrosis area is reduced by about 55% to about 60%. In some embodiments, the fibrotic tissue epidermal fibrosis area is reduced by about 55% to about 57.5%.

The present disclosure recognizes the effect of use of adamantane derivatives, preferably memantine on fibrotic tissue epidermal fibrosis area. In some embodiments, the fibrotic tissue epidermal fibrosis area is reduced by about 60% to about 90%. In some embodiments, the fibrotic tissue epidermal fibrosis area is reduced by about 60% to about 85%. In some embodiments, the fibrotic tissue epidermal fibrosis area is reduced by about 60% to about 80%. In some embodiments, the fibrotic tissue epidermal fibrosis area is reduced by about 60% to about 75%. In some embodiments, the fibrotic tissue epidermal fibrosis area is reduced by about 60% to about 70%. In some embodiments, the fibrotic tissue epidermal fibrosis area is reduced by about 60% to about 65%. In some embodiments, the fibrotic tissue epidermal fibrosis area is reduced by about 60% to about 62.5%.

The present disclosure recognizes the effect of use of adamantane derivatives, preferably memantine on fibrotic tissue epidermal fibrosis area. In some embodiments, the fibrotic tissue epidermal fibrosis area is reduced by about 65% to about 90%. In some embodiments, the fibrotic tissue epidermal fibrosis area is reduced by about 65% to about 85%. In some embodiments, the fibrotic tissue epidermal fibrosis area is reduced by about 65% to about 80%. In some embodiments, the fibrotic tissue epidermal fibrosis area is reduced by about 65% to about 75%. In some embodiments, the fibrotic tissue epidermal fibrosis area is reduced by about 65% to about 70%. In some embodiments, the fibrotic tissue epidermal fibrosis area is reduced by about 65% to about 67.5%.

The present disclosure recognizes the effect of use of adamantane derivatives, preferably memantine on fibrotic tissue epidermal fibrosis area. In some embodiments, the fibrotic tissue epidermal fibrosis area is reduced by about 70% to about 90%. In some embodiments, the fibrotic tissue epidermal fibrosis area is reduced by about 70% to about 85%. In some embodiments, the fibrotic tissue epidermal fibrosis area is reduced by about 70% to about 80%. In some embodiments, the fibrotic tissue epidermal fibrosis area is reduced by about 70% to about 75%. In some embodiments, the fibrotic tissue epidermal fibrosis area is reduced by about 70% to about 72.5%.

The present disclosure recognizes the effect of use of adamantane derivatives, preferably memantine on fibrotic tissue epidermal fibrosis area. In some embodiments, the fibrotic tissue epidermal fibrosis area is reduced by about 75% to about 90%. In some embodiments, the fibrotic tissue epidermal fibrosis area is reduced by about 75% to about 85%. In some embodiments, the fibrotic tissue epidermal fibrosis area is reduced by about 75% to about 80%. In some embodiments, the fibrotic tissue epidermal fibrosis area is reduced by about 75% to about 77.5%.

The present disclosure recognizes the effect of use of adamantane derivatives, preferably memantine on fibrotic tissue epidermal fibrosis area. In some embodiments, the fibrotic tissue epidermal fibrosis area is reduced by about 80% to about 90%. In some embodiments, the fibrotic tissue epidermal fibrosis area is reduced by about 80% to about 85%. In some embodiments, the fibrotic tissue epidermal fibrosis area is reduced by about 80% to about 82.5%.

The present disclosure recognizes the effect of use of adamantane derivatives, preferably memantine on fibrotic tissue epidermal fibrosis area. In some embodiments, the fibrotic tissue epidermal fibrosis area is reduced by about 85% to about 90%. In some embodiments, the fibrotic tissue epidermal fibrosis area is reduced by about 85% to about 87.5%.

Fibrotic Tissue Epidermal Fibrosis Percent

The present disclosure recognizes the effect of use of adamantane derivatives, preferably memantine on fibrotic tissue epidermal fibrosis percent. In some embodiments, the fibrotic tissue epidermal fibrosis percent is reduced by about 1% to about 90%. In some embodiments, the fibrotic tissue epidermal fibrosis percent is reduced by about 1% to about 85%. In some embodiments, the fibrotic tissue epidermal fibrosis percent is reduced by about 1% to about 80%. In some embodiments, the fibrotic tissue epidermal fibrosis percent is reduced by about 1% to about 75%. In some embodiments, the fibrotic tissue epidermal fibrosis percent is reduced by about 1% to about 70%. In some embodiments, the fibrotic tissue epidermal fibrosis percent is reduced by about 1% to about 65%. In some embodiments, the fibrotic tissue epidermal fibrosis percent is reduced by about 1% to about 60%. In some embodiments, the fibrotic tissue epidermal fibrosis percent is reduced by about 1% to about 55%. In some embodiments, the fibrotic tissue epidermal fibrosis percent is reduced by about 1% to about 50%. In some embodiments, the fibrotic tissue epidermal fibrosis percent is reduced by about 1% to about 45%. In some embodiments, the fibrotic tissue epidermal fibrosis percent is reduced by about 1% to about 40%. In some embodiments, the fibrotic tissue epidermal fibrosis percent is reduced by about 1% to about 35%. In some embodiments, the fibrotic tissue epidermal fibrosis percent is reduced by about 1% to about 30%. In some embodiments, the fibrotic tissue epidermal fibrosis percent is reduced by about 1% to about 25%. In some embodiments, the fibrotic tissue epidermal fibrosis percent is reduced by about 1% to about 20%. In some embodiments, the fibrotic tissue epidermal fibrosis percent is reduced by about 1% to about 15%. In some embodiments, the fibrotic tissue epidermal fibrosis percent is reduced by about 1% to about 10%. In some embodiments, the fibrotic tissue epidermal fibrosis percent is reduced by about 1% to about 5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 5% to about 90%. In some embodiments, the fibrotic tissue epidermal fibrosis percent is reduced by about 5% to about 85%. In some embodiments, the fibrotic tissue epidermal fibrosis percent is reduced by about 5% to about 80%. In some embodiments, the fibrotic tissue epidermal fibrosis percent is reduced by about 5% to about 75%. In some embodiments, the fibrotic tissue epidermal fibrosis percent is reduced by about 5% to about 70%. In some embodiments, the fibrotic tissue epidermal fibrosis percent is reduced by about 5% to about 65%. In some embodiments, the fibrotic tissue epidermal fibrosis percent is reduced by about 5% to about 60%. In some embodiments, the fibrotic tissue epidermal fibrosis percent is reduced by about 5% to about 55%. In some embodiments, the fibrotic tissue epidermal fibrosis percent is reduced by about 5% to about 50%. In some embodiments, the fibrotic tissue epidermal fibrosis percent is reduced by about 5% to about 45%. In some embodiments, the fibrotic tissue epidermal fibrosis percent is reduced by about 5% to about 40%. In some embodiments, the fibrotic tissue epidermal fibrosis percent is reduced by about 5% to about 35%. In some embodiments, the fibrotic tissue epidermal fibrosis percent is reduced by about 5% to about 30%. In some embodiments, the fibrotic tissue epidermal fibrosis percent is reduced by about 5% to about 25%. In some embodiments, the fibrotic tissue epidermal fibrosis percent is reduced by about 5% to about 20%. In some embodiments, the fibrotic tissue epidermal fibrosis percent is reduced by about 5% to about 15%. In some embodiments, the fibrotic tissue epidermal fibrosis percent is reduced by about 5% to about 10%. In some embodiments, the fibrotic tissue epidermal fibrosis percent is reduced by about 5% to about 7.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 10% to about 90%. In some embodiments, the fibrotic tissue epidermal fibrosis percent is reduced by about 10% to about 85%. In some embodiments, the fibrotic tissue epidermal fibrosis percent is reduced by about 10% to about 80%. In some embodiments, the fibrotic tissue epidermal fibrosis percent is reduced by about 10% to about 75%. In some embodiments, the fibrotic tissue epidermal fibrosis percent is reduced by about 10% to about 70%. In some embodiments, the fibrotic tissue epidermal fibrosis percent is reduced by about 10% to about 65%. In some embodiments, the fibrotic tissue epidermal fibrosis percent is reduced by about 10% to about 60%. In some embodiments, the fibrotic tissue epidermal fibrosis percent is reduced by about 10% to about 55%. In some embodiments, the fibrotic tissue epidermal fibrosis percent is reduced by about 10% to about 50%. In some embodiments, the fibrotic tissue epidermal fibrosis percent is reduced by about 10% to about 45%. In some embodiments, the fibrotic tissue epidermal fibrosis percent is reduced by about 10% to about 40%. In some embodiments, the fibrotic tissue epidermal fibrosis percent is reduced by about 10% to about 35%. In some embodiments, the fibrotic tissue epidermal fibrosis percent is reduced by about 10% to about 30%. In some embodiments, the fibrotic tissue epidermal fibrosis percent is reduced by about 10% to about 25%. In some embodiments, the fibrotic tissue epidermal fibrosis percent is reduced by about 10% to about 20%. In some embodiments, the fibrotic tissue epidermal fibrosis percent is reduced by about 10% to about 15%. In some embodiments, the fibrotic tissue epidermal fibrosis percent is reduced by about 10% to about 12.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 15% to about 90%. In some embodiments, the fibrotic tissue epidermal fibrosis percent is reduced by about 15% to about 85%. In some embodiments, the fibrotic tissue epidermal fibrosis percent is reduced by about 15% to about 80%. In some embodiments, the fibrotic tissue epidermal fibrosis percent is reduced by about 15% to about 75%. In some embodiments, the fibrotic tissue epidermal fibrosis percent is reduced by about 15% to about 70%. In some embodiments, the fibrotic tissue epidermal fibrosis percent is reduced by about 15% to about 65%. In some embodiments, the fibrotic tissue epidermal fibrosis percent is reduced by about 15% to about 60%. In some embodiments, the fibrotic tissue epidermal fibrosis percent is reduced by about 15% to about 55%. In some embodiments, the fibrotic tissue epidermal fibrosis percent is reduced by about 15% to about 50%. In some embodiments, the fibrotic tissue epidermal fibrosis percent is reduced by about 15% to about 45%. In some embodiments, the fibrotic tissue epidermal fibrosis percent is reduced by about 15% to about 40%. In some embodiments, the fibrotic tissue epidermal fibrosis percent is reduced by about 15% to about 35%. In some embodiments, the fibrotic tissue epidermal fibrosis percent is reduced by about 15% to about 30%. In some embodiments, the fibrotic tissue epidermal fibrosis percent is reduced by about 15% to about 25%. In some embodiments, the fibrotic tissue epidermal fibrosis percent is reduced by about 15% to about 20%. In some embodiments, the fibrotic tissue epidermal fibrosis percent is reduced by about 15% to about 17.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 20% to about 90%. In some embodiments, the fibrotic tissue epidermal fibrosis percent is reduced by about 20% to about 85%. In some embodiments, the fibrotic tissue epidermal fibrosis percent is reduced by about 20% to about 80%. In some embodiments, the fibrotic tissue epidermal fibrosis percent is reduced by about 20% to about 75%. In some embodiments, the fibrotic tissue epidermal fibrosis percent is reduced by about 20% to about 70%. In some embodiments, the fibrotic tissue epidermal fibrosis percent is reduced by about 20% to about 65%. In some embodiments, the fibrotic tissue epidermal fibrosis percent is reduced by about 20% to about 60%. In some embodiments, the fibrotic tissue epidermal fibrosis percent is reduced by about 20% to about 55%. In some embodiments, the fibrotic tissue epidermal fibrosis percent is reduced by about 20% to about 50%. In some embodiments, the fibrotic tissue epidermal fibrosis percent is reduced by about 20% to about 45%. In some embodiments, the fibrotic tissue epidermal fibrosis percent is reduced by about 20% to about 40%. In some embodiments, the fibrotic tissue epidermal fibrosis percent is reduced by about 20% to about 35%. In some embodiments, the fibrotic tissue epidermal fibrosis percent is reduced by about 20% to about 30%. In some embodiments, the fibrotic tissue epidermal fibrosis percent is reduced by about 20% to about 25%. In some embodiments, the fibrotic tissue epidermal fibrosis percent is reduced by about 20% to about 22.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 25% to about 90%. In some embodiments, the fibrotic tissue epidermal fibrosis percent is reduced by about 25% to about 85%. In some embodiments, the fibrotic tissue epidermal fibrosis percent is reduced by about 25% to about 80%. In some embodiments, the fibrotic tissue epidermal fibrosis percent is reduced by about 25% to about 75%. In some embodiments, the fibrotic tissue epidermal fibrosis percent is reduced by about 25% to about 70%. In some embodiments, the fibrotic tissue epidermal fibrosis percent is reduced by about 25% to about 65%. In some embodiments, the fibrotic tissue epidermal fibrosis percent is reduced by about 25% to about 60%. In some embodiments, the fibrotic tissue epidermal fibrosis percent is reduced by about 25% to about 55%. In some embodiments, the fibrotic tissue epidermal fibrosis percent is reduced by about 25% to about 50%. In some embodiments, the fibrotic tissue epidermal fibrosis percent is reduced by about 25% to about 45%. In some embodiments, the fibrotic tissue epidermal fibrosis percent is reduced by about 25% to about 40%. In some embodiments, the fibrotic tissue epidermal fibrosis percent is reduced by about 25% to about 35%. In some embodiments, the fibrotic tissue epidermal fibrosis percent is reduced by about 25% to about 30%. In some embodiments, the fibrotic tissue epidermal fibrosis percent is reduced by about 25% to about 27.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 30% to about 90%. In some embodiments, the fibrotic tissue epidermal fibrosis percent is reduced by about 30% to about 85%. In some embodiments, the fibrotic tissue epidermal fibrosis percent is reduced by about 30% to about 80%. In some embodiments, the fibrotic tissue epidermal fibrosis percent is reduced by about 30% to about 75%. In some embodiments, the fibrotic tissue epidermal fibrosis percent is reduced by about 30% to about 70%. In some embodiments, the fibrotic tissue epidermal fibrosis percent is reduced by about 30% to about 65%. In some embodiments, the fibrotic tissue epidermal fibrosis percent is reduced by about 30% to about 60%. In some embodiments, the fibrotic tissue epidermal fibrosis percent is reduced by about 30% to about 55%. In some embodiments, the fibrotic tissue epidermal fibrosis percent is reduced by about 30% to about 50%. In some embodiments, the fibrotic tissue epidermal fibrosis percent is reduced by about 30% to about 45%. In some embodiments, the fibrotic tissue epidermal fibrosis percent is reduced by about 30% to about 40%. In some embodiments, the fibrotic tissue epidermal fibrosis percent is reduced by about 30% to about 35%. In some embodiments, the fibrotic tissue epidermal fibrosis percent is reduced by about 30% to about 32.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 35% to about 90%. In some embodiments, the fibrotic tissue epidermal fibrosis percent is reduced by about 35% to about 85%. In some embodiments, the fibrotic tissue epidermal fibrosis percent is reduced by about 35% to about 80%. In some embodiments, the fibrotic tissue epidermal fibrosis percent is reduced by about 35% to about 75%. In some embodiments, the fibrotic tissue epidermal fibrosis percent is reduced by about 35% to about 70%. In some embodiments, the fibrotic tissue epidermal fibrosis percent is reduced by about 35% to about 65%. In some embodiments, the fibrotic tissue epidermal fibrosis percent is reduced by about 35% to about 60%. In some embodiments, the fibrotic tissue epidermal fibrosis percent is reduced by about 35% to about 55%. In some embodiments, the fibrotic tissue epidermal fibrosis percent is reduced by about 35% to about 50%. In some embodiments, the fibrotic tissue epidermal fibrosis percent is reduced by about 35% to about 45%. In some embodiments, the fibrotic tissue epidermal fibrosis percent is reduced by about 35% to about 40%. In some embodiments, the fibrotic tissue epidermal fibrosis percent is reduced by about 35% to about 37.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 40% to about 90%. In some embodiments, the fibrotic tissue epidermal fibrosis percent is reduced by about 40% to about 85%. In some embodiments, the fibrotic tissue epidermal fibrosis percent is reduced by about 40% to about 80%. In some embodiments, the fibrotic tissue epidermal fibrosis percent is reduced by about 40% to about 75%. In some embodiments, the fibrotic tissue epidermal fibrosis percent is reduced by about 40% to about 70%. In some embodiments, the fibrotic tissue epidermal fibrosis percent is reduced by about 40% to about 65%. In some embodiments, the fibrotic tissue epidermal fibrosis percent is reduced by about 40% to about 60%. In some embodiments, the fibrotic tissue epidermal fibrosis percent is reduced by about 40% to about 55%. In some embodiments, the fibrotic tissue epidermal fibrosis percent is reduced by about 40% to about 50%. In some embodiments, the fibrotic tissue epidermal fibrosis percent is reduced by about 40% to about 45%. In some embodiments, the fibrotic tissue epidermal fibrosis percent is reduced by about 40% to about 42.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 45% to about 90%. In some embodiments, the fibrotic tissue epidermal fibrosis percent is reduced by about 45% to about 85%. In some embodiments, the fibrotic tissue epidermal fibrosis percent is reduced by about 45% to about 80%. In some embodiments, the fibrotic tissue epidermal fibrosis percent is reduced by about 45% to about 75%. In some embodiments, the fibrotic tissue epidermal fibrosis percent is reduced by about 45% to about 70%. In some embodiments, the fibrotic tissue epidermal fibrosis percent is reduced by about 45% to about 65%. In some embodiments, the fibrotic tissue epidermal fibrosis percent is reduced by about 45% to about 60%. In some embodiments, the fibrotic tissue epidermal fibrosis percent is reduced by about 45% to about 55%. In some embodiments, the fibrotic tissue epidermal fibrosis percent is reduced by about 45% to about 50%. In some embodiments, the fibrotic tissue epidermal fibrosis percent is reduced by about 45% to about 47.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 50% to about 90%. In some embodiments, the fibrotic tissue epidermal fibrosis percent is reduced by about 50% to about 85%. In some embodiments, the fibrotic tissue epidermal fibrosis percent is reduced by about 50% to about 80%. In some embodiments, the fibrotic tissue epidermal fibrosis percent is reduced by about 50% to about 75%. In some embodiments, the fibrotic tissue epidermal fibrosis percent is reduced by about 50% to about 70%. In some embodiments, the fibrotic tissue epidermal fibrosis percent is reduced by about 50% to about 65%. In some embodiments, the fibrotic tissue epidermal fibrosis percent is reduced by about 50% to about 60%. In some embodiments, the fibrotic tissue epidermal fibrosis percent is reduced by about 50% to about 55%. In some embodiments, the fibrotic tissue epidermal fibrosis percent is reduced by about 50% to about 52.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 55% to about 90%. In some embodiments, the fibrotic tissue epidermal fibrosis percent is reduced by about 55% to about 85%. In some embodiments, the fibrotic tissue epidermal fibrosis percent is reduced by about 55% to about 80%. In some embodiments, the fibrotic tissue epidermal fibrosis percent is reduced by about 55% to about 75%. In some embodiments, the fibrotic tissue epidermal fibrosis percent is reduced by about 55% to about 70%. In some embodiments, the fibrotic tissue epidermal fibrosis percent is reduced by about 55% to about 65%. In some embodiments, the fibrotic tissue epidermal fibrosis percent is reduced by about 55% to about 60%. In some embodiments, the fibrotic tissue epidermal fibrosis percent is reduced by about 55% to about 57.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 60% to about 90%. In some embodiments, the fibrotic tissue epidermal fibrosis percent is reduced by about 60% to about 85%. In some embodiments, the fibrotic tissue epidermal fibrosis percent is reduced by about 60% to about 80%. In some embodiments, the fibrotic tissue epidermal fibrosis percent is reduced by about 60% to about 75%. In some embodiments, the fibrotic tissue epidermal fibrosis percent is reduced by about 60% to about 70%. In some embodiments, the fibrotic tissue epidermal fibrosis percent is reduced by about 60% to about 65%. In some embodiments, the fibrotic tissue epidermal fibrosis percent is reduced by about 60% to about 62.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 65% to about 90%. In some embodiments, the fibrotic tissue epidermal fibrosis percent is reduced by about 65% to about 85%. In some embodiments, the fibrotic tissue epidermal fibrosis percent is reduced by about 65% to about 80%. In some embodiments, the fibrotic tissue epidermal fibrosis percent is reduced by about 65% to about 75%. In some embodiments, the fibrotic tissue epidermal fibrosis percent is reduced by about 65% to about 70%. In some embodiments, the fibrotic tissue epidermal fibrosis percent is reduced by about 65% to about 67.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 70% to about 90%. In some embodiments, the fibrotic tissue epidermal fibrosis percent is reduced by about 70% to about 85%. In some embodiments, the fibrotic tissue epidermal fibrosis percent is reduced by about 70% to about 80%. In some embodiments, the fibrotic tissue epidermal fibrosis percent is reduced by about 70% to about 75%. In some embodiments, the fibrotic tissue epidermal fibrosis percent is reduced by about 70% to about 72.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 75% to about 90%. In some embodiments, the fibrotic tissue epidermal fibrosis percent is reduced by about 75% to about 85%. In some embodiments, the fibrotic tissue epidermal fibrosis percent is reduced by about 75% to about 80%. In some embodiments, the fibrotic tissue epidermal fibrosis percent is reduced by about 75% to about 77.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 80% to about 90%. In some embodiments, the fibrotic tissue epidermal fibrosis percent is reduced by about 80% to about 85%. In some embodiments, the fibrotic tissue epidermal fibrosis percent is reduced by about 80% to about 82.5%.

The present disclosure recognizes the effect of use of adamantane derivatives, preferably memantine on fibrotic tissue epidermal fibrosis percent. In some embodiments, the fibrotic tissue epidermal fibrosis percent is reduced by about 85% to about 90%. In some embodiments, the fibrotic tissue epidermal fibrosis percent is reduced by about 85% to about 87.5%.

Fibrotic Tissue Stiffness or Rigidity

The present disclosure recognizes the effect of use of adamantane derivatives, preferably memantine on fibrotic tissue stiffness or rigidity. In some embodiments, the fibrotic tissue stiffness or rigidity is reduced by about 1% to about 90%. In some embodiments, the fibrotic tissue stiffness or rigidity is reduced by about 1% to about 85%. In some embodiments, the fibrotic tissue stiffness or rigidity is reduced by about 1% to about 80%. In some embodiments, the fibrotic tissue stiffness or rigidity is reduced by about 1% to about 75%. In some embodiments, the fibrotic tissue stiffness or rigidity is reduced by about 1% to about 70%. In some embodiments, the fibrotic tissue stiffness or rigidity is reduced by about 1% to about 65%. In some embodiments, the fibrotic tissue stiffness or rigidity is reduced by about 1% to about 60%. In some embodiments, the fibrotic tissue stiffness or rigidity is reduced by about 1% to about 55%. In some embodiments, the fibrotic tissue stiffness or rigidity is reduced by about 1% to about 50%. In some embodiments, the fibrotic tissue stiffness or rigidity is reduced by about 1% to about 45%. In some embodiments, the fibrotic tissue stiffness or rigidity is reduced by about 1% to about 40%. In some embodiments, the fibrotic tissue stiffness or rigidity is reduced by about 1% to about 35%. In some embodiments, the fibrotic tissue stiffness or rigidity is reduced by about 1% to about 30%. In some embodiments, the fibrotic tissue stiffness or rigidity is reduced by about 1% to about 25%. In some embodiments, the fibrotic tissue stiffness or rigidity is reduced by about 1% to about 20%. In some embodiments, the fibrotic tissue stiffness or rigidity is reduced by about 1% to about 15%. In some embodiments, the fibrotic tissue stiffness or rigidity is reduced by about 1% to about 10%. In some embodiments, the fibrotic tissue stiffness or rigidity is reduced by about 1% to about 5%.

The present disclosure recognizes the effect of use of adamantane derivatives, preferably memantine on fibrotic tissue stiffness or rigidity. In some embodiments, the fibrotic tissue stiffness or rigidity is reduced by about 5% to about 90%. In some embodiments, the fibrotic tissue stiffness or rigidity is reduced by about 5% to about 85%. In some embodiments, the fibrotic tissue stiffness or rigidity is reduced by about 5% to about 80%. In some embodiments, the fibrotic tissue stiffness or rigidity is reduced by about 5% to about 75%. In some embodiments, the fibrotic tissue stiffness or rigidity is reduced by about 5% to about 70%. In some embodiments, the fibrotic tissue stiffness or rigidity is reduced by about 5% to about 65%. In some embodiments, the fibrotic tissue stiffness or rigidity is reduced by about 5% to about 60%. In some embodiments, the fibrotic tissue stiffness or rigidity is reduced by about 5% to about 55%. In some embodiments, the fibrotic tissue stiffness or rigidity is reduced by about 5% to about 50%. In some embodiments, the fibrotic tissue stiffness or rigidity is reduced by about 5% to about 45%. In some embodiments, the fibrotic tissue stiffness or rigidity is reduced by about 5% to about 40%. In some embodiments, the fibrotic tissue stiffness or rigidity is reduced by about 5% to about 35%. In some embodiments, the fibrotic tissue stiffness or rigidity is reduced by about 5% to about 30%. In some embodiments, the fibrotic tissue stiffness or rigidity is reduced by about 5% to about 25%. In some embodiments, the fibrotic tissue stiffness or rigidity is reduced by about 5% to about 20%. In some embodiments, the fibrotic tissue stiffness or rigidity is reduced by about 5% to about 15%. In some embodiments, the fibrotic tissue stiffness or rigidity is reduced by about 5% to about 10%. In some embodiments, the fibrotic tissue stiffness or rigidity is reduced by about 5% to about 7.5%.

The present disclosure recognizes the effect of use of adamantane derivatives, preferably memantine on fibrotic tissue stiffness or rigidity. In some embodiments, the fibrotic tissue stiffness or rigidity is reduced by about 10% to about 90%. In some embodiments, the fibrotic tissue stiffness or rigidity is reduced by about 10% to about 85%. In some embodiments, the fibrotic tissue stiffness or rigidity is reduced by about 10% to about 80%. In some embodiments, the fibrotic tissue stiffness or rigidity is reduced by about 10% to about 75%. In some embodiments, the fibrotic tissue stiffness or rigidity is reduced by about 10% to about 70%. In some embodiments, the fibrotic tissue stiffness or rigidity is reduced by about 10% to about 65%. In some embodiments, the fibrotic tissue stiffness or rigidity is reduced by about 10% to about 60%. In some embodiments, the fibrotic tissue stiffness or rigidity is reduced by about 10% to about 55%. In some embodiments, the fibrotic tissue stiffness or rigidity is reduced by about 10% to about 50%. In some embodiments, the fibrotic tissue stiffness or rigidity is reduced by about 10% to about 45%. In some embodiments, the fibrotic tissue stiffness or rigidity is reduced by about 10% to about 40%. In some embodiments, the fibrotic tissue stiffness or rigidity is reduced by about 10% to about 35%. In some embodiments, the fibrotic tissue stiffness or rigidity is reduced by about 10% to about 30%. In some embodiments, the fibrotic tissue stiffness or rigidity is reduced by about 10% to about 25%. In some embodiments, the fibrotic tissue stiffness or rigidity is reduced by about 10% to about 20%. In some embodiments, the fibrotic tissue stiffness or rigidity is reduced by about 10% to about 15%. In some embodiments, the fibrotic tissue stiffness or rigidity is reduced by about 10% to about 12.5%.

The present disclosure recognizes the effect of use of adamantane derivatives, preferably memantine on fibrotic tissue stiffness or rigidity. In some embodiments, the fibrotic tissue stiffness or rigidity is reduced by about 15% to about 90%. In some embodiments, the fibrotic tissue stiffness or rigidity is reduced by about 15% to about 85%. In some embodiments, the fibrotic tissue stiffness or rigidity is reduced by about 15% to about 80%. In some embodiments, the fibrotic tissue stiffness or rigidity is reduced by about 15% to about 75%. In some embodiments, the fibrotic tissue stiffness or rigidity is reduced by about 15% to about 70%. In some embodiments, the fibrotic tissue stiffness or rigidity is reduced by about 15% to about 65%. In some embodiments, the fibrotic tissue stiffness or rigidity is reduced by about 15% to about 60%. In some embodiments, the fibrotic tissue stiffness or rigidity is reduced by about 15% to about 55%. In some embodiments, the fibrotic tissue stiffness or rigidity is reduced by about 15% to about 50%. In some embodiments, the fibrotic tissue stiffness or rigidity is reduced by about 15% to about 45%. In some embodiments, the fibrotic tissue stiffness or rigidity is reduced by about 15% to about 40%. In some embodiments, the fibrotic tissue stiffness or rigidity is reduced by about 15% to about 35%. In some embodiments, the fibrotic tissue stiffness or rigidity is reduced by about 15% to about 30%. In some embodiments, the fibrotic tissue stiffness or rigidity is reduced by about 15% to about 25%. In some embodiments, the fibrotic tissue stiffness or rigidity is reduced by about 15% to about 20%. In some embodiments, the fibrotic tissue stiffness or rigidity is reduced by about 15% to about 17.5%.

The present disclosure recognizes the effect of use of adamantane derivatives, preferably memantine on fibrotic tissue stiffness or rigidity. In some embodiments, the fibrotic tissue stiffness or rigidity is reduced by about 20% to about 90%. In some embodiments, the fibrotic tissue stiffness or rigidity is reduced by about 20% to about 85%. In some embodiments, the fibrotic tissue stiffness or rigidity is reduced by about 20% to about 80%. In some embodiments, the fibrotic tissue stiffness or rigidity is reduced by about 20% to about 75%. In some embodiments, the fibrotic tissue stiffness or rigidity is reduced by about 20% to about 70%. In some embodiments, the fibrotic tissue stiffness or rigidity is reduced by about 20% to about 65%. In some embodiments, the fibrotic tissue stiffness or rigidity is reduced by about 20% to about 60%. In some embodiments, the fibrotic tissue stiffness or rigidity is reduced by about 20% to about 55%. In some embodiments, the fibrotic tissue stiffness or rigidity is reduced by about 20% to about 50%. In some embodiments, the fibrotic tissue stiffness or rigidity is reduced by about 20% to about 45%. In some embodiments, the fibrotic tissue stiffness or rigidity is reduced by about 20% to about 40%. In some embodiments, the fibrotic tissue stiffness or rigidity is reduced by about 20% to about 35%. In some embodiments, the fibrotic tissue stiffness or rigidity is reduced by about 20% to about 30%. In some embodiments, the fibrotic tissue stiffness or rigidity is reduced by about 20% to about 25%. In some embodiments, the fibrotic tissue stiffness or rigidity is reduced by about 20% to about 22.5%.

The present disclosure recognizes the effect of use of adamantane derivatives, preferably memantine on fibrotic tissue stiffness or rigidity. In some embodiments, the fibrotic tissue stiffness or rigidity is reduced by about 25% to about 90%. In some embodiments, the fibrotic tissue stiffness or rigidity is reduced by about 25% to about 85%. In some embodiments, the fibrotic tissue stiffness or rigidity is reduced by about 25% to about 80%. In some embodiments, the fibrotic tissue stiffness or rigidity is reduced by about 25% to about 75%. In some embodiments, the fibrotic tissue stiffness or rigidity is reduced by about 25% to about 70%. In some embodiments, the fibrotic tissue stiffness or rigidity is reduced by about 25% to about 65%. In some embodiments, the fibrotic tissue stiffness or rigidity is reduced by about 25% to about 60%. In some embodiments, the fibrotic tissue stiffness or rigidity is reduced by about 25% to about 55%. In some embodiments, the fibrotic tissue stiffness or rigidity is reduced by about 25% to about 50%. In some embodiments, the fibrotic tissue stiffness or rigidity is reduced by about 25% to about 45%. In some embodiments, the fibrotic tissue stiffness or rigidity is reduced by about 25% to about 40%. In some embodiments, the fibrotic tissue stiffness or rigidity is reduced by about 25% to about 35%. In some embodiments, the fibrotic tissue stiffness or rigidity is reduced by about 25% to about 30%. In some embodiments, the fibrotic tissue stiffness or rigidity is reduced by about 25% to about 27.5%.

The present disclosure recognizes the effect of use of adamantane derivatives, preferably memantine on fibrotic tissue stiffness or rigidity In some embodiments, the fibrotic tissue stiffness or rigidity is reduced by about 30% to about 90%. In some embodiments, the fibrotic tissue stiffness or rigidity is reduced by about 30% to about 85%. In some embodiments, the fibrotic tissue stiffness or rigidity is reduced by about 30% to about 80%. In some embodiments, the fibrotic tissue stiffness or rigidity is reduced by about 30% to about 75%. In some embodiments, the fibrotic tissue stiffness or rigidity is reduced by about 30% to about 70%. In some embodiments, the fibrotic tissue stiffness or rigidity is reduced by about 30% to about 65%. In some embodiments, the fibrotic tissue stiffness or rigidity is reduced by about 30% to about 60%. In some embodiments, the fibrotic tissue stiffness or rigidity is reduced by about 30% to about 55%. In some embodiments, the fibrotic tissue stiffness or rigidity is reduced by about 30% to about 50%. In some embodiments, the fibrotic tissue stiffness or rigidity is reduced by about 30% to about 45%. In some embodiments, the fibrotic tissue stiffness or rigidity is reduced by about 30% to about 40%. In some embodiments, the fibrotic tissue stiffness or rigidity is reduced by about 30% to about 35%. In some embodiments, the fibrotic tissue stiffness or rigidity is reduced by about 30% to about 32.5%.

The present disclosure recognizes the effect of use of adamantane derivatives, preferably memantine on fibrotic tissue stiffness or rigidity In some embodiments, the fibrotic tissue stiffness or rigidity is reduced by about 35% to about 90%. In some embodiments, the fibrotic tissue stiffness or rigidity is reduced by about 35% to about 85%. In some embodiments, the fibrotic tissue stiffness or rigidity is reduced by about 35% to about 80%. In some embodiments, the fibrotic tissue stiffness or rigidity is reduced by about 35% to about 75%. In some embodiments, the fibrotic tissue stiffness or rigidity is reduced by about 35% to about 70%. In some embodiments, the fibrotic tissue stiffness or rigidity is reduced by about 35% to about 65%. In some embodiments, the fibrotic tissue stiffness or rigidity is reduced by about 35% to about 60%. In some embodiments, the fibrotic tissue stiffness or rigidity is reduced by about 35% to about 55%. In some embodiments, the fibrotic tissue stiffness or rigidity is reduced by about 35% to about 50%. In some embodiments, the fibrotic tissue stiffness or rigidity is reduced by about 35% to about 45%. In some embodiments, the fibrotic tissue stiffness or rigidity is reduced by about 35% to about 40%. In some embodiments, the fibrotic tissue stiffness or rigidity is reduced by about 35% to about 37.5%.

The present disclosure recognizes the effect of use of adamantane derivatives, preferably memantine on fibrotic tissue stiffness or rigidity. In some embodiments, the fibrotic tissue stiffness or rigidity is reduced by about 40% to about 90%. In some embodiments, the fibrotic tissue stiffness or rigidity is reduced by about 40% to about 85%. In some embodiments, the fibrotic tissue stiffness or rigidity is reduced by about 40% to about 80%. In some embodiments, the fibrotic tissue stiffness or rigidity is reduced by about 40% to about 75%. In some embodiments, the fibrotic tissue stiffness or rigidity is reduced by about 40% to about 70%. In some embodiments, the fibrotic tissue stiffness or rigidity is reduced by about 40% to about 65%. In some embodiments, the fibrotic tissue stiffness or rigidity is reduced by about 40% to about 60%. In some embodiments, the fibrotic tissue stiffness or rigidity is reduced by about 40% to about 55%. In some embodiments, the fibrotic tissue stiffness or rigidity is reduced by about 40% to about 50%. In some embodiments, the fibrotic tissue stiffness or rigidity is reduced by about 40% to about 45%. In some embodiments, the fibrotic tissue stiffness or rigidity is reduced by about 40% to about 42.5%.

The present disclosure recognizes the effect of use of adamantane derivatives, preferably memantine on fibrotic tissue stiffness or rigidity. In some embodiments, the fibrotic tissue stiffness or rigidity is reduced by about 45% to about 90%. In some embodiments, the fibrotic tissue stiffness or rigidity is reduced by about 45% to about 85%. In some embodiments, the fibrotic tissue stiffness or rigidity is reduced by about 45% to about 80%. In some embodiments, the fibrotic tissue stiffness or rigidity is reduced by about 45% to about 75%. In some embodiments, the fibrotic tissue stiffness or rigidity is reduced by about 45% to about 70%. In some embodiments, the fibrotic tissue stiffness or rigidity is reduced by about 45% to about 65%. In some embodiments, the fibrotic tissue stiffness or rigidity is reduced by about 45% to about 60%. In some embodiments, the fibrotic tissue stiffness or rigidity is reduced by about 45% to about 55%. In some embodiments, the fibrotic tissue stiffness or rigidity is reduced by about 45% to about 50%. In some embodiments, the fibrotic tissue stiffness or rigidity is reduced by about 45% to about 47.5%.

The present disclosure recognizes the effect of use of adamantane derivatives, preferably memantine on fibrotic tissue stiffness or rigidity In some embodiments, the fibrotic tissue stiffness or rigidity is reduced by about 50% to about 90%. In some embodiments, the fibrotic tissue stiffness or rigidity is reduced by about 50% to about 85%. In some embodiments, the fibrotic tissue stiffness or rigidity is reduced by about 50% to about 80%. In some embodiments, the fibrotic tissue stiffness or rigidity is reduced by about 50% to about 75%. In some embodiments, the fibrotic tissue stiffness or rigidity is reduced by about 50% to about 70%. In some embodiments, the fibrotic tissue stiffness or rigidity is reduced by about 50% to about 65%. In some embodiments, the fibrotic tissue stiffness or rigidity is reduced by about 50% to about 60%. In some embodiments, the fibrotic tissue stiffness or rigidity is reduced by about 50% to about 55%. In some embodiments, the fibrotic tissue stiffness or rigidity is reduced by about 50% to about 52.5%.

The present disclosure recognizes the effect of use of adamantane derivatives, preferably memantine on fibrotic tissue stiffness or rigidity. In some embodiments, the fibrotic tissue stiffness or rigidity is reduced by about 55% to about 90%. In some embodiments, the fibrotic tissue stiffness or rigidity is reduced by about 55% to about 85%. In some embodiments, the fibrotic tissue stiffness or rigidity is reduced by about 55% to about 80%. In some embodiments, the fibrotic tissue stiffness or rigidity is reduced by about 55% to about 75%. In some embodiments, the fibrotic tissue stiffness or rigidity is reduced by about 55% to about 70%. In some embodiments, the fibrotic tissue stiffness or rigidity is reduced by about 55% to about 65%. In some embodiments, the fibrotic tissue stiffness or rigidity is reduced by about 55% to about 60%. In some embodiments, the fibrotic tissue stiffness or rigidity is reduced by about 55% to about 57.5%.

The present disclosure recognizes the effect of use of adamantane derivatives, preferably memantine on fibrotic tissue stiffness or rigidity. In some embodiments, the fibrotic tissue stiffness or rigidity is reduced by about 60% to about 90%. In some embodiments, the fibrotic tissue stiffness or rigidity is reduced by about 60% to about 85%. In some embodiments, the fibrotic tissue stiffness or rigidity is reduced by about 60% to about 80%. In some embodiments, the fibrotic tissue stiffness or rigidity is reduced by about 60% to about 75%. In some embodiments, the fibrotic tissue stiffness or rigidity is reduced by about 60% to about 70%. In some embodiments, the fibrotic tissue stiffness or rigidity is reduced by about 60% to about 65%. In some embodiments, the fibrotic tissue stiffness or rigidity is reduced by about 60% to about 62.5%.

The present disclosure recognizes the effect of use of adamantane derivatives, preferably memantine on fibrotic tissue stiffness or rigidity. In some embodiments, the fibrotic tissue stiffness or rigidity is reduced by about 65% to about 90%. In some embodiments, the fibrotic tissue stiffness or rigidity is reduced by about 65% to about 85%. In some embodiments, the fibrotic tissue stiffness or rigidity is reduced by about 65% to about 80%. In some embodiments, the fibrotic tissue stiffness or rigidity is reduced by about 65% to about 75%. In some embodiments, the fibrotic tissue stiffness or rigidity is reduced by about 65% to about 70%. In some embodiments, the fibrotic tissue stiffness or rigidity is reduced by about 65% to about 67.5%.

The present disclosure recognizes the effect of use of adamantane derivatives, preferably memantine on fibrotic tissue stiffness or rigidity. In some embodiments, the fibrotic tissue stiffness or rigidity is reduced by about 70% to about 90%. In some embodiments, the fibrotic tissue stiffness or rigidity is reduced by about 70% to about 85%. In some embodiments, the fibrotic tissue stiffness or rigidity is reduced by about 70% to about 80%. In some embodiments, the fibrotic tissue stiffness or rigidity is reduced by about 70% to about 75%. In some embodiments, the fibrotic tissue stiffness or rigidity is reduced by about 70% to about 72.5%.

The present disclosure recognizes the effect of use of adamantane derivatives, preferably memantine on fibrotic tissue stiffness or rigidity. In some embodiments, the fibrotic tissue stiffness or rigidity is reduced by about 75% to about 90%. In some embodiments, the fibrotic tissue stiffness or rigidity is reduced by about 75% to about 85%. In some embodiments, the fibrotic tissue stiffness or rigidity is reduced by about 75% to about 80%. In some embodiments, the fibrotic tissue stiffness or rigidity is reduced by about 75% to about 77.5%.

The present disclosure recognizes the effect of use of adamantane derivatives, preferably memantine on fibrotic tissue stiffness or rigidity. In some embodiments, the fibrotic tissue stiffness or rigidity is reduced by about 80% to about 90%. In some embodiments, the fibrotic tissue stiffness or rigidity is reduced by about 80% to about 85%. In some embodiments, the fibrotic tissue stiffness or rigidity is reduced by about 80% to about 82.5%.

The present disclosure recognizes the effect of use of adamantane derivatives, preferably memantine on fibrotic tissue stiffness or rigidity. In some embodiments, the fibrotic tissue stiffness or rigidity is reduced by about 85% to about 90%. In some embodiments, the fibrotic tissue stiffness or rigidity is reduced by about 85% to about 87.5%.

The present disclosure provides methods for treating a patient diagnosed as suffering from a fibromatosis disorder such as an integumentary system fibromatosis condition described herein above (e.g., palmar fibromatosis (Dupuytren's disease), plantar fibromatosis (Ledderhose disease), adhesive capsulitis (frozen shoulder), surgical adhesions, scleroderma, keloids, hypertrophic scarring, diabetic fibrosis (diabetic hand), nephrogenic systemic fibrosis, and penile fibromatosis (Peyronie's disease). As discussed herein throughout those of skill in the art of fibromatosis are aware of a variety of methods for reducing fibrotic tissues, and any conventional fibrotic tissue reduction methods can be used in conjunction with the invention. The treatment method of the invention entails administering to a patient having a fibromatosis disorder a pharmaceutical composition containing a therapeutically effective amount of an adamantane derivative, preferably memantine either alone or in combination with another therapeutic intervention.

Non-Limiting Embodiments

The present disclosure is also described and demonstrated by way of the following non-limiting embodiments. However, the use of these and other embodiments anywhere in the specification is illustrative only and in no way limits the scope and meaning of the disclosure or of any exemplified term. Likewise, the disclosure is not limited to any particular preferred embodiment or aspect described herein. Indeed, suitable modifications and variations may be apparent to those skilled in the art upon reading this specification, and such variations can be made without departing from the disclosure in spirit or in scope.

1. A pharmaceutical composition for treating a fibromatosis condition, the composition comprising a therapeutically effective amount of an adamantane derivative, preferably memantine or a pharmaceutically acceptable salt thereof and a pharmaceutically acceptable carrier.

2. The composition of embodiment 1, wherein the fibromatosis condition is an integumentary system fibromatosis condition.

3. The composition of embodiment 1, wherein the fibromatosis condition is palmar fibromatosis (Dupuytren's disease), plantar fibromatosis (Ledderhose disease), adhesive capsulitis (frozen shoulder), surgical adhesions, scleroderma, keloids, hypertrophic scarring, diabetic fibrosis (diabetic hand), nephrogenic systemic fibrosis or penile fibromatosis (Peyronie's disease).

4. The composition of embodiment 1, wherein the fibromatosis condition is palmar fibromatosis (Dupuytren's disease), plantar fibromatosis (Ledderhose disease), or diabetic fibrosis (diabetic hand).

5. The composition of embodiment 1, wherein the fibromatosis condition is palmar fibromatosis (Dupuytren's disease), plantar fibromatosis (Ledderhose disease), or scleroderma.

6. The composition of embodiment 1, wherein said fibromatosis condition is palmar fibromatosis (Dupuytren's disease).

7. The composition of embodiment 1, wherein said fibromatosis condition is plantar fibromatosis (Ledderhose disease).

8. The composition of embodiment 1, wherein said fibromatosis condition is adhesive capsulitis (frozen shoulder).

9. The composition of embodiment 1, wherein said fibromatosis condition is surgical adhesions.

10. The composition of embodiment 1, wherein said fibromatosis condition is scleroderma.

11. The composition of embodiment 1, wherein said fibromatosis condition is keloids.

12. The composition of embodiment 1, wherein said fibromatosis condition is hypertrophic scarring.

13. The composition of embodiment 1, wherein said fibromatosis condition is diabetic fibrosis (diabetic hand).

14. The composition of embodiment 1, wherein said fibromatosis condition is nephrogenic systemic fibrosis.

15. The composition of embodiment 1, wherein said fibromatosis condition is penile fibromatosis (Peyronie's disease).

16. The composition of embodiments 2-15, wherein fibrotic tissue volume is reduced by about 1% to about 30%.

17. The composition of embodiments 2-15, wherein fibrotic tissue volume is reduced by about 3% to about 30%.

18. The composition of embodiments 2-15, wherein fibrotic tissue volume is reduced by about 5% to about 30%.

19. The composition of embodiments 2-15, wherein fibrotic tissue volume is reduced by about 10% to about 30%.

20. The composition of embodiments 2-15, wherein fibrotic tissue volume is reduced by about 15% to about 30%.

21. The composition of embodiments 2-15, wherein fibrotic tissue volume is reduced by about 20% to about 30%.

22. The composition of embodiments 2-15, wherein fibrotic tissue volume is reduced by about 1% to about 60%.

23. The composition of embodiments 2-15, wherein fibrotic tissue volume is reduced by about 3% to about 60%.

24. The composition of embodiments 2-15, wherein fibrotic tissue volume is reduced by about 5% to about 60%.

25. The composition of embodiments 2-15, wherein fibrotic tissue volume is reduced by about 10% to about 60%.

26. The composition of embodiments 2-15, wherein fibrotic tissue volume is reduced by about 15% to about 60%.

27. The composition of embodiments 2-15, wherein fibrotic tissue volume is reduced by about 20% to about 60%.

28. The composition of embodiments 2-15, wherein fibrotic tissue volume is reduced by about 1% to about 45%.

29. The composition of embodiments 2-15, wherein fibrotic tissue volume is reduced by about 3% to about 45%.

30. The composition of embodiments 2-15, wherein fibrotic tissue volume is reduced by about 5% to about 45%.

31. The composition of embodiments 2-15, wherein fibrotic tissue volume is reduced by about 10% to about 45%.

32. The composition of embodiments 2-15, wherein fibrotic tissue volume is reduced by about 15% to about 45%.

33. The composition of embodiments 2-15, wherein fibrotic tissue volume is reduced by about 20% to about 45%.

34. The composition of embodiments 2-33, wherein fibrotic tissue dermal fibrosis area is reduced by about 1% to about 50%.

35. The composition of embodiments 2-33, wherein fibrotic tissue dermal fibrosis area is reduced by about 3% to about 50%.

36. The composition of embodiments 2-33, wherein fibrotic tissue dermal fibrosis area is reduced by about 5% to about 50%.

37. The composition of embodiments 2-33, wherein fibrotic tissue dermal fibrosis area is reduced by about 10% to about 50%.

38. The composition of embodiments 2-33, wherein fibrotic tissue dermal fibrosis area is reduced by about 15% to about 50%.

39. The composition of embodiments 2-33, wherein fibrotic tissue dermal fibrosis area is reduced by about 20% to about 50%.

40. The composition of embodiments 2-33, wherein fibrotic tissue dermal fibrosis area is reduced by about 1% to about 30%.

41. The composition of embodiments 2-33, wherein fibrotic tissue dermal fibrosis area is reduced by about 3% to about 30%.

42. The composition of embodiments 2-33, wherein fibrotic tissue dermal fibrosis area is reduced by about 5% to about 30%.

43. The composition of embodiments 2-33, wherein fibrotic tissue dermal fibrosis area is reduced by about 10% to about 30%.

44. The composition of embodiments 2-43, wherein fibrotic tissue dermal fibrosis percent is reduced by about 1% to about 70%.

45. The composition of embodiments 2-43, wherein fibrotic tissue dermal fibrosis percent is reduced by about 3% to about 70%.

46. The composition of embodiments 2-43, wherein fibrotic tissue dermal fibrosis percent is reduced by about 5% to about 70%.

47. The composition of embodiments 2-43, wherein fibrotic tissue dermal fibrosis percent is reduced by about 10% to about 70%.

48. The composition of embodiments 2-43, wherein fibrotic tissue dermal fibrosis percent is reduced by about 15% to about 70%.

49. The composition of embodiments 2-43, wherein fibrotic tissue dermal fibrosis percent is reduced by about 20% to about 70%.

50. The composition of embodiments 2-43, wherein fibrotic tissue dermal fibrosis percent is reduced by about 1% to about 35%.

51. The composition of embodiments 2-43, wherein fibrotic tissue dermal fibrosis percent is reduced by about 3% to about 35%.

52. The composition of embodiments 2-43, wherein fibrotic tissue dermal fibrosis percent is reduced by about 5% to about 35%.

53. The composition of embodiments 2-43, wherein fibrotic tissue dermal fibrosis percent is reduced by about 10% to about 35%.
54. The composition of embodiments 2-43, wherein fibrotic tissue dermal fibrosis percent is reduced by about 15% to about 35%.
55. The composition of embodiments 2-43, wherein fibrotic tissue dermal fibrosis percent is reduced by about 20% to about 35%.
56. The composition of embodiments 2-43, wherein fibrotic tissue dermal fibrosis percent is reduced by about 25% to about 35%.
57. The composition of embodiments 2-56, wherein fibrotic tissue epidermal fibrosis area is reduced by about 1% to about 75%.
58. The composition of embodiments 2-56, wherein fibrotic tissue epidermal fibrosis area is reduced by about 3% to about 75%.
59. The composition of embodiments 2-56, wherein fibrotic tissue epidermal fibrosis area is reduced by about 5% to about 75%.
60. The composition of embodiments 2-56, wherein fibrotic tissue epidermal fibrosis area is reduced by about 10% to about 75%.
61. The composition of embodiments 2-56, wherein fibrotic tissue epidermal fibrosis area is reduced by about 15% to about 75%.
62. The composition of embodiments 2-56, wherein fibrotic tissue epidermal fibrosis area is reduced by about 20% to about 75%.
63. The composition of embodiments 2-56, wherein fibrotic tissue epidermal fibrosis area is reduced by about 25% to about 75%.
64. The composition of embodiments 2-56, wherein fibrotic tissue epidermal fibrosis area is reduced by about 1% to about 50%.
65. The composition of embodiments 2-56, wherein fibrotic tissue epidermal fibrosis area is reduced by about 3% to about 50%.
66. The composition of embodiments 2-56, wherein fibrotic tissue epidermal fibrosis area is reduced by about 5% to about 50%.
67. The composition of embodiments 2-56, wherein fibrotic tissue epidermal fibrosis area is reduced by about 10% to about 50%.
68. The composition of embodiments 2-56, wherein fibrotic tissue epidermal fibrosis area is reduced by about 15% to about 50%.
69. The composition of embodiments 2-56, wherein fibrotic tissue epidermal fibrosis area is reduced by about 20% to about 50%.
70. The composition of embodiments 2-56, wherein fibrotic tissue epidermal fibrosis area is reduced by about 25% to about 50%.
71. The composition of embodiments 2-56, wherein fibrotic tissue epidermal fibrosis area is reduced by about 30% to about 50%.
72. The composition of embodiments 2-71, wherein fibrotic tissue epidermal fibrosis percent is reduced by about 1% to about 75%.
73. The composition of embodiments 2-71, wherein fibrotic tissue epidermal fibrosis percent is reduced by about 3% to about 75%.
74. The composition of embodiments 2-71, wherein fibrotic tissue epidermal fibrosis percent is reduced by about 5% to about 75%.
75. The composition of embodiments 2-71, wherein fibrotic tissue epidermal fibrosis percent is reduced by about 10% to about 75%.
76. The composition of embodiments 2-71, wherein fibrotic tissue epidermal fibrosis percent is reduced by about 15% to about 75%.
77. The composition of embodiments 2-71, wherein fibrotic tissue epidermal fibrosis percent is reduced by about 20% to about 75%.
78. The composition of embodiments 2-71, wherein fibrotic tissue epidermal fibrosis percent is reduced by about 25% to about 75%.
79. The composition of embodiments 2-71, wherein fibrotic tissue epidermal fibrosis percent is reduced by about 1% to about 50%.
80. The composition of embodiments 2-71, wherein fibrotic tissue epidermal fibrosis percent is reduced by about 3% to about 50%.
81. The composition of embodiments 2-71, wherein fibrotic tissue epidermal fibrosis percent is reduced by about 5% to about 50%.
82. The composition of embodiments 2-71, wherein fibrotic tissue epidermal fibrosis percent is reduced by about 10% to about 50%.
83. The composition of embodiments 2-71, wherein fibrotic tissue epidermal fibrosis percent is reduced by about 15% to about 50%.
84. The composition of embodiments 2-71, wherein fibrotic tissue epidermal fibrosis percent is reduced by about 20% to about 50%.
85. The composition of embodiments 2-71, wherein fibrotic tissue epidermal fibrosis percent is reduced by about 25% to about 50%.
86. The composition of embodiments 2-71, wherein fibrotic tissue epidermal fibrosis percent is reduced by about 30% to about 50%.
87. The composition of embodiments 2-86, wherein fibrotic tissue stiffness or rigidity is reduced by about 1% to about 75%.
88. The composition of embodiments 2-86, wherein fibrotic tissue stiffness or rigidity is reduced by about 3% to about 75%.
89. The composition of embodiments 2-86, wherein fibrotic tissue stiffness or rigidity is reduced by about 5% to about 75%.
90. The composition of embodiments 2-86, wherein fibrotic tissue stiffness or rigidity is reduced by about 10% to about 75%.
91. The composition of embodiments 2-86, wherein fibrotic tissue stiffness or rigidity is reduced by about 15% to about 75%.
92. The composition of embodiments 2-86, wherein fibrotic tissue stiffness or rigidity is reduced by about 20% to about 75%.
93. The composition of embodiments 2-86, wherein fibrotic tissue stiffness or rigidity is reduced by about 25% to about 75%.
94. The composition of embodiments 2-86, wherein fibrotic tissue stiffness or rigidity is reduced by about 1% to about 45%.
95. The composition of embodiments 2-86, wherein fibrotic tissue stiffness or rigidity is reduced by about 3% to about 45%.
96. The composition of embodiments 2-86, wherein fibrotic tissue stiffness or rigidity is reduced by about 5% to about 45%.

97. The composition of embodiments 2-86, wherein fibrotic tissue stiffness or rigidity is reduced by about 10% to about 45%.
98. The composition of embodiments 2-86, wherein fibrotic tissue stiffness or rigidity is reduced by about 15% to about 45%.
99. The composition of embodiments 2-86, wherein fibrotic tissue stiffness or rigidity is reduced by about 20% to about 45%.
100. The composition of embodiments 2-86, wherein fibrotic tissue stiffness or rigidity is reduced by about 25% to about 45%.
101. The composition of embodiments 2-86, wherein fibrotic tissue stiffness or rigidity is reduced by about 30% to about 45%.
102. The composition of embodiment 2, wherein the composition comprises an injectable composition.
103. The composition of embodiment 2, wherein the pharmaceutically acceptable salt is hydrochloride.
104. A method of reducing fibromatosis in a subject in need thereof, the method comprising contacting the fibrotic tissue with a composition comprising a therapeutically effective amount of an adamantane derivative, preferably memantine or a pharmaceutically acceptable salt thereof and a pharmaceutically acceptable carrier.
105. The method of embodiment 104, wherein said subject is a mammal.
106. The method of embodiment 104, wherein said mammal is a human.
107. The method of embodiment 104, wherein the fibromatosis condition is associated with a fibromatosis condition selected from the group consisting of palmar fibromatosis (Dupuytren's disease), plantar fibromatosis (Ledderhose disease), adhesive capsulitis (frozen shoulder), surgical adhesions, scleroderma, keloids, hypertrophic scarring, diabetic fibrosis (diabetic hand), nephrogenic systemic fibrosis or penile fibromatosis (Peyronie's disease).
108. The method of embodiment 104, wherein said fibromatosis condition is palmar fibromatosis (Dupuytren's disease).
109. The method of embodiment 104, wherein said fibromatosis condition is plantar fibromatosis (Ledderhose disease).
110. The method of embodiment 104, wherein said fibromatosis condition is adhesive capsulitis (frozen shoulder).
111. The method of embodiment 104, wherein said fibromatosis condition is surgical adhesions.
112. The method of embodiment 104, wherein said fibromatosis condition is scleroderma.
113. The method of embodiment 104, wherein said fibromatosis condition is keloids.
114. The method of embodiment 104, wherein said fibromatosis condition is hypertrophic scarring.
115. The method of embodiment 104, wherein said fibromatosis condition is diabetic fibrosis (diabetic hand).
116. The method of embodiment 104, wherein said fibromatosis condition is nephrogenic systemic fibrosis.
117. The method of embodiment 104, wherein said fibromatosis condition is penile fibromatosis (Peyronie's disease).
118. The method of embodiments 104-117, wherein fibrotic tissue volume is reduced by about 1% to about 30%.
119. The method of embodiments 104-117, wherein fibrotic tissue volume is reduced by about 3% to about 30%.
120. The method of embodiments 104-117, wherein fibrotic tissue volume is reduced by about 5% to about 30%.
121. The method of embodiments 104-117, wherein fibrotic tissue volume is reduced by about 10% to about 30%.
122. The method of embodiments 104-117, wherein fibrotic tissue volume is reduced by about 15% to about 30%.
123. The method of embodiments 104-117, wherein fibrotic tissue volume is reduced by about 20% to about 30%.
124. The method of embodiments 104-117, wherein fibrotic tissue volume is reduced by about 1% to about 60%.
125. The method of embodiments 104-117, wherein fibrotic tissue volume is reduced by about 3% to about 60%.
126. The method of embodiments 104-117, wherein fibrotic tissue volume is reduced by about 5% to about 60%.
127. The method of embodiments 104-117, wherein fibrotic tissue volume is reduced by about 10% to about 60%.
128. The method of embodiments 104-117, wherein fibrotic tissue volume is reduced by about 15% to about 60%.
129. The method of embodiments 104-117, wherein fibrotic tissue volume is reduced by about 20% to about 60%.
130. The method of embodiments 104-117, wherein fibrotic tissue volume is reduced by about 1% to about 45%.
131. The method of embodiments 104-117, wherein fibrotic tissue volume is reduced by about 3% to about 45%.
132. The method of embodiments 104-117, wherein fibrotic tissue volume is reduced by about 5% to about 45%.
133. The method of embodiments 104-117, wherein fibrotic tissue volume is reduced by about 10% to about 45%.
134. The method of embodiments 104-117, wherein fibrotic tissue volume is reduced by about 15% to about 45%.
135. The method of embodiments 104-117, wherein fibrotic tissue volume is reduced by about 20% to about 45%.
136. The method of embodiments 104-135, wherein fibrotic tissue dermal fibrosis area is reduced by about 1% to about 50%.
137. The method of embodiments 104-135, wherein fibrotic tissue dermal fibrosis area is reduced by about 3% to about 50%.
138. The method of embodiments 104-135, wherein fibrotic tissue dermal fibrosis area is reduced by about 5% to about 50%.
139. The method of embodiments 104-135, wherein fibrotic tissue dermal fibrosis area is reduced by about 10% to about 50%.
140. The method of embodiments 104-135, wherein fibrotic tissue dermal fibrosis area is reduced by about 15% to about 50%.
141. The method of embodiments 104-135, wherein fibrotic tissue dermal fibrosis area is reduced by about 20% to about 50%.
142. The method of embodiments 104-135, wherein fibrotic tissue dermal fibrosis area is reduced by about 1% to about 30%.
143. The method of embodiments 104-135, wherein fibrotic tissue dermal fibrosis area is reduced by about 3% to about 30%.
144. The method of embodiments 104-135, wherein fibrotic tissue dermal fibrosis area is reduced by about 5% to about 30%.
145. The method of embodiments 104-135, wherein fibrotic tissue dermal fibrosis area is reduced by about 10% to about 30%.
146. The method of embodiments 104-145, wherein fibrotic tissue dermal fibrosis percent is reduced by about 1% to about 70%.
147. The method of embodiments 104-145, wherein fibrotic tissue dermal fibrosis percent is reduced by about 3% to about 70%.

148. The method of embodiments 104-145, wherein fibrotic tissue dermal fibrosis percent is reduced by about 5% to about 70%.
149. The method of embodiments 104-145, wherein fibrotic tissue dermal fibrosis percent is reduced by about 10% to about 70%.
150. The method of embodiments 104-145, wherein fibrotic tissue dermal fibrosis percent is reduced by about 15% to about 70%.
151. The method of embodiments 104-145, wherein fibrotic tissue dermal fibrosis percent is reduced by about 20% to about 70%.
152. The method of embodiments 104-145, wherein fibrotic tissue dermal fibrosis percent is reduced by about 1% to about 35%.
153. The method of embodiments 104-145, wherein fibrotic tissue dermal fibrosis percent is reduced by about 3% to about 35%.
154. The method of embodiments 104-145, wherein fibrotic tissue dermal fibrosis percent is reduced by about 5% to about 35%.
155. The method of embodiments 104-145, wherein fibrotic tissue dermal fibrosis percent is reduced by about 10% to about 35%.
156. The method of embodiments 104-145, wherein fibrotic tissue dermal fibrosis percent is reduced by about 15% to about 35%.
157. The method of embodiments 104-145, wherein fibrotic tissue dermal fibrosis percent is reduced by about 20% to about 35%.
158. The method of embodiments 104-145, wherein fibrotic tissue dermal fibrosis percent is reduced by about 25% to about 35%.
159. The method of embodiments 104-158, wherein fibrotic tissue epidermal fibrosis area is reduced by about 1% to about 75%.
160. The method of embodiments 104-158, wherein fibrotic tissue epidermal fibrosis area is reduced by about 3% to about 75%.
161. The method of embodiments 104-158, wherein fibrotic tissue epidermal fibrosis area is reduced by about 5% to about 75%.
162. The method of embodiments 104-158, wherein fibrotic tissue epidermal fibrosis area is reduced by about 10% to about 75%.
163. The method of embodiments 104-158, wherein fibrotic tissue epidermal fibrosis area is reduced by about 15% to about 75%.
164. The method of embodiments 104-158, wherein fibrotic tissue epidermal fibrosis area is reduced by about 20% to about 75%.
165. The method of embodiments 104-158, wherein fibrotic tissue epidermal fibrosis area is reduced by about 25% to about 75%.
166. The method of embodiments 104-158, wherein fibrotic tissue epidermal fibrosis area is reduced by about 1% to about 50%.
167. The method of embodiments 104-158, wherein fibrotic tissue epidermal fibrosis area is reduced by about 3% to about 50%.
168. The method of embodiments 104-158, wherein fibrotic tissue epidermal fibrosis area is reduced by about 5% to about 50%.
169. The method of embodiments 104-158, wherein fibrotic tissue epidermal fibrosis area is reduced by about 10% to about 50%.
170. The method of embodiments 104-158, wherein fibrotic tissue epidermal fibrosis area is reduced by about 15% to about 50%.
171. The method of embodiments 104-158, wherein fibrotic tissue epidermal fibrosis area is reduced by about 20% to about 50%.
172. The method of embodiments 104-158, wherein fibrotic tissue epidermal fibrosis area is reduced by about 25% to about 50%.
173. The method of embodiments 104-158, wherein fibrotic tissue epidermal fibrosis area is reduced by about 30% to about 50%.
174. The method of embodiments 104-173, wherein fibrotic tissue epidermal fibrosis percent is reduced by about 1% to about 75%.
175. The method of embodiments 104-173, wherein fibrotic tissue epidermal fibrosis percent is reduced by about 3% to about 75%.
176. The method of embodiments 104-173, wherein fibrotic tissue epidermal fibrosis percent is reduced by about 5% to about 75%.
177. The method of embodiments 104-173, wherein fibrotic tissue epidermal fibrosis percent is reduced by about 10% to about 75%.
178. The method of embodiments 104-173, wherein fibrotic tissue epidermal fibrosis percent is reduced by about 15% to about 75%.
179. The method of embodiments 104-173, wherein fibrotic tissue epidermal fibrosis percent is reduced by about 20% to about 75%.
180. The method of embodiments 104-173, wherein fibrotic tissue epidermal fibrosis percent is reduced by about 25% to about 75%.
181. The method of embodiments 104-173, wherein fibrotic tissue epidermal fibrosis percent is reduced by about 1% to about 50%.
182. The method of embodiments 104-173, wherein fibrotic tissue epidermal fibrosis percent is reduced by about 3% to about 50%.
183. The method of embodiments 104-173, wherein fibrotic tissue epidermal fibrosis percent is reduced by about 5% to about 50%.
184. The method of embodiments 104-173, wherein fibrotic tissue epidermal fibrosis percent is reduced by about 10% to about 50%.
185. The method of embodiments 104-173, wherein fibrotic tissue epidermal fibrosis percent is reduced by about 15% to about 50%.
186. The method of embodiments 104-173, wherein fibrotic tissue epidermal fibrosis percent is reduced by about 20% to about 50%.
187. The method of embodiments 104-173, wherein fibrotic tissue epidermal fibrosis percent is reduced by about 25% to about 50%.
188. The method of embodiments 104-173, wherein fibrotic tissue epidermal fibrosis percent is reduced by about 30% to about 50%.
189. The method of embodiments 104-188, wherein fibrotic tissue stiffness or rigidity is reduced by about 1% to about 75%.
190. The method of embodiments 104-188, wherein fibrotic tissue stiffness or rigidity is reduced by about 3% to about 75%.
191. The method of embodiments 104-188, wherein fibrotic tissue stiffness or rigidity is reduced by about 5% to about 75%.

192. The method of embodiments 104-188, wherein fibrotic tissue stiffness or rigidity is reduced by about 10% to about 75%.
193. The method of embodiments 104-188, wherein fibrotic tissue stiffness or rigidity is reduced by about 15% to about 75%.
194. The method of embodiments 104-188, wherein fibrotic tissue stiffness or rigidity is reduced by about 20% to about 75%.
195. The method of embodiments 104-188, wherein fibrotic tissue stiffness or rigidity is reduced by about 25% to about 75%.
196. The method of embodiments 104-188, wherein fibrotic tissue stiffness or rigidity is reduced by about 1% to about 45%.
197. The method of embodiments 104-188, wherein fibrotic tissue stiffness or rigidity is reduced by about 3% to about 45%.
198. The method of embodiments 104-188, wherein fibrotic tissue stiffness or rigidity is reduced by about 5% to about 45%.
199. The method of embodiments 104-188, wherein fibrotic tissue stiffness or rigidity is reduced by about 10% to about 45%.
200. The method of embodiments 104-188, wherein fibrotic tissue stiffness or rigidity is reduced by about 15% to about 45%.
201. The method of embodiments 104-188, wherein fibrotic tissue stiffness or rigidity is reduced by about 20% to about 45%.
202. The method of embodiments 104-188, wherein fibrotic tissue stiffness or rigidity is reduced by about 25% to about 45%.
203. The method of embodiments 104-188, wherein fibrotic tissue stiffness or rigidity is reduced by about 30% to about 45%.
204. The method of embodiments 104-203, wherein the composition is an injectable composition.
205. The method of embodiments 104-204, wherein the pharmaceutically acceptable salt is hydrochloride.

Non-Limiting Examples

The present disclosure is also described and demonstrated by way of the following non-limiting examples. However, the use of these and other examples anywhere in the specification is illustrative only and in no way limits the scope and meaning of the disclosure or of any exemplified term. Likewise, the disclosure is not limited to any particular embodiment or aspect described herein. Indeed, suitable modifications and variations may be apparent to those skilled in the art upon reading this specification, and such variations can be made without departing from the disclosure in spirit or in scope.

Using a known animal model for the evaluation of tissue fibrosis, such as fibrosis in the deep fascia, integumentary system, or skin tissue is disclosed herein.

Example 1 Memantine is Effective at Treating Fibromatosis Conditions

The present invention is based in part on the surprising discovery that administration of adamantane derivatives, such as memantine to individuals with symptoms of a fibromatosis condition will result in a reduction of one or more the characteristics of tissue fibromatosis. Thus, for the first time, it is shown that integumentary system fibromatosis conditions can be treated using compositions comprising memantine. Such compositions may be administered alone, or in combination with other therapies, including physical manipulation regimens. Use of memantine for the treatment of integumentary system fibromatosis conditions is particularly attractive because those of skill in the art are aware of commercial preparations of memantine and safety measures and parameters for preparing useful memantine preparations are also well known to those of skill in the art. The present application describes the first use of memantine in an integumentary system fibromatosis disorder. Example summarizes the study subject experimental methods, memantine treatment responses of the first subjects with a fibromatosis disorder treated with memantine.

Animal Model Designed to Determine Efficacy of Memantine for the Treatment of Bleomycin-Induced Dermal Fibrosis Study Subjects Forty-two normal male C57Bl/6 Mice were obtained from Charles River Laboratories. Mice age at the start of the study were from 6-8 weeks old. Study subjects were allocated as follows: 1 group of 6 mice and 3 groups of 12 mice each. Animals were not replaced during the study.

Animal Handling, Housing, and Husbandry

Study subject husbandry was standard conventional. Animals were maintained at 6-12 animals per cage. Caging consisted of reusable IVCs. Animals were handled on the bench top. Surfaces and materials were cleaned between groups. Animal bedding material consisted of Alpha-Dri® (Irradiated). Animal cages were changed once weekly. Animal food consisted of LabDiet 5053 (Irradiated). Animal water consisted of Milli-Q Water (RO/Ion-Exchange/UV Purified). Animal enrichment consisted of Enviro-dri, shepherd shacks, and sunnies (no nestlets).

Acclimation

Animals were acclimated for a minimum of three days prior to study commencement. During this period, the animals were observed daily in order to reject animals that presented in poor condition.

Environmental Conditions

The study was performed in animal rooms provided with filtered air at a temperature of 70+/−5° F. and 50%+/−20% relative humidity. Animal rooms were set to maintain a minimum of twelve to fifteen air changes per hour. The animal rooms were on an automatic timer for a light/dark cycle of twelve hours on and twelve hours off with no twilight.

Fibrosis Inducing Agent: Bleomycin

Bleomycin from Henry Schein (Cat #: 8700001) was obtained as a lyophilized powder. Unformulated Bleomycin was stored at 4° C. Formulated Bleomycin was prepared by mixing the lyophilized Bleomycin powder with saline to obtain a 0.4 mg/ml solution. Unused unformulated Bleomycin was retained. The prepared Bleomycin solution was aliquoted into 50 µL, 0.4 mg/ml Bleomycin parts and stored at −80° C. Bleomycin was prepared once and daily aliquots were frozen. Frozen aliquots were thawed daily for administration. Formulated Bleomycin was stable for a few hours at room temperature. Bleomycin was administered once daily on days 0-27 at 20 µg per subcutaneous injection. Unused formulated Bleomycin was disposed.

Test Article: Memantine

Memantine HCl from Selleckchem (Cat #: S2043) was obtained. Unformulated Memantine HCl was stored at −20° C. Memantine was formulated daily by the following procedure: dissolve memantine in a 50/50 mixture of Kolliphor® EL (Sigma, Cat #: C5135)/ethanol for a 4× concentration of 12 mg/ml. Once dissolved, 3 parts MilliQ water is added for a final concentration of 3 mg/ml for dosing (12.5% Kolliphor® EL, 12.5% ethanol, 75% water). Unused unformulated Memantine was disposed. Memantine was formulated daily and administered by intraperitoneal injection once daily on days 0-27 at 15 mg/kg; 0.1 mL/20 g (5 mL/kg). Formulated Memantine was stable at room temperature for a few hours. Unused formulated Memantine was disposed.

Experimental Procedures

Animal model studies were performed at BioModels (Waltham, MA, USA). Forty-two six- to eight-week-old C57Bl/6 male mice were initially enrolled in the study. Bleomycin-induced skin fibrosis was induced in thirty-six mice (Groups 2-4) by daily subcutaneous injection of bleomycin from Day 0 to Day 27 at two sites on the back, 2 centimeters apart on the midline of the back. An additional six animals served as the control group (Group 1) and received daily saline injections.

Animals were dosed with test articles, administered at least 60 minutes prior to Bleomycin or saline injections. All animals were weighed and evaluated daily. Where animals exhibited severe skin damage that appeared painful, they received buprenorphine up to twice daily as needed until the damage subsided.

Disease Induction

For induction of dermal fibrosis, mice were prepared for subcutaneous Bleomycin injection by gently shaving the hair on the back 1-2 days prior to the start of the experiment. Starting on Day 0 and continuing once daily through Day 27, animals in Groups 2-4 were administered Bleomycin (20 µg per dose in 50 µL volume) via subcutaneous injection (indicated with skin marker) at 2 sites on the back skin, 2 centimeters apart on the middle of the back (in the exact same location at two separate sites, as indicated with skin marker). Group 1 had identical injections of saline daily. Administration of bleomycin occurred at least 1 hour after dosing of test articles (AM dose).

Dosing

Animals in Group 2 (N=11) were dosed with vehicle (12.5% Kolliphor® EL, 12.5% ethanol, 75% water) by intraperitoneal injection daily between days 0-27. Animals in Group 3 were dosed with 15 mg/kg Memantine by intraperitoneal injection daily between days 0-27. Dosing occurred at least 60 minutes prior to subcutaneous Bleomycin and saline injections.

Body Weight and Survival

Animals were observed daily for weight, morbidity, survival, in order to assess possible differences among treatment groups and possible toxicity resulting from the treatments.

Supportive Care and Euthanasia Criteria

Animals in excess of 15% weight loss were given 1 ml of 0.9% NaCl subcutaneously daily. Animals in excess of 20% weight loss were given 1 mL NaCl subcutaneously twice daily and were provided with water softened food pellets. Any animal that lost greater than 30% of its body weight, showed an inability to eat, or was moribund, was euthanized and did not have samples collected. Animals that were found dead did not have samples collected.

Sacrifice and Terminal Sample Collection

All surviving animals were euthanized by CO2 inhalation on Day 28. Blood and skin samples were collected at sacrifice from all animals, as follows.

On day 28, upon sacrifice, about 0.2 ml of blood was collected into $K_2$EDTA tubes, processed to plasma, and plasma was frozen at −80° C. until shipment to sponsor. Following blood collection, one large section of skin containing both injection sites was collected. The sample closer to the head was sandwiched flat between foam and placed in a tissue cassette. The sample was then fixed in NBF for 24 hours before moving to ethanol. The second sample was then flash frozen and stored at −80° C. until shipment or use in downstream assays.

Skin Histopathology

Formalin-fixed samples were embedded in paraffin, sectioned at 5 micros, and separate and adjacent slides stained with hematoxylin and eosin (H&E) and Masson's Trichrome. All slides were evaluated by a board-certified veterinary pathologist. H&E and Masson's Trichrome stained slides underwent histological examination of fibrosis and dermal thickness was measured.

Histopathology studies were performed at Dallas Tissue Research. Preliminary quantification was performed at Reveal Biosciences.

Data Analysis and Statistical Analysis

Figures were prepared and statistical analysis was performed using JASP. Data was analyzed by either one-way ANOVA with either Dunnett's or Holm-Šídák's multiple comparisons test to compare all groups or with Student T test to compare only two groups.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. A method of reducing fibromatosis in a subject in need thereof, the method comprising contacting the fibrotic tissue with a therapeutically effective amount of memantine or a pharmaceutically acceptable salt thereof, wherein said fibromatosis condition is palmar fibromatosis (Dupuytren's disease).

2. The method of claim 1, wherein said subject is a mammal.

3. The method of claim 1, wherein said subject is a human.

4. The method of claim 1, wherein the therapeutically effective amount of memantine or a pharmaceutically acceptable salt thereof is administered through injection.

5. The method of claim 1, wherein the fibromatosis condition is an integumentary system fibromatosis condition.

6. The method of claim 5, wherein fibrotic tissue dermal fibrosis area is reduced by about 1% to about 35%.

7. The method of claim 5, wherein fibrotic tissue dermal fibrosis percent is reduced by about 1% to about 70%.

8. The method of claim 5, wherein fibrotic tissue epidermal fibrosis area is reduced by about 1% to about 75%.

9. The method of claim 5, wherein fibrotic tissue epidermal fibrosis percent is reduced by about 1% to about 75%.

10. The method of claim 1, wherein fibrotic tissue volume is reduced by about 1% to about 30%.

11. The method of claim 1, wherein fibrotic tissue volume is reduced by about 1% to about 60%.

12. The method of claim 1, wherein the pharmaceutically acceptable salt is hydrochloride.

\* \* \* \* \*